US010160968B2

(12) United States Patent
Wickens et al.

(10) Patent No.: US 10,160,968 B2
(45) Date of Patent: Dec. 25, 2018

(54) RNA TAGGING

(71) Applicant: Wisconsin Alumni Research Foundation, Madison, WI (US)

(72) Inventors: Marvin P. Wickens, Madison, WI (US); Christopher P. Lapointe, Madison, WI (US); Melanie A. Preston, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 442 days.

(21) Appl. No.: 14/946,020

(22) Filed: Nov. 19, 2015

(65) Prior Publication Data

US 2016/0138012 A1 May 19, 2016

Related U.S. Application Data

(60) Provisional application No. 62/081,915, filed on Nov. 19, 2014.

(51) Int. Cl.
*C12N 15/10* (2006.01)
*C07H 21/02* (2006.01)
*C12N 15/62* (2006.01)

(52) U.S. Cl.
CPC ......... *C12N 15/1065* (2013.01); *C07H 21/02* (2013.01); *C12N 15/62* (2013.01); *G01N 2570/00* (2013.01)

(58) Field of Classification Search
CPC .... C12N 15/1065; C12N 15/62; C07H 21/02; G01N 2570/00
See application file for complete search history.

(56) References Cited

PUBLICATIONS

Carlile, et al., Pseudouridine profiling reveals regulated mRNA pseudouridylation in yeast and human cells, Nature, 2014, 515(7525), 143-146.
Chang, et al., TAIL-seq: Genome-wide determination of poly(A) tail length and 3' end modifications, Molecular Cell, 2014, 53, 1044-1052.
Darnell, R. B., HITS-CHIP: panoramic views of protein-RNA regulation in living cells, Wiley Interdiscip Rev RNA, 2010, 1(2), 266-286.
Freeberg, et al., Pervasive and dynamic protein binding sites of the mRNA transcriptome in *Saccharomyces cerevisiae*, Genome Biology, 2013, 14:R13.
Geisberg, et al., Global analysis of mRNA isoform half-lives reveals stabilizing and destabilizing elements in yeast, Cell, 2014, 156, 812-824.

(Continued)

*Primary Examiner* — Jeremy C Flinders
(74) *Attorney, Agent, or Firm* — Quarles & Brady LLP

(57) ABSTRACT

Methods, kits, and compositions of matter suitable for use in RNA Tagging are disclosed. In one embodiment, a method includes: expressing a fusion protein within the cellular environment, the fusion protein including at least part of the protein of interest and a tagging domain, the tagging domain introducing a selective tag to an RNA to which the fusion protein selectively binds, the selective tag including a selective tag sequence or a selective covalent modification; allowing the tagging domain to tag the RNA to which the protein of interest selectively binds by waiting for about 1 minute to about 28 days; and identifying the tagged RNA.

15 Claims, 25 Drawing Sheets
(20 of 25 Drawing Sheet(s) Filed in Color)
Specification includes a Sequence Listing.

Express RBP/PUP fusion protein in cells

RBP/PUP 'tags' bound RNAs with 3' terminal uridines

5'══════════════════════════════════UUUUUUUU 3'

Identify tagged RNAs by RT-PCR or sequencing

(56) References Cited

PUBLICATIONS

Gerber, et al., Extensive association of functionally and cytotopically related mRNAs with Puf family RNA-binding proteins in yeast, PLoS Biology, 2004, 2(3), 342-354.

Hafner, et al., Transcriptome-wide identification of RNA-binding protein and microRNA target sites by PAR-CLIP, Cell, 2010, 141, 129-141.

Konig, et al., iCLIP reveals the function of hnRNP particles in splicing at individual nucleotide resolution, Nature Structural and Molecular Biology, 2010, 17(7), 909-915.

Kusov, et al., A new G-tailing method for the determination of the poly(A) tail length applied to hepatitis A virus RNA, Nucleic Acids Res., 2001, 29(12), e57.

Kwak, et al., A family of poly(U) polymerases, RNA, 2007, 13, 860-867.

Lane, et al., Stability and kinetics of G-quadruplex structures, Nucleic Acids Res., 2008, 36(17), 5482-5515.

Lapointe, et al., Protein-RNA networks revealed through covalent RNA marks, Nature Methods, 2015, 12, 1163-1170.

Lapoint, et al., The nucleic acid-binding domain and translational repression activity of a Xenopus terminal uridylyl transferase, J Biol Chem, 2013, 288(28), 20723-20733.

Licatalosi, et al., HITS-CLIP yeilds genome-wide insights into bean alternative RNA processing, Nature, 2008, 456(27), 464-469.

McHugh, et al., Methods for comprehensive experimental identification of RNA-protein interactions, Genome Biology, 2014, 15:203.

Mili, et al. Evidence for reassociation of RNA-binding proteins after cell lysis: Implications for the interpretation of immunoprecipitation analyses, RNA, 2004, 10, 1692-1694.

Riley, et al., Association of argonaute proteins and microRNAs can occur after cell lysis, RNA, 2012, 18, 1581-1585.

Riley, et al., The "observer effect" in genome-wide surveys of protein-RNA interactions, Molecular Cell, 2013, 49, 601-604.

Subtelny, et al., Poly(A)-tail profiling reveals an embryonic switch in translational control, Nature, 2014, 508(7494), 66-71.

Tenenbaum, et al., Identifying mRNA subsets in messenger ribonucleoprotein complexes by using cDNA arrays, PNAS, 2000, 97(26), 14085-14090.

Ule, et al., CLIP identifies nova-regulated RAN networks in the brain, Science, 2003, 302, 1212-1215.

Wickens, et al., A PUF family portrait: 3'UTR regulation as a way of life, Trends in Genetics, 2002, 18(3), 150-157.

Zhao, et al., Genome-wide identification of polycomb-associated RNAs by RIP-seq, Molecular Cell, 2010, 40, 939-953.

Zhu, et al., A 5' cytosine binding pocket in Puf3p specifies regulation of mitochondrial mRNAs, PNAS, 2009, 106(48), 20192-20197.

| | RIP-seq | CLIP-seq | RNA Tagging |
|---|---|---|---|
| Simple | – | – | ✓++ |
| Fast | ✓ | – | ✓+ |
| Reliable | ✓ | ✓++ | ✓+ |
| Low cell input | – | – | ✓+ |
| Binding element determination | ✓ | ✓++ | ✓ |
| In vivo binding affinity insight | – | – | ✓ |
| Inexpensive | ✓ | – | ✓ |
| High-throughput compatible | – | – | ✓ |

Figure 2

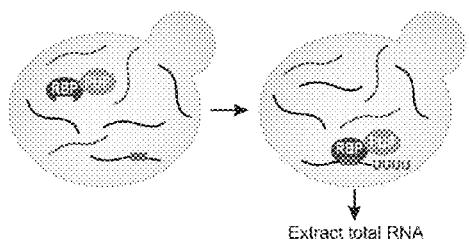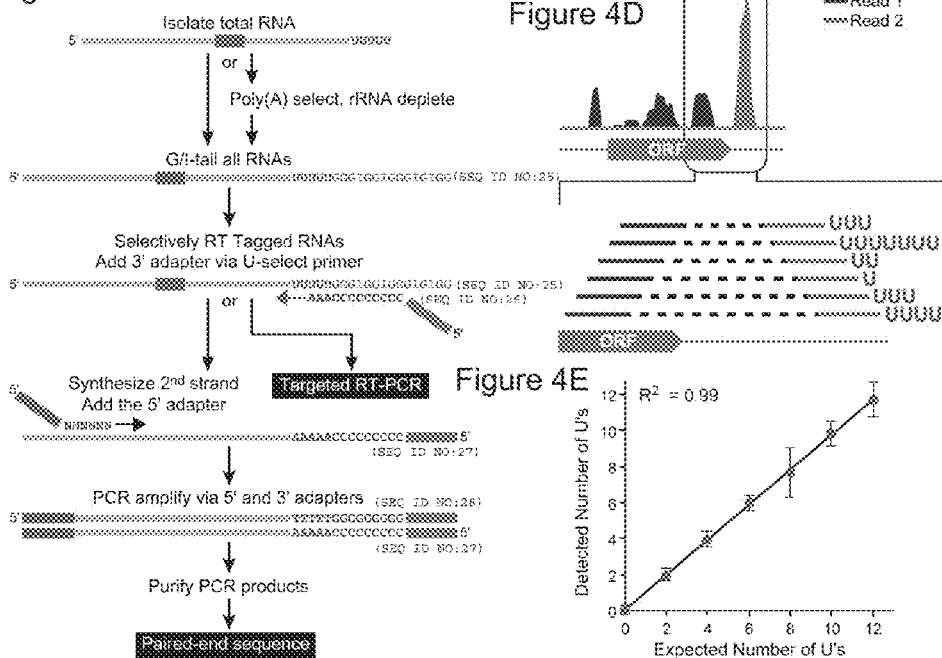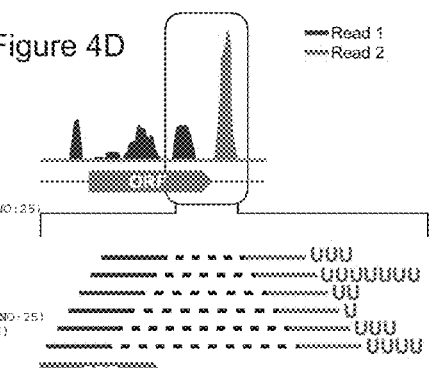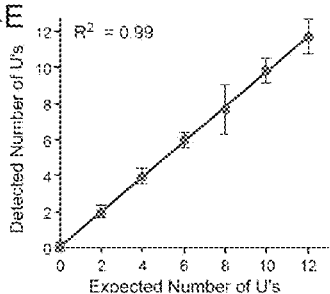

Figure 5A
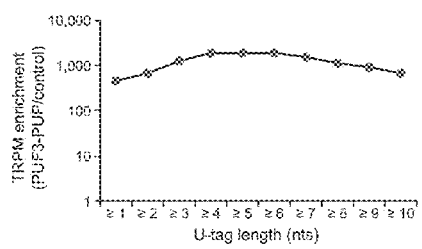
Figure 5B
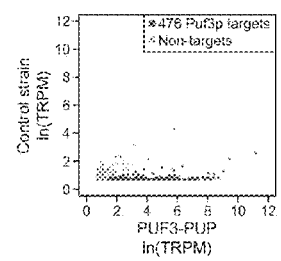
Figure 5C
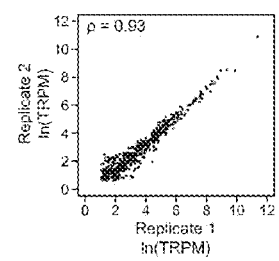
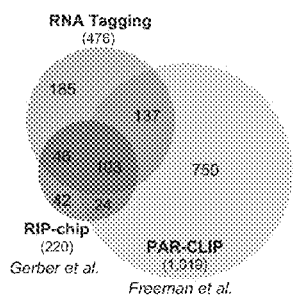
Figure 5D
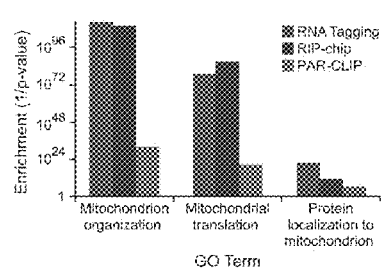
Figure 5E
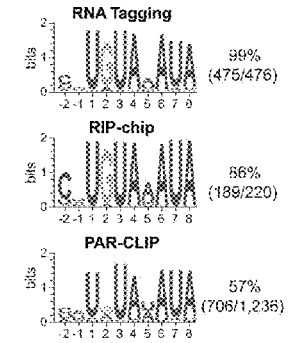
Figure 5F Figure 6A
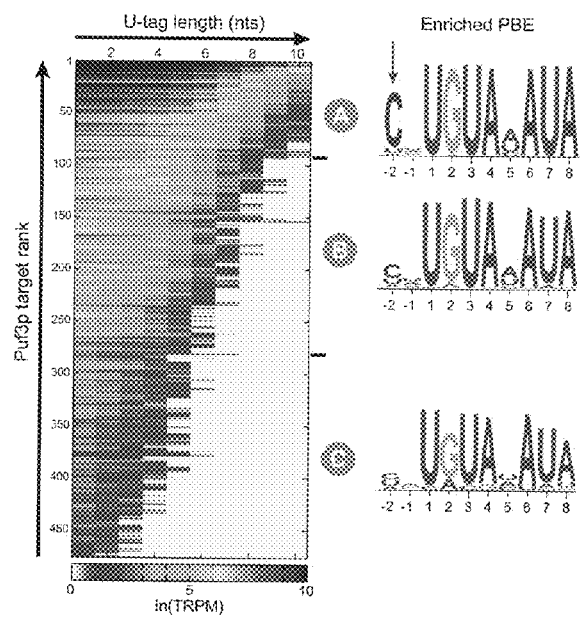
Figure 6B
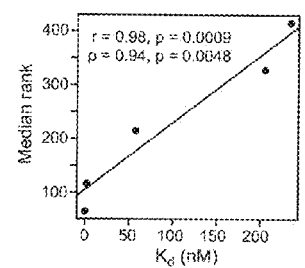
Figure 6C
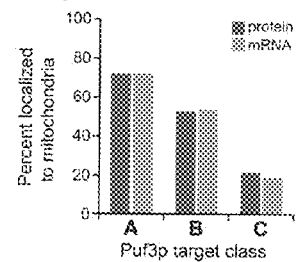
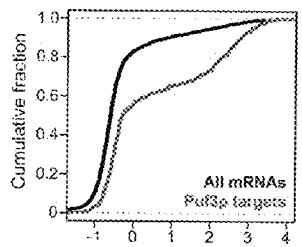
Mitochondria-associated translation
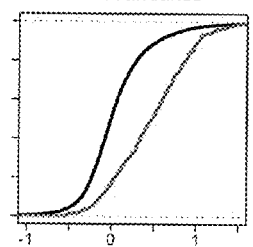
*PUF3* effect on RNA abundance
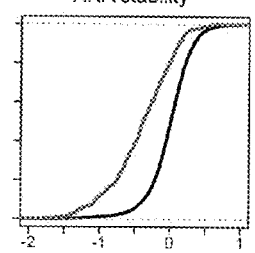
*PUF3* effect on RNA stability
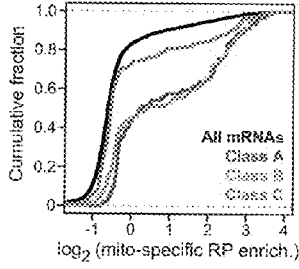
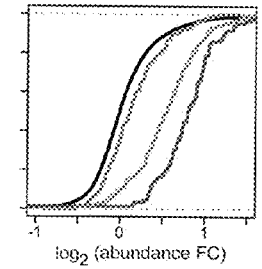
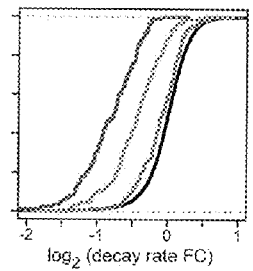
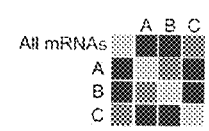
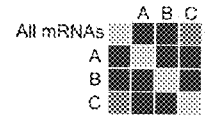
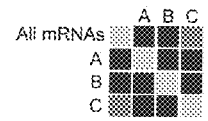
Figure 6D　　　　　Figure 6E　　　　　Figure 6F

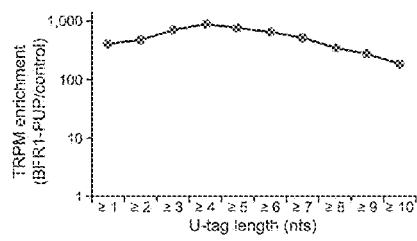
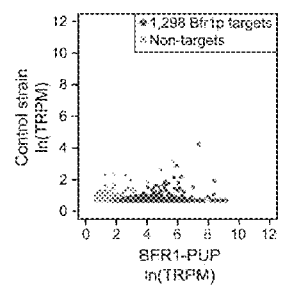
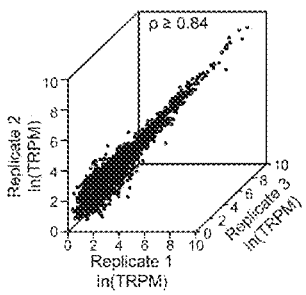
Figure 7A  Figure 7B  Figure 7C
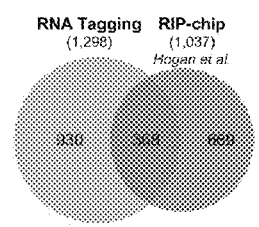
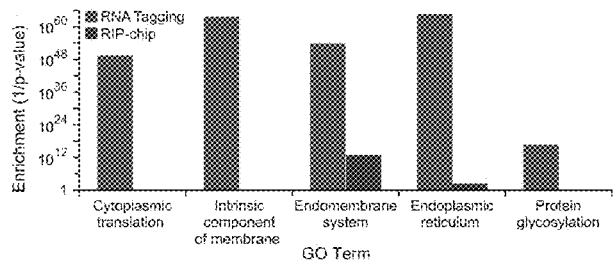
Figure 7D  Figure 7E

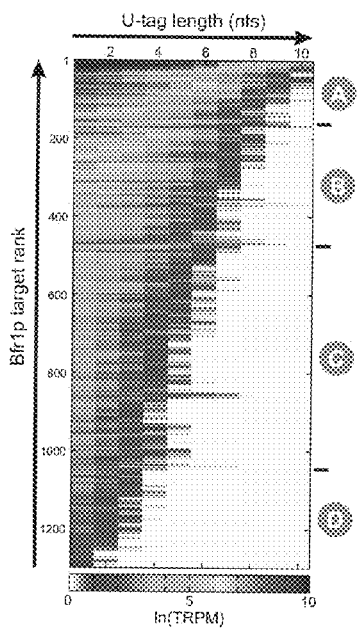
Figure 8A
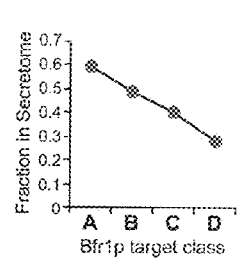
Figure 8B
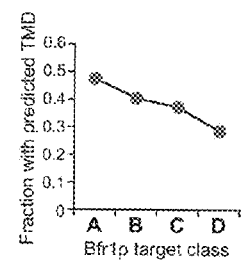
Figure 8C
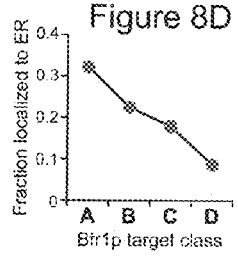
Figure 8D
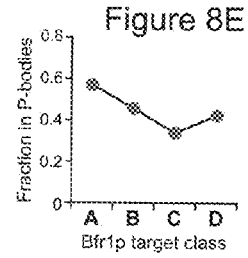
Figure 8E
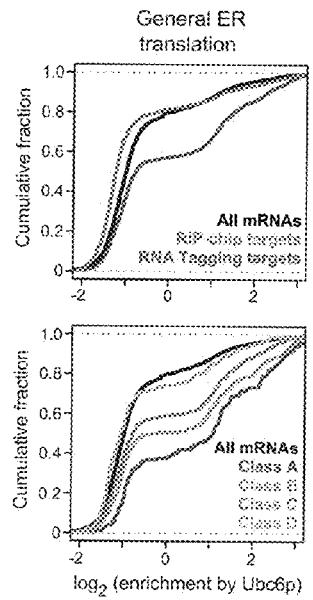
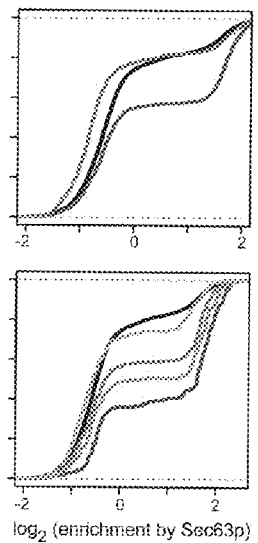
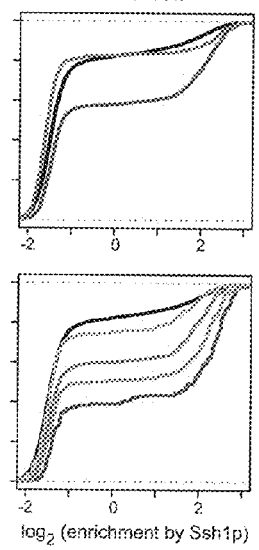
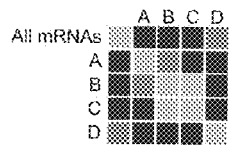
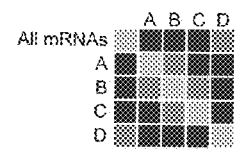
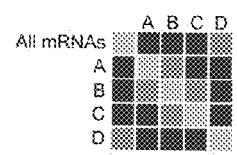
Figure 8F     Figure 8G     Figure 8H Figure 9A
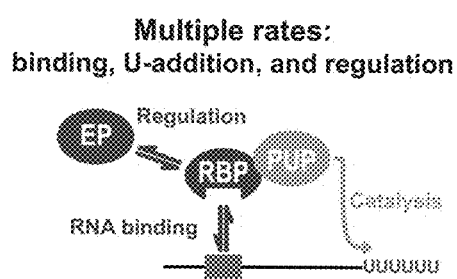
Figure 9B
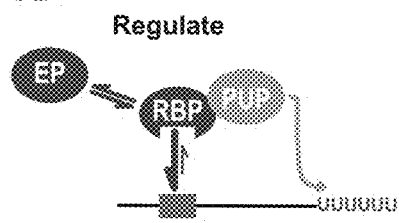
Figure 9C

Figure 10A
RT primers:
 dT: 5'-TTTTTTTTTTTTTTTTTTTT-3' (SEQ ID NO:29)
 U-select: 5'-GCCTTGGCACCCGAGAATTCCACCCCCCCCCAAA-3' (SEQ ID NO:4)
 (U-sel)

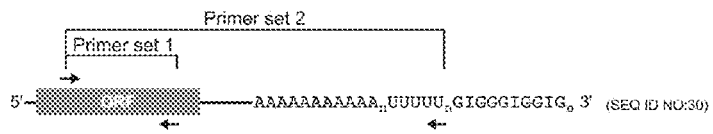

5'—▨▨▨▨▨▨—AAAAAAAAAAA$_{11}$UUUUU$_2$GIGGGIGGIG$_0$ 3' (SEQ ID NO:30)

Figure 10B
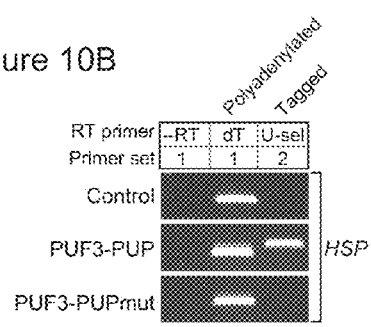

HSP10

Figure 10C
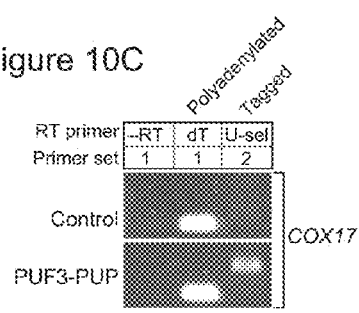

COX17

Figure 10D
HSP10 3'UTR    Poly(A) tail    U-tag

AATTGAAAAAAAAAAAAAAAAAAAAAAAAAATTTTTTTTTTT (SEQ ID NO:31)
AATTGAACTCAAAAAAAAAAAAAAAAAAAAAAAAAATTTTTTTTTTTTT (SEQ ID NO:32)
AATTGAACTCAAAAAAAAAAAAAAAAAAAAAAAATTTTT (SEQ ID NO:33)
AATTGAACTCAAATTTCTTCAAAAAAAAAAAAATTTT (SEQ ID NO:34)

Figure 10E
PHD1-WT —☐—//—☐— UGUAGUUA —☐— UGUAACAUUA —☐— (SEQ ID NO:2)
PHD1-mutant —☐—//—☐— ACAAGUUA —☐— ACAAACAUUA —☐— (SEQ ID NO:3)

Figure 10F

| RT primer | −RT | dT | U-sel |
|---|---|---|---|
| Primer set | 1 | 1 | 2 |

Control
PUF5-PUP          PHD1-WT
PUF5-PUPmut
PUF5-PUP          PHD1-mutant

Figure 11A

U0: 5'-GTTCAGAGTTCTACAGTCCGACGATCAAAAAAAAAAA*TTTGGGGGGGGTGGAATTCTCGGGTGCCAAGG-3' (SEQ ID NO:35)
U2: 5'-GTTCAGAGTTCTACAGTCCGACGATCAAAAAAAAAAATTTTGGGGGGGGTGGAATTCTCGGGTGCCAAGG-3' (SEQ ID NO:36)
U4: 5'-GTTCAGAGTTCTACAGTCCGACGATCAAAAAAAAAAATTTTTTGGGGGGGGTGGAATTCTCGGGTGCCAAGG-3' (SEQ ID NO:37)
U6: 5'-GTTCAGAGTTCTACAGTCCGACGATCAAAAAAAAAAATTTTTTTTGGGGGGGGTGGAATTCTCGGGTGCCAAGG-3' (SEQ ID NO:38)
U8: 5'-GTTCAGAGTTCTACAGTCCGACGATCAAAAAAAAAAATTTTTTTTTTGGGGGGGGTGGAATTCTCGGGTGCCAAGG-3' (SEQ ID NO:39)
U10: 5'-GTTCAGAGTTCTACAGTCCGACGATCAAAAAAAAAAATTTTTTTTTTTTGGGGGGGGTGGAATTCTCGGGTGCCAAGG-3' (SEQ ID NO:40)
U12: 5'-GTTCAGAGTTCTACAGTCCGACGATCAAAAAAAAAAATTTTTTTTTTTTTTGGGGGGGGTGGAATTCTCGGGTGCCAAGG-3' (SEQ ID NO:41)

Key:
Illumina 5' adapter: GTTCAGAGTTCTACAGTCCGACGATC (SEQ ID NO:42)
Poly(A) tail mimic: AAAAAAAAAAA (SEQ ID NO:43)
U-tag mimic: TTTTTTTTTTTT (SEQ ID NO:44)
U-select RT primer: TTTGGGGGGGGTGGAATTCTCGGGTGCCAAGG (SEQ ID NO:15)

Figure 11B  Percent composition of the starred (*) position in panel (a)

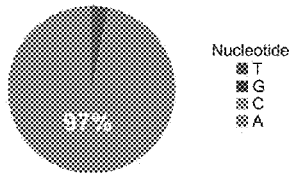

Nucleotide
▪ T
▪ G
▪ C
▪ A

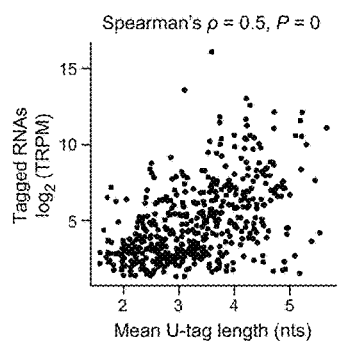
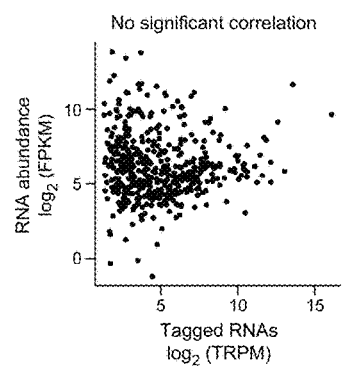
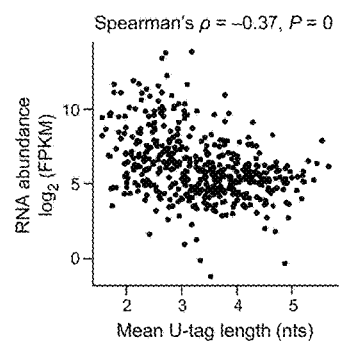
Figure 12A
Figure 12B
Figure 12C

Figure 16A

| | Puf3p binding elements | $K_d$ (nM) | $K_{rel}$ |
|---|---|---|---|
| (SEQ ID NO:45) | CCUGUAAAUA | 0.31 | 1 |
| (SEQ ID NO:46) | CCUGUAUAUA | 1.6 | 5 |
| (SEQ ID NO:47) | CUUGUAUAUA | 3 | 10 |
| (SEQ ID NO:48) | ACUGUAAAUA | 58 | 187 |
| (SEQ ID NO:49) | UUUGUAUAUA | 205 | 661 |
| (SEQ ID NO:50) | AUUGUAUAUA | 234 | 755 |

Determined in:
Zhu et al. PNAS (2009) A 5' cytosine binding pocket in Puf3p specifies regulation of mitochondrial mRNAs.

Figure 18

| mRNA tested | WT Half-life | puf3Δ Half-life | Fold Change (puf3Δ / WT) | Puf3p Target Class | Puf3p Target Rank | PBE | |
|---|---|---|---|---|---|---|---|
| YLL009C | 4.0 | 24.3 | 6.1 | A | 5 | CUUGUAUAUA | (SEQ ID NO:47) |
| YML009C | 2.9 | 6.7 | 2.3 | A | 11 | CCUGUAAAUA | (SEQ ID NO:45) |
| YKL087C | 1.7 | 4.6 | 2.7 | A | 60 | CCUGUAAAUA | (SEQ ID NO:45) |
| YNR037C | 4.2 | 8.5 | 2.0 | A | 12 | CAUGUAAAUA | (SEQ ID NO:51) |
| YOR187W | 5.5 | 16.7 | 3.0 | A | 25 | CGUGUAAAUA | (SEQ ID NO:52) |
| YNR017W | 3.1 | 8.0 | 2.6 | A | 47 | CUUGUAUAUA | (SEQ ID NO:47) |
| YDR347W | 3.2 | 5.1 | 1.6 | B | 132 | UCUGUAAAUA | (SEQ ID NO:53) |
| YNL315C | 3.8 | 10.2 | 2.7 | B | 183 | CCUGUAAAUA | (SEQ ID NO:45) |
| YHR147C | 3.0 | 4.8 | 1.6 | B | 131 | CUUGUAAAUA | (SEQ ID NO:54) |
| YOR158W | 1.7 | 7.2 | 4.2 | B | 125 | CAUGUAUAUA | (SEQ ID NO:55) |
| YBL090W | 3.1 | 4.7 | 1.5 | B | 202 | UUUGUAAAUA | (SEQ ID NO:56) |
| YDR041W | 3.2 | 3.0 | 0.9 | C | 362 | CUUGUAAAUA | (SEQ ID NO:45) |
| YDL069C | <2.0 | <2.0 | 1.0 | NA | NA | NA | |

** All half-lives taken from Miller, et al. NAR (2013)
** "NA" indicates the gene was not identified as a Puf3p target using RNA Tagging.

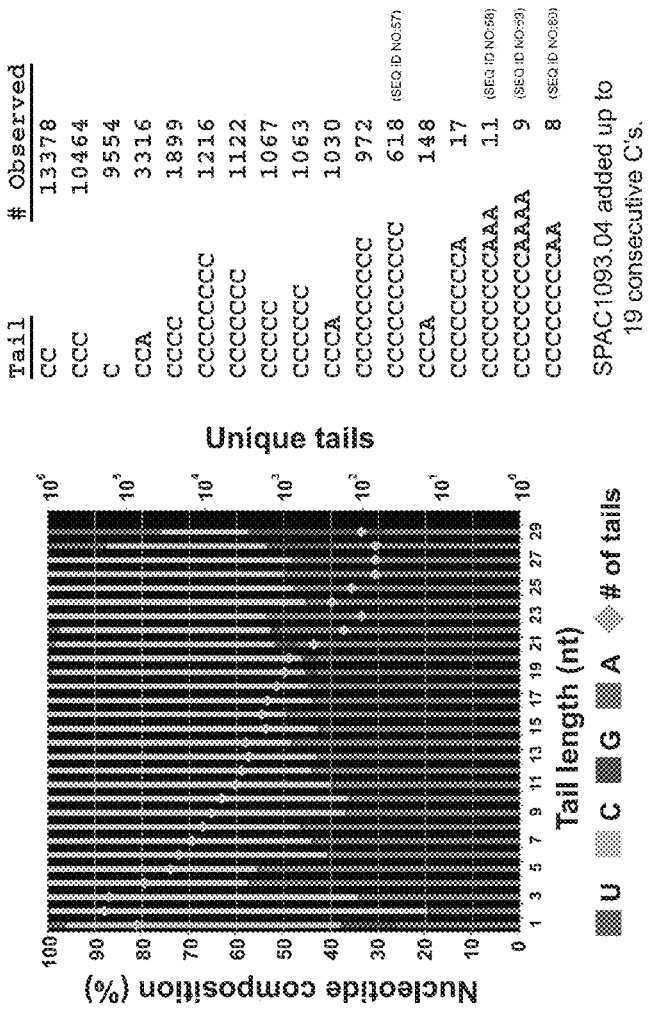
Figure 25A
Figure 25B
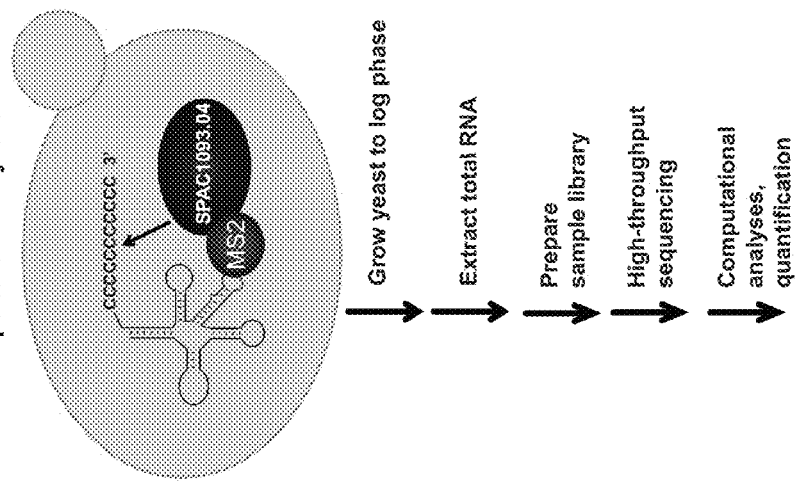
Figure 25C
| Tail | # Observed | |
|---|---|---|
| CC | 13378 | |
| CCC | 10464 | |
| C | 9554 | |
| CCA | 3316 | |
| CCCC | 1899 | |
| CCCCCCC | 1216 | |
| CCCCCC | 1122 | |
| CCCCC | 1067 | |
| CCCCCC | 1063 | |
| CCCA | 1030 | |
| CCCCCCCC | 972 | |
| CCCCCCCCCC | 618 | (SEQ ID NO:57) |
| CCCA | 148 | |
| CCCCCCCCA | 17 | |
| CCCCCCCCAAAA | 11 | (SEQ ID NO:58) |
| CCCCCCCAAAAA | 9 | (SEQ ID NO:59) |
| CCCCCCCCAA | 8 | (SEQ ID NO:60) |
SPAC1093.04 added up to 19 consecutive C's.

RNA TAGGING

CROSS-REFERENCE TO RELATED APPLICATIONS

This application claims the benefit of U.S. Provisional Patent Application 62/081,915 filed Nov. 19, 2014.

STATEMENT REGARDING FEDERALLY SPONSORED RESEARCH

This invention was made with government support under GM050942 and GM031892 awarded by the National Institutes of Health. The government has certain rights in the invention.

BACKGROUND OF THE INVENTION

This invention relates to selective RNA Tagging.

Proteins are critical regulators of RNA. Proteins that bind RNA—RNA-binding proteins (RBPs)—affect the localization, stability, translation, and activity of their RNA targets. RBPs are critical in many biological processes, including early development, stem cell maintenance and neuronal function. Thus, identifying which RNAs are bound by which RBP is vital to understanding how genes are controlled and how defects in RNA regulation lead to human disease.

A need exists for kits and methods to achieve the aforementioned goals.

SUMMARY OF THE INVENTION

The present invention overcomes the aforementioned drawbacks by providing kits, compositions of matter, and methods as described herein.

In one embodiment, this disclosure provides a method for identifying, among a total RNA population, an RNA to which a protein of interest selectively binds in a cellular environment of a cell of interest. The method can include one or more of the following steps: expressing a fusion protein within the cellular environment, the fusion protein comprising at least part of the protein of interest and a tagging domain, the tagging domain introducing a selective tag to the RNA to which the protein of interest selectively binds, the selective tag comprising a selective tag sequence or a selective covalent modification; allowing the tagging domain to tag the RNA to which the protein of interest selectively binds by waiting for about 1 minute to about 28 days; and identifying the tagged RNA. The identifying step can further include one or more of the following steps: isolating the total RNA population of the cell of interest from other cellular material resulting in isolated total RNA; reverse transcribing the isolated total RNA using a primer having a sequence that is complementary to at least part of the selective tag sequence or the selective covalent modification resulting in a single-stranded cDNA complementary to RNA including the selective tag; and sequencing a dsDNA including the single-stranded cDNA complementary to RNA including the selective tag.

In another embodiment, this disclosure provides a composition of matter. The composition of matter can include a cell having a fusion protein, the fusion protein including a protein fused to a tagging domain. In a preferred embodiments, the tagging domain is *Caenorhabditis elegans* poly (U) polymerase (PUP-2).

In yet another embodiment, this disclosure provides a method for determining the binding affinity between a protein of interest and a particular RNA sequence. The method can include one or more of the following steps: contacting an RNA population with a fusion protein comprising the protein of interest and a tagging domain, the RNA population including RNAs having a particular RNA sequence, the tagging domain introducing a selective tag to RNAs to which the fusion protein selectively binds, the selective tag comprising a selective tag sequence or a selective covalent modification; measuring the length of the selective tag on the RNAs having the particular RNA sequence; and determining the binding affinity using the length of the selective tag.

In a further embodiment, this disclosure provides a method for identifying, among a total RNA population of a cell of interest, any RNA to which any protein of interest selectively binds in a cellular environment of the cell of interest. The method can include one or more of the following steps: expressing a fusion protein within the cellular environment, the fusion protein comprising the protein of interest and a tagging domain, the tagging domain introducing a selective tag to RNA to which the fusion protein selectively binds, the selective tag comprising a selective tag sequence or a selective covalent modification; isolating RNA from the cell resulting in isolated total RNA; attaching an in vitro added tail to the 3' end of the isolated total RNA resulting in tailed total RNA, the in vitro added tail comprising a tail sequence; selectively reverse transcribing the tailed total RNA using a primer having a sequence that is complementary to at least part of the selective tag sequence or the selective covalent modification and at least part of the tail sequence resulting in a single-stranded cDNA complementary to RNA including the selective tag and the tail; synthesizing a cDNA strand complementary to the single-stranded cDNA resulting in a dsDNA; amplifying the dsDNA; purifying the amplified dsDNA resulting in purified dsDNA; and sequencing the purified dsDNA.

In another embodiment, this disclosure provides a method of selectively sequencing a sub-selection of a total RNA population. The method can include one or more of the following steps: selectively tagging the sub-selection with a selective tag having a selective sequence or a selective covalent modification; in vitro tailing the total RNA population; selectively reverse transcribing the sub-selection using a primer having a sequence that is complementary to at least part of the selective tag sequence or the selective covalent modification and at least part of the in vitro-added tail sequence to produce cDNA complementary to the sub-selection; and sequencing a dsDNA containing the cDNA complementary to the sub-selection.

In yet another embodiment, this disclosure provides a kit for identifying RNAs to which a protein of interest selectively bind. The kit can include a fusion protein or a means of expressing a fusion protein within a cellular environment, the fusion protein comprising the protein of interest and a tagging domain fused to the RNA binding protein of interest, the fusion protein selectively 3' tagging the RNA to which the protein of interest selectively binds with a selective tag, the selective tag having a selective sequence or a selective covalent modification, and one or more of the following: a means of in vitro tailing an RNA population with a non-selective tag having a non-selective sequence; and a primer having a sequence that is complementary to at least part of the selective sequence or the selective covalent modification.

In a further embodiment, this disclosure provides a method of determining if an RNA of interest is regulated by a protein of interest. The method can include one or more of the following steps: contacting the RNA of interest with a fusion protein comprising the protein of interest and a tagging domain, the tagging domain introducing a selective tag to RNAs to which the fusion protein selectively binds, the selective tag comprising a selective tag sequence or a selective covalent modification; allowing the tagging domain to tag the RNAs to which the fusion protein selectively binds by waiting for about 1 minute to about 28 days; measuring the length of the selective tag on the RNA of interest; and determining if the RNA of interest is regulated by the protein of interest using the length of the selective tag or the selective covalent modification.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS AND EXHIBITS

The patent or application file contains at least one drawing executed in color. Copies of this patent or patent application publication with color drawing(s) will be provided by the Office upon request and payment of the necessary fee.

FIG. 2 is a diagram showing the relative advantages of the methods disclosed herein when compared with RIP-seq and CLIP-seq. Key: double negative sign, very poor; negative sign, poor; check mark, good; check and single plus sign, very good; check and double plus sign, outstanding.

Figure 1:
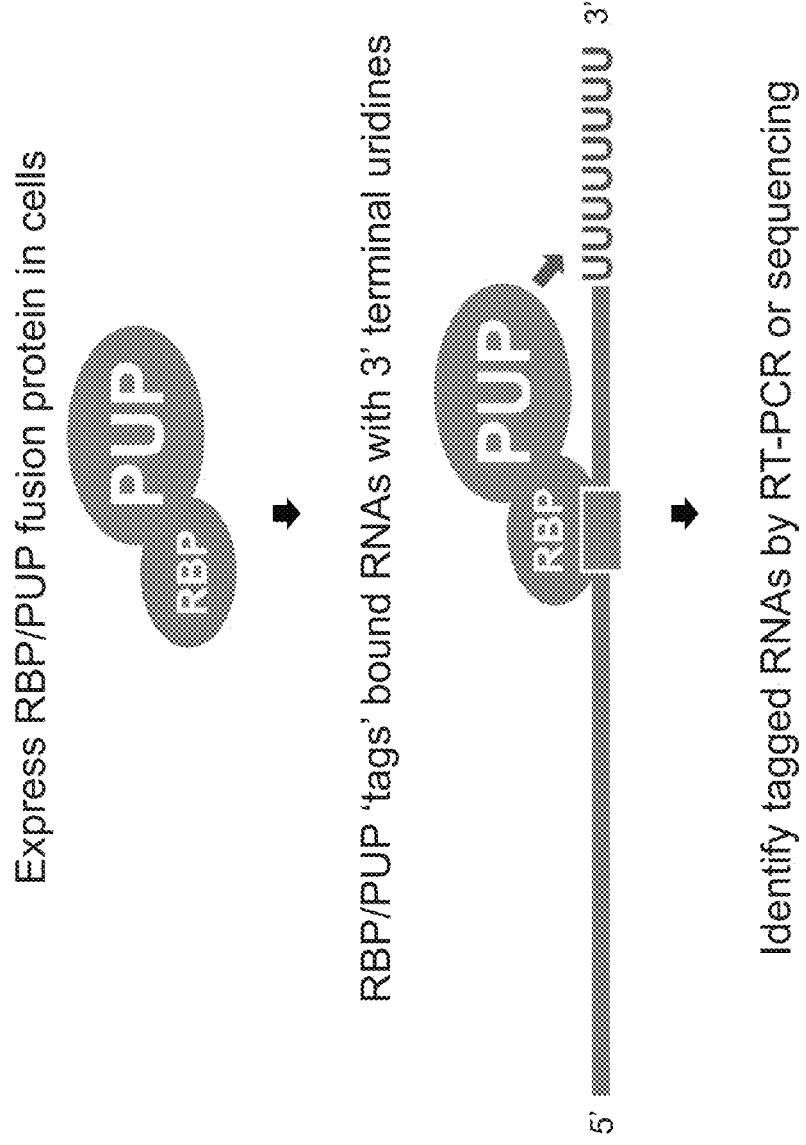
FIG. 1 is a schematic representation of an RNA Tagging method, in accordance with the present disclosure.

FIG. 4A explains the RNA Tagging approach, specifically, the strategy. RBP, RNA-binding protein, PUP, poly(U) polymerase.

FIG. 4B explains the RNA Tagging approach, specifically, schematic of targeted RT-PCR and transcriptome-wide RNA Tagging assays. RNAs are tailed with a combination of guanosines (G) and inosines (I) (purple). The U-select primer contained the Illumina 3' adapter sequence (brown), nine cytosines (purple) that base pair with the G/I tail, and three adenosines (red) that select for uridines at the 3' end of the mRNA.

FIG. 4C explains the RNA Tagging approach, specifically computational identification of Tagged RNAs. A-tails refers to the poly(A) tail and U-tails refers to 3' terminal uridines, which were often in the U-tag.

FIG. 4D explains the RNA Tagging approach, specifically, nature of the data. The cartoon depicts Tagged RNAs aligned to a representative gene. ORF, open reading frame.

FIG. 4E explains the RNA Tagging approach, specifically, plot of the mean U-tag length detected by high-throughput sequencing of synthetic DNA libraries that contained U-tags of 0, 2, 4, 6, 8, 10, and 12 nucleotides. At least 50,000 reads were detected for each library (>1 million total reads). The $R^2$ value ($R^2=0.99$, n=7) was determined by linear regression analysis, and error bars represent standard deviation.

FIG. 5A describes RNA Tagging identified transcriptome-wide Puf3p targets, specifically, enrichment of Tagged RNAs detected across different U-tag lengths in PUF3-PUP yeast relative to a control yeast strain (BY4742). Enrichment was calculated as a ratio of TRPMs obtained in strains with and without the PUF3-PUP chimera. TRPM, Tagged RNAs per million uniquely mapped reads.

FIG. 5B describes RNA Tagging identified transcriptome-wide Puf3p targets, specifically, scatter plot of Tagged RNAs detected in the PUF3-PUP strain relative to the control strain (BY4742). Puf3p target mRNAs (see Methods) are colored green; non-targets are grey.

FIG. 5C describes RNA Tagging identified transcriptome-wide Puf3p targets, specifically, plot of the number of Tagged RNAs detected for the 476 Puf3p targets in two biological replicates. Spearman's correlation coefficient ($\rho$) is indicated ($\rho=0.93$, P=0, n=476).

FIG. 5D describes RNA Tagging identified transcriptome-wide Puf3p targets, specifically, proportional Venn diagram depicting the overlap between Puf3p targets identified by RNA Tagging versus those identified by other approaches (Gerber, et al., 2004 and Greeberg, et al., 2013).

FIG. 5E describes RNA Tagging identified transcriptome-wide Puf3p targets, specifically, plot of selected Go Term enrichments (1/P-value) of Puf3p targets identified by RNA Tagging, RIP-chip (Gerber, et al., 2004), and PAR-CLIP (Greeberg, et al., 2013). For simplicity, only 3 biological process terms are shown.

FIG. 5F describes RNA Tagging identified transcriptome-wide Puf3p targets, specifically, enriched sequence motifs, determined by MEME, in the 3' UTRs of Puf3p targets identified by RNA Tagging and RIP-chip (Gerber, et al., 2004), and in the PAR-CLIP peaks (Greeberg, et al., 2013). The numbers indicate the fraction of 3' UTRs in each set that contributed to the motif.

FIG. 6A describes Puf3p target classes correlated with in vitro binding affinity and in vivo regulation, specifically, heat map of clustered Puf3p targets, with Classes A (92 targets), B (189), and C (195) indicated. Each row in the heat map is an individual Puf3p target, and the colors indicate the number of TRPM detected with U-tags of at least the indicated number of uridines (columns). The highest ranked target is at the top of the heat map, and the lowest ranked target is at the bottom. The binding elements enriched in each of the Puf3p target classes are indicated. TRPM, Tagged RNAs per million uniquely mapped reads. PBE, Puf3p-binding element.

FIG. 6B describes Puf3p target classes correlated with in vitro binding affinity and in vivo regulation, specifically, plot of the median rank of Puf3p targets that contain six distinct binding elements relative to the published in vitro binding affinity ($K_d$) of purified Puf3p for the same sequences (Zhu, et al., 2009). Pearson's (r) and Spearman's ($\rho$) correlation coefficients and associated P-values (P) are indicated (r=0.98, P=0.0009; $\rho=0.94$, P=0.0048; n=6).

FIG. 6C describes Puf3p target classes correlated with in vitro binding affinity and in vivo regulation, specifically, enrichment of Puf3p target classes for mRNAs and proteins localized to mitochondria. Mitochondria-localized mRNAs and proteins were obtained from published experiments (Saint-Gerorges, et al., 2008 and Huh, et al., 2003).

FIG. 6D describes Puf3p target classes correlated with in vitro binding affinity and in vivo regulation, specifically, empirical cumulative distributions were plotted for all Puf3p targets (top) and the three Puf3p target classes (middle) relative to all mRNAs for the following attribute: enrichment for mRNAs bound by ribosomes at mitochondria (Williams, et al. 2014)(all mRNAs, n=6,094; Class A, n=92; Class B, n=189; Class C, n=194). The P-values from Kolmogorov-Smirnov (KS) tests comparing the different distributions are indicated (bottom).

FIG. 6E describes Puf3p target classes correlated with in vitro binding affinity and in vivo regulation, specifically, empirical cumulative distributions were plotted for all Puf3p targets (top) and the three Puf3p target classes (middle) relative to all mRNAs for the following attribute: change in mRNA abundance (Sun, et al., 2013) (all mRNAs, n=4,305; Class A, n=85; Class B, n=151; Class C, n=130) in puf3Δ relative to wild-type yeast. The P-values from Kolmogorov-Smirnov (KS) tests comparing the different distributions are indicated (bottom).

FIG. 6F describes Puf3p target classes correlated with in vitro binding affinity and in vivo regulation, specifically, empirical cumulative distributions were plotted for all Puf3p targets (top) and the three Puf3p target classes (middle) relative to all mRNAs for the following attributes: change in mRNA stability (Sun, et al., 2013) (all mRNAs, n=4,228; Class A, n=84; Class B, n=150; Class C, n=128) in puf3Δ relative to wild-type yeast. The P-values from Kolmogorov-Smirnov (KS) tests comparing the different distributions are indicated (bottom).

FIG. 7A describes RNA Tagging identified transcriptome-wide Bfr1p targets, specifically, enrichment of Tagged RNAs detected across different length U-tags in BFR1-PUP yeast relative to a control yeast strain (BY4742). Enrichment was calculated as a ratio of TRPMs obtained in strains with and without the BFR1-PUP chimera. TRPM, Tagged RNAs per million uniquely mapped reads.

FIG. 7B describes RNA Tagging identified transcriptome-wide Bfr1p targets, specifically, Tagged RNAs detected in the BFR1-PUP strain relative to the control strain (BY4742). Bfr1p target mRNAs are colored green while non-targets are grey.

FIG. 7C describes RNA Tagging identified transcriptome-wide Bfr1p targets, specifically, the number of Tagged RNAs detected for the 1,298 Bfr1p targets in three biological replicates. Spearman's correlation coefficient ($\rho$) is indicated (all pair-wise $\rho \geq 0.84$, P=0, n=1,298).

FIG. 7D describes RNA Tagging identified transcriptome-wide Bfr1p targets, specifically, proportional Venn diagram depicting the overlap between Bfr1p targets identified by RNA Tagging versus published RIP-chip targets (Hogan, et al., 2008).

FIG. 7E describes RNA Tagging identified transcriptome-wide Bfr1p targets, specifically, selected Go Term enrichments (1/P-value) of Bfr1p targets identified by RNA Tagging and RIP-chip.

FIG. 8A describes Bfr1p target classes correlated with membrane functions, specifically, a heat map of clustered Bfr1p targets, with Classes A (174 targets), B (297), C (566), and D (261) indicated. Each row in the heat map is an individual Bfr1p target, and the colors indicate the number of TRPM detected with U-tags of at least the indicated number of uridines (columns). The highest ranked target is at the top of the heat map, and the lowest ranked target is at the bottom. TRPM, Tagged RNAs per million uniquely mapped reads.

FIG. 8B describes Bfr1p target classes correlated with membrane functions, specifically, enrichment of Bfr1p target classes for mRNAs encoding proteins found in the secretome (Ast, et al., 2013).

FIG. 8C describes Bfr1p target classes correlated with membrane functions, specifically, enrichment of Bfr1p target classes for mRNAs encoding proteins with predicted transmembrane domains (TMD).

FIG. 8D describes Bfr1p target classes correlated with membrane functions, specifically, enrichments of Bfr1p target classes for mRNAs encoding proteins localized to the endoplasmic reticulum (ER).

FIG. 8E describes Bfr1p target classes correlated with membrane functions, specifically, enrichments of Bfr1p target classes for mRNAs found in P-bodies (Mitchell, et al., 2013).

FIG. 8F describes Bfr1p target classes correlated with membrane functions, specifically, empirical cumulative distributions were plotted for the indicated target sets (top) and the four Bfr1p target classes (middle) relative to all mRNAs for the following attribute: enrichment for mRNAs bound by ribosomes generally at the ER (all mRNAs, n=5,935; Class A, n=173; Class B, n=296; Class C, n=561; Class D, n=261), obtained from published ER-specific ribosome profiling (RP) experiments (Jan, et al., 2014). The P-values from Kolmogorov-Smirnov (KS) tests comparing the different distributions are indicated (bottom).

FIG. 8G describes Bfr1p target classes correlated with membrane functions, specifically, empirical cumulative distributions were plotted for the indicated target sets (top) and the four Bfr1p target classes (middle) relative to all mRNAs for the following attributes: enrichment for mRNAs bound by ribosomes at the SEC complex (all mRNAs, n=5,974; Class A, n=174; Class B, n=297; Class C, n=560; Class D, n=261), obtained from published ER-specific ribosome profiling (RP) experiments (Jan, et al., 2014). The P-values from Kolmogorov-Smirnov (KS) tests comparing the different distributions are indicated (bottom).

FIG. 8H describes Bfr1p target classes correlated with membrane functions, specifically, empirical cumulative distributions were plotted for the indicated target sets (top) and the four Bfr1p target classes (middle) relative to all mRNAs for the following attributes: enrichment for mRNAs bound by ribosomes at the SSH1 translocon complex (all mRNAs, n=5,785; Class A, n=174; Class B, n=297; Class C, n=561; Class D, n=260), obtained from published ER-specific ribosome profiling (RP) experiments (Jan, et al., 2014). The P-values from Kolmogorov-Smirnov (KS) tests comparing the different distributions are indicated (bottom).

FIG. 9A describes regulation versus sampling, specifically, schematic depicting relevant rates that contribute to the results obtained in an RNA Tagging experiment. RBP, RNA-binding protein. PUP, poly(U) polymerase. EP, effector protein.

FIG. 9B describes regulation versus sampling, specifically, consensus binding elements (as observed in the highest ranked targets) confer long interactions between RBP-PUP chimeras and relevant RNAs. This leads to more U-tags on target RNAs and allows sufficient time for regulation to be exerted by the effector protein in vivo.

FIG. 9C describes regulation versus sampling, specifically, degenerate (depicted) or occluded (not depicted) binding elements in targets lead to brief interactions with RBP-PUP, resulting in short U-tags and no regulation.

FIG. 10A describes RNA Tagging identified in vivo protein-RNA interactions, specifically, schematic of the RT-PCR assay for targeted RNA Tagging. The RT primers and PCR primer sets used in FIG. 10B and FIG. 10C are shown. PCR primer set 1 was two gene-specific primers and primer set 2 used a gene-specific forward primer and the U-select RT primer as the reverse PCR primer.

FIG. 10B describes RNA Tagging identified in vivo protein-RNA interactions, specifically, PUF3-PUP tagged HSP10 mRNA. Samples were run on the same gel and images were separated here for clarity. RT and PCR primers used in each column are indicated. "-RT" lanes (no reverse transcriptase) monitored genomic DNA contamination, which was minimal. "dT" lanes used the oligo(dT) primer, and illustrate that polyadenylated mRNA was present in all samples. "U-sel" lanes used the U-select primer, which detects RNAs with U-tags. The control strain (BY4742) lacked an RNA Tagging chimera. PUF3-PUP is the active RNA Tagging chimera and PUF3-PUPmut is a catalytically inactive chimera, which harbors active site mutations in the PUP (Asp185Ala, Asp187Ala).

FIG. 10C describes RNA Tagging identified in vivo protein-RNA interactions, specifically, PUF3-PUP tagged COX17 mRNA. Samples were run on the same gel and images were separated here for clarity. RT and PCR primers used in each column are indicated. "-RT" lanes (no reverse transcriptase) monitored genomic DNA contamination, which was minimal. "dT" lanes used the oligo(dT) primer, and illustrate that polyadenylated mRNA was present in all samples. "U-sel" lanes used the U-select primer, which detects RNAs with U-tags. The control strain (BY4742) lacked an RNA Tagging chimera. PUF3-PUP is the active RNA Tagging chimera.

FIG. 10D describes RNA Tagging identified in vivo protein-RNA interactions, specifically, representative Sanger sequencing results of tagged HSP10 mRNA. The PCR product from the U-select (U-sel) lane of the PUF3-PUP sample in FIG. 10B was cloned and individual colonies were sequenced. Black text indicates genomically encoded HSP10 3' UTR sequence, bold blue text indicates non-genomically encoded adenosines (the poly(A) tail), and bold red text indicates non-genomically encoded thymidines, which represent the 3' U-tag added by PUF3-PUP.

FIG. 10E describes RNA Tagging identified in vivo protein-RNA interactions, specifically, schematic of wild-type and mutant PHD1 strains. The two PUF-binding elements in PHD1 mRNA were disrupted via UGU to ACA substitutions in the endogenous PHD1 locus. Active or inactive (DD185/187AA) versions of PUP-2 were fused to the endogenous copy of PUF5 (PUF5-PUP and PUF5-PUPmutant, respectively) in the wild-type and mutant PHD1 strains.

FIG. 10F describes RNA Tagging identified in vivo protein-RNA interactions, specifically, PUF5-PUP tags PHD1 mRNA, which requires the (PUF binding element) PBEs. Samples were run on the same gel and images were separated here for clarity. RT and PCR primers used in each column are indicated. "-RT" lanes (no reverse transcriptase) monitored genomic DNA contamination, which was minimal. "dT" lanes used the oligo(dT) primer, and illustrate that polyadenylated mRNA was present in all samples. "U-sel" lanes used the U-select primer, which detects RNAs with U-tags. The control strain (BY4742) lacked an RNA Tagging chimera. PUF5-PUP is the active RNA Tagging chimera and PUF5-PUPmut is a catalytically inactive chimera, which harbors active site mutations in the PUP (Asp185Ala, Asp187Ala).

FIG. 11A illustrates high-throughput sequencing accurately detected U-tags of multiple lengths, specifically, synthetic libraries with various length U-tags, shown here as the reverse complement for clarity. The indicated libraries were paired-end sequenced on an Illumina HiSeq2500. The purple sequence represents the Illumina 5' adapter, the blue sequence represents a poly(A) tail of 12 nucleotides, the red sequence represents U-tags of multiple lengths, and the black sequence represents the U-select RT primer. The starred (*) position in the U0 library was further analyzed in FIG. 11B.

FIG. 11B illustrates high-throughput sequencing accurately detected U-tags of multiple lengths, specifically, accuracy of identifying Tagged RNAs by a single non-templated uridine. The percent nucleotide composition of position 13 in Read 2 of the U0 library, which corresponds to the starred (*) position in FIG. 11A, was plotted in a pie chart (n=310, 745). The actual bases detected by sequencing were reverse complemented here for clarity.

FIG. 12A is a comparison of Puf3p RNA Tagging results and RNA abundance, specifically, the mean number of Tagged RNAs detected for Puf3p targets was correlated with the mean length of their U-tag ($\rho$=0.5, P=0, n=476). Spearman's correlation coefficient ($\rho$) and associated P-value (P) are indicated. TRPM, Tagged RNAs Per Million uniquely mapped reads.

FIG. 12B is a comparison of Puf3p RNA Tagging results and RNA abundance, specifically, the mean number of Tagged RNAs (TRPM) detected for Puf3p targets was uncorrelated with their mean abundance (Spearman correlation, P>0.1). FPKM, fragments per kilobase of exon per million reads mapped.

FIG. 12C is a comparison of Puf3p RNA Tagging results and RNA abundance, specifically, the mean length of the U-tag on Puf3p targets was weakly correlated with their mean abundance (FPKM) ($\rho$=−0.37, P=0, n=476). Spearman's correlation coefficient ($\rho$) and associated P-value (P) are indicated.

Figure 13:
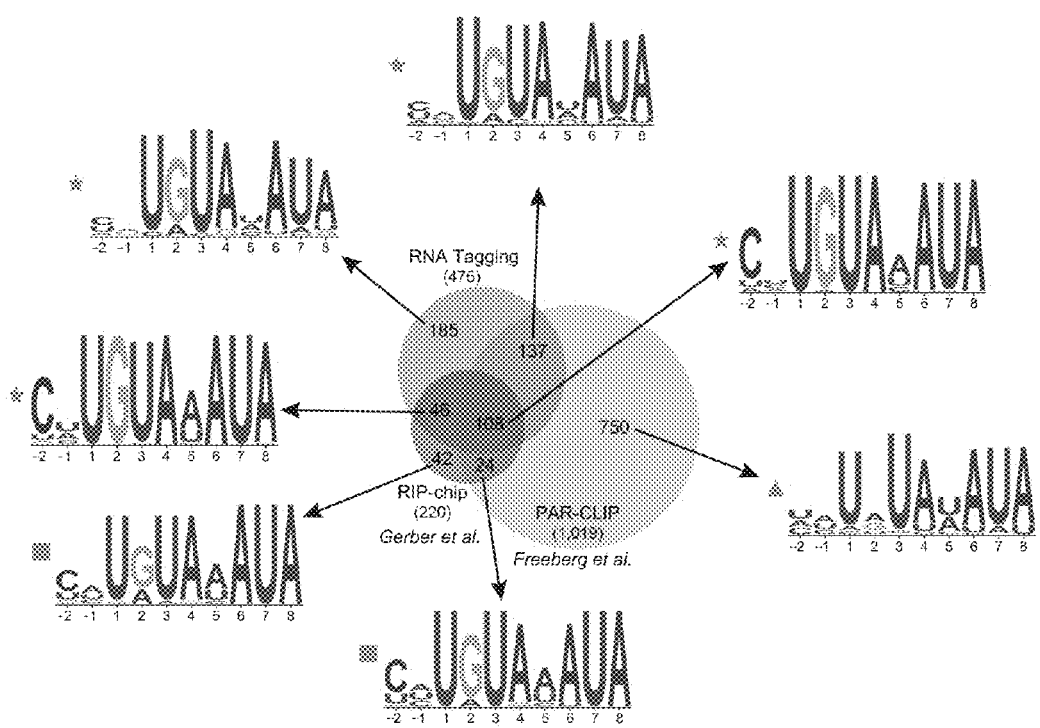

FIG. 13 describes Puf3p-binding element comparison between multiple methods. Proportional Venn diagram of Puf3p targets identified using RNA Tagging, RIP-chip (Gerber, et al., 2004), and PAR-CLIP (Freeberg, et al., 2013). The numbers indicate the number targets in each area of the plot. Position-weight matrices (plotted in bits) of the Puf3p-binding elements (PBEs) found in each group of targets are indicated. PBEs were derived as follows: PBEs with grey stars, MEME analysis of all RNA Tagging targets; PBEs with grey squares, MEME analysis of all RIP-chip targets; PBEs with grey triangles, PBEs in PAR-CLIP peaks.

Figure 14A:
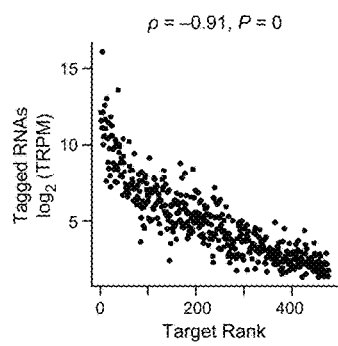

FIG. 14A describes Puf3p target rank was correlated with TRPM, specifically, the mean number of Tagged RNAs (TRPM) detected for Puf3p targets was correlated with their RNA Tagging rank ($\rho$=−0.91, P=0, n=476). Spearman's correlation coefficients ($\rho$) and associated P-values (P) are indicated. TRPM, Tagged RNAs Per Million uniquely mapped reads.

Figure 14B:
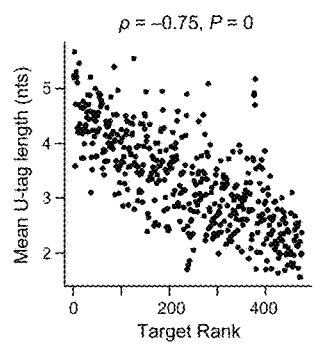

FIG. 14B describes Puf3p target rank was correlated with specifically, the RNA Tagging rank of Puf3p targets was correlated with the mean length of their U-tags ($\rho$=−0.75, P=0, n=476).

Figure 14C:
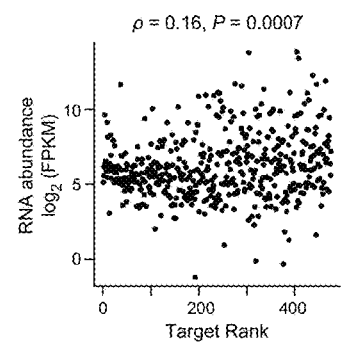

FIG. 14C describes Puf3p target rank was largely uncorrelated with RNA abundance, specifically, RNA Tagging rank of Puf3p targets was largely uncorrelated with their mean RNA abundance ($\rho$=0.16, P=0.0007, n=476). FPKM, fragments per kilobase of exon per million reads mapped.

Figure 15A:
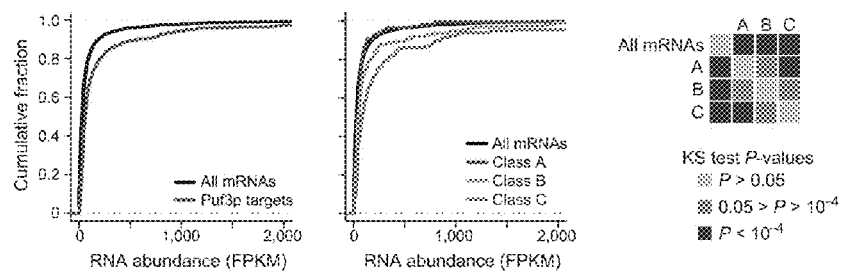

FIG. 15A is a comparison of RNA abundance and the position of binding elements across Puf3p targets, specifically, class C targets were the most abundant Puf3p targets. Empirical cumulative distributions of RNA abundance were plotted for all Puf3p targets (left) and the three Puf3p target classes (middle) relative to all mRNAs (all mRNAs, n=6, 595; Class A, n=92; Class B, n=189; Class C, n=195). The P-values from Kolmogorov-Smirnov (KS) tests comparing the different distributions are indicated (right).

Figure 15B:
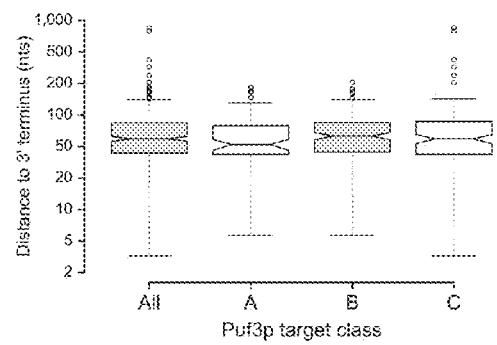

FIG. 15B is a comparison of RNA abundance and the position of binding elements across Puf3p targets, specifically, Puf3p-binding elements were similarly positioned in the 3' UTRs of each class of Puf3p targets relative to the 3' terminus. The distance from each binding element to the 3' terminus was calculated and plotted (all targets, n=404; Class A, n=90; Class B, n=169; Class C, n=145) (Tukey whiskers indicated). There were no statistical differences between any of the groups (Fisher-Pitman permutation tests, P>0.1).

Figure 15C:
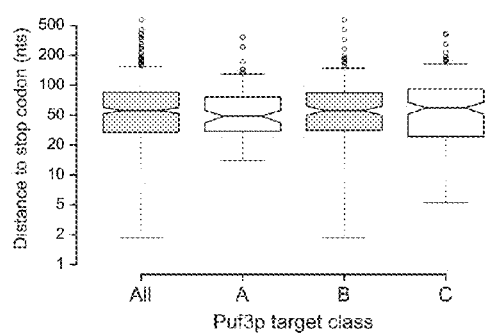

FIG. 15C is a comparison of RNA abundance and the position of binding elements across Puf3p targets, specifically, Puf3p-binding elements were similarly positioned in the 3' UTRs of each class of Puf3p targets relative to the stop codon. The distance from each binding element to the stop codon of the target was calculated and plotted (all targets, n=404; Class A, n=90; Class B, n=169; Class C, n=145) (Tukey whiskers indicated). There were no statistical differences between any of the groups (Fisher-Pitman permutation tests, P>0.1).

Figure 15D:
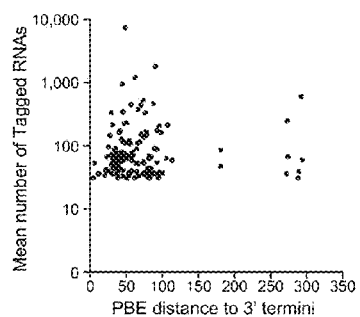

FIG. 15D is a comparison of RNA abundance and the position of binding elements across Puf3p targets, specifically, the mean number of Tagged RNAs detected for targets was compared to the distance from the PBE to the 3' terminus for isoforms of 64 Puf3p targets (143 distinct mRNAs) detected by at least 31 reads (24,417 reads total). No significant correlations were observed (Pearson and Spearman correlations, P>0.1).

Figure 15E:
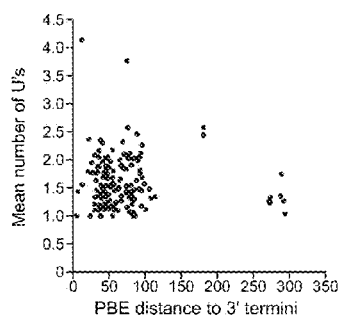

FIG. 15E is a comparison of RNA abundance and the position of binding elements across Puf3p targets, specifically, the mean number of U's detected for targets were compared to the distance from the PBE to the 3' terminus for isoforms of 64 Puf3p targets (143 distinct mRNAs) detected by at least 31 reads (24,417 reads total). No significant correlations were observed (Pearson and Spearman correlations, P>0.1).

FIG. 16A describes the number of Tagged RNAs and U-tag length was correlated with in vitro binding affinity, specifically, published in vitro binding affinity data of purified Puf3p for the six indicated RNA sequences was obtained and shown here (Zhu, et al., 2009).

Figure 16B:
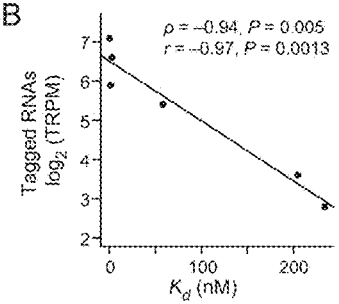

FIG. 16B describes the number of Tagged RNAs and U-tag length was correlated with in vitro binding affinity, specifically, the median number of Tagged RNAs detected (TRPM) (r=−0.97, P=0.0013; $\rho$=−0.94, P=0.005; n=6) was calculated and compared to the published in vitro binding affinity ($K_d$) of purified Puf3p for those sequences. Pearson's (r) and Spearman's ($\rho$) correlation coefficients and the associated P-values (P) are indicated. TRPM, Tagged RNAs Per Million uniquely mapped reads.

Figure 16C:
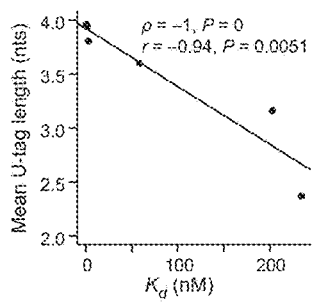

FIG. 16C describes the number of Tagged RNAs and U-tag length was correlated with in vitro binding affinity, specifically, the median U-tag length (r=−0.94, P=0.0051; $\rho$=−1, P=0; n=6) of Puf3p targets containing six distinct binding elements was calculated and compared to the published in vitro binding affinity ($K_d$) of purified Puf3p for those sequences. Pearson's (r) and Spearman's ($\rho$) correlation coefficients and the associated P-values (P) are indicated. TRPM, Tagged RNAs Per Million uniquely mapped reads.

Figure 17:
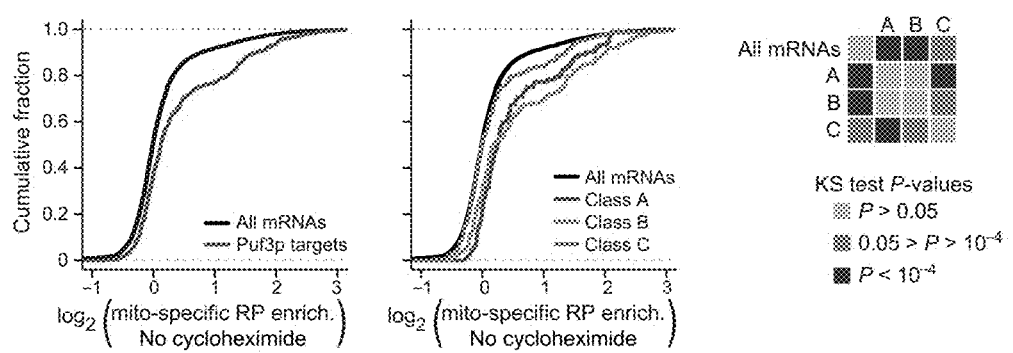

FIG. 17 illustrates Puf3p targets were enriched for mRNAs translated at mitochondria in the absence of cycloheximide. Published mitochondria-specific ribosome profiling (RP) data in the absence of cycloheximide was mined (Williams, et al., 2014). Empirical cumulative distributions were plotted for all Puf3p targets (left) and the Puf3p target classes (middle) relative to all mRNAs (all mRNAs, n=5,609; Class A, n=92; Class B, n=188; Class C, n=193). The P-values from Kolmogorov-Smirnov (KS) tests that compared the different distributions are indicated (right).

FIG. 18 describes mRNAs with known PUF3-dependent half-lives were Class A or B targets. Summary of published RNA half-lives of the indicated genes in wild-type and puf3Δ strains (Miller, et al., 2014). Puf3p target class, RNA Tagging rank, and Puf3p-binding elements are indicated. "NA" indicates the gene was not identified as a Puf3p target by RNA Tagging.

Figure 19A:
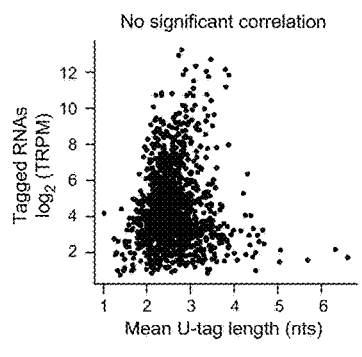

FIG. 19A is a comparison of Bfr1p RNA Tagging results and RNA abundance, specifically, the mean number of Tagged RNAs (TRPM) detected and the mean length of their U-tag were uncorrelated (Spearman correlation, P>0.1). TRPM, Tagged RNAs Per Million uniquely mapped reads.

Figure 19B:
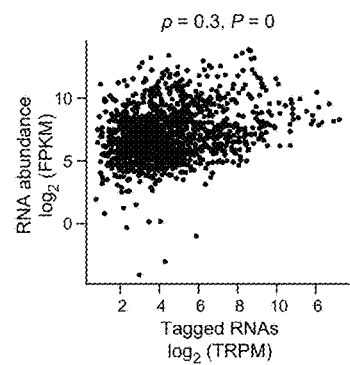

FIG. 19B is a comparison of Bfr1p RNA Tagging results and RNA abundance, specifically, the mean number of Tagged RNAs (TRPM) detected for Bfr1p targets was weakly correlated with their mean abundance ($\rho$=0.3, P=0; n=1,298). FPKM, fragments per kilobase of exon per million reads mapped. Spearman's correlation coefficient ($\rho$) and associated P-value (P) are indicated.

Figure 19C:
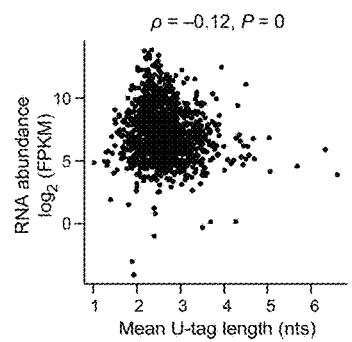

FIG. 19C is a comparison of Bfr1p RNA Tagging results and RNA abundance, specifically, the mean length of the U-tag on Bfr1p targets was largely uncorrelated with their mean abundance ($\rho$=−0.12, P=0; n=1,298). Spearman's correlation coefficient ($\rho$) and associated P-value (P) are indicated.

Figure 20:
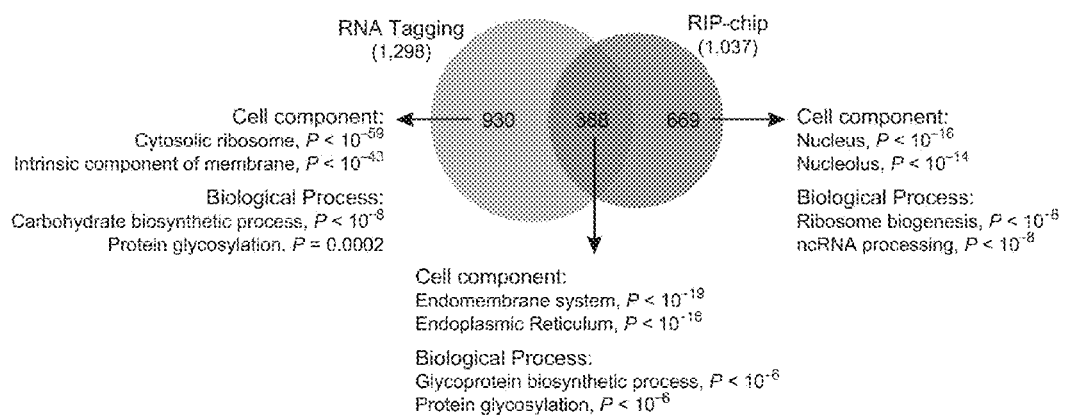

FIG. 20 Bfr1p targets identified by both RNA Tagging and RIP-chip (Hogan, et al., 2008) were enriched for membrane-associated functions. Proportional Venn diagram of Bfr1p targets identified using RNA Tagging and RIP-chip (Hogan, et al., 2008). GO analyses were performed on the three groups and enrichments for representative terms from Biological Process and Cellular Component ontologies are indicated.

Figure 21A:
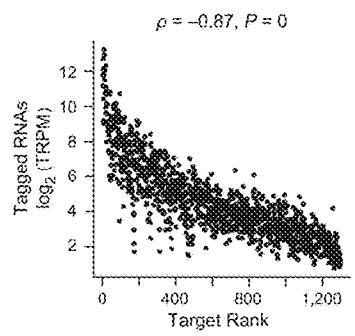

FIG. 21A describes Bfr1p target rank was correlated with TRPM and was very weakly correlated with U-tag length and RNA abundance, specifically, the mean number of Tagged RNAs (TRPM) detected for Bfr1p targets was correlated with their RNA Tagging rank ($\rho$=−0.87, P=0; n=1,298). Spearman's correlation coefficients ($\rho$) and associated P-values (P) are indicated. TRPM, Tagged RNAs Per Million uniquely mapped reads.

Figure 21B:
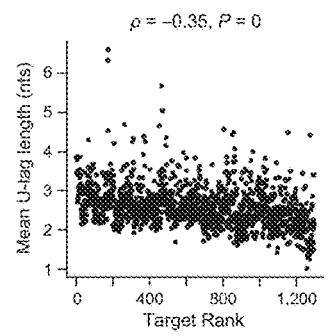

FIG. 21B describes Bfr1p target rank was correlated with TRPM and was very weakly correlated with U-tag length and RNA abundance, specifically, the RNA Tagging rank of Bfr1p targets was weakly correlated with the mean length of their U-tags ($\rho$=−0.35, P=0; n=1,298).

Figure 21C:
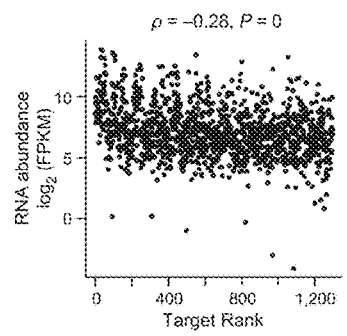

FIG. 21C describes Bfr1p target rank was correlated with TRPM and was very weakly correlated with U-tag length and RNA abundance, specifically, RNA Tagging rank of Bfr1p targets was weakly correlated with their mean RNA abundance ($\rho$=−0.28, P=0; n=1,298). FPKM, fragments per kilobase of exon per million reads mapped.

Figure 22:
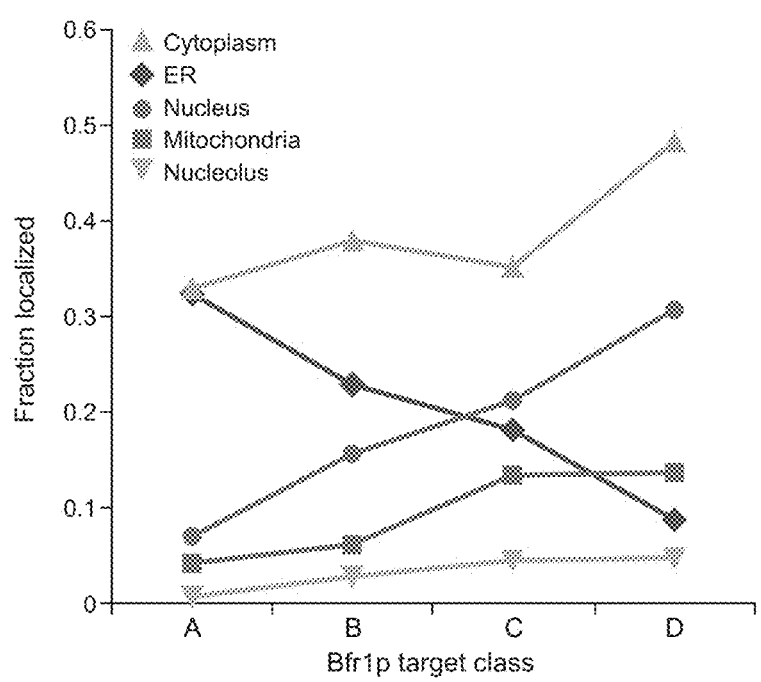

FIG. 22 describes Bfr1p target class was correlated with protein localization to the ER. The fraction of each class of Bfr1p targets that are localized to the cytoplasm, endoplasmic reticulum (ER), nucleus, mitochondria, and nucleolus, obtained from the yeast GFP database (Huh, et al., 2003), was plotted. Classes A-C of Bfr1p targets were highly enriched for ER-localized proteins (hypergeometric tests, $P<1\times10^{-16}$), and the enrichment progressively decreased from Class A to D targets. No other significant enrichments were observed (hypergeometric tests, P>0.01).

Figure 23:
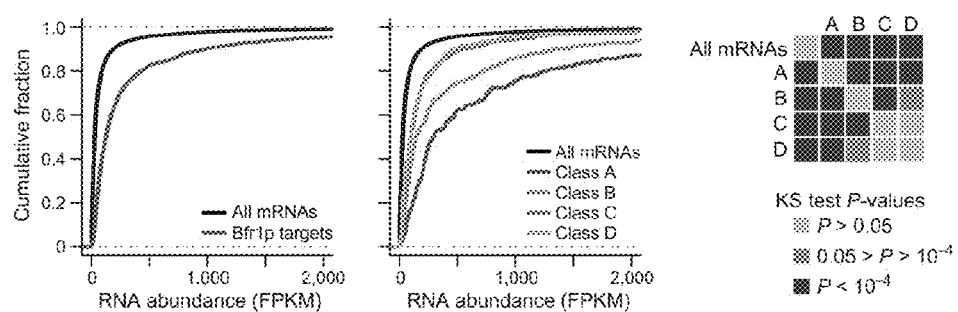

FIG. 23 describes Bfr1p targets were highly enriched for abundant mRNAs. Empirical cumulative distributions of RNA abundance (FPKM) were plotted for all Bfr1p targets (left) and the Bfr1p target classes (middle) relative to all mRNAs (all mRNAs, n=6,595; Class A, n=174; Class B, n=297; Class C, n=564; Class D, n=261). The P-values from Kolmogorov-Smirnov (KS) tests comparing the different distributions are indicated (right). Class A Bfr1p targets were most enriched for abundant RNAs and the enrichment progressively decreased to Class C and D targets. FPKM, fragments per kilobase of exon per million reads mapped.

Figure 24A:
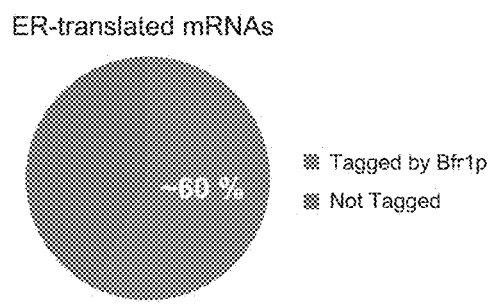

FIG. 24A illustrates Bfr1p bound abundant, ER-translated mRNAs, specifically, plot of the fraction of ER-translated mRNAs (>2-fold enrichment, n=736), obtained from a published ER-specific ribosome profiling experiment (Jan, et al., 2014) ($\log_2$ (ubc6.7mchx) enrichment), that were tagged by Bfr1p (422 mRNAs).

Figure 24B:
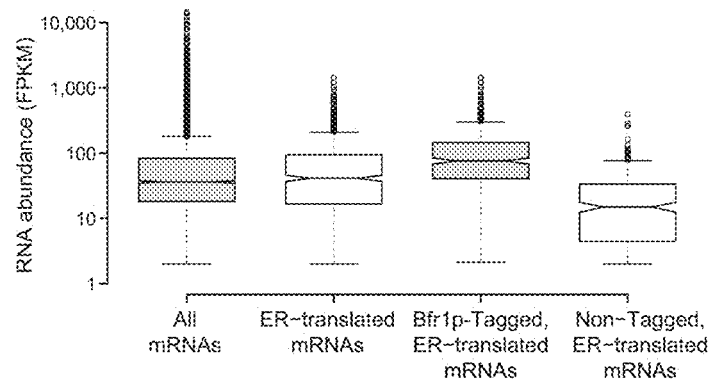

FIG. 24B illustrates Bfr1p bound abundant, ER-translated mRNAs, specifically, plots of the RNA abundance (FPKM) of the indicated groups of mRNAs (Tukey whiskers indicated). Of the mRNAs specifically, translated at the ER, those tagged by Bfr1p were significantly more abundant than those not tagged by Bfr1p (Fisher-Pitman permutation test, $P<10^{-6}$). FPKM, fragments per kilobase of exon per million reads mapped.

FIG. 25A is a schematic of a tethered function assay and downstream analyses in which *S. pombe* SPAC1093.04 poly(C) polymerase is expressed in budding yeast and activity is measured on a reporter tRNA.

FIG. 25B is a graph of the results of a tethered function assay with SPAC1093.04, with the nucleotide composition of the population of tail sequences at each length versus unique tails.

FIG. 25C shows the most abundant tail sequences resulting from SPAC1093.04 activity on the reporter tRNA.

DETAILED DESCRIPTION OF THE INVENTION

In General

In one embodiment, the present invention is a new approach to identify any RNAs bound by any protein. In a preferred embodiment, one would create a fusion protein comprising a protein of interest fused to a tagging domain (preferably the terminal uridylyl transferase PUP-2) which lacks RNA-binding domains of its own. When the fusion protein binds RNA, the tagging domain adds a tag to the bound RNA. One can identify and isolate the tagged RNA.

In a preferred embodiment, PUP-2 adds uridines in the bound RNA, thus yielding an identifiable "U-tag" on all bound RNAs. U-tagged RNAs may be identified by simply extracting and sequencing the RNA. This approach works remarkably well in both *Xenopus* and yeast, as the Examples below demonstrate that RBP/PUP-2 chimeras deposit U-tags on known and predicted targets of the RBPs.

When coupled with high-throughput sequencing, the RNA Tagging of the present invention allows the simultaneous identification of all RNAs bound by particular RBPs in both in vivo and in vitro situations.

In order to extend RNA Tagging to a genome-wide method, the present invention also provides a sample preparation protocol which involves, in general, the following steps: 1) isolate RNA, preferably total RNA, 2) enrich the targeted RNA population, 3) attach 3' and 5' adapters, 4) PCR amplify libraries, 5) sequence, and 6) identify tagged RNAs. It is noted that the sample preparation protocol of the present invention is useful for the RNA Tagging protocol of the present invention and is also generally applicable to any experimenter who wishes to identify the 3' terminal nucleotides on any non-ribosomal RNA.

Definitions

As used herein, "tagging" refers to the addition of one or more nucleotides to the 3' end or the 5' end of a nucleic acid molecule or the covalent modification of one or more nucleotides of a nucleic acid molecule.

As used herein, "3' tagging" refers to the addition of one or more nucleotides to the 3' end of a nucleic acid molecule.

As used herein, "selective tagging" refers to addition of one or more nucleotides to the 3' end or the 5' end of one or more specific nucleic acid molecules of interest or the covalent modification of one or more nucleotides of one or more specific nucleic acid molecules of interest.

As used herein, "selective(ly) 3' tagging" refers to the addition of one or more nucleotides to the 3' end of one or more specific nucleic acid molecules of interest.

As used herein, "in vitro tailing" refers to the addition of one or more nucleotides to the 3' or 5' end of all members of a population of nucleic acid molecules.

As used herein, "U-tag(ing)" refers to one or more uridines added to the 3' end of one or more specific nucleic acid molecules of interest by a selective tagging enzyme.

Methods of the Present Invention

The present invention provides a method for determining a binding affinity between any protein and a particular RNA sequence. Determining a binding affinity should be interpreted broadly to include instances where a numerical $K_d$ is not calculated, such as estimating a relative binding affinity between two proteins and a particular RNA sequence, and the like. The method typically comprises contacting an RNA population with a fusion protein comprising the protein of interest and a tagging domain. The tagging domain will introduce a 3' tag onto RNAs to which the fusion protein selectively binds (the "bound RNA"). One would identify RNAs comprising the 3' tag, typically by measuring the length or presence of the 3' tag on the bound RNAs and determining the binding affinity by analyzing this result.

This disclosure also provides a method for identifying, among a total RNA of a cell of interest, any RNA to which any protein of interest selectively binds in a cellular environment of a cell of interest. The method typically comprises expressing a fusion protein (as described above) within a cellular environment, wherein the tagging domain introduces a 3' tag to the RNA to which the fusion protein selectively binds. One would then isolate RNA from the cell, resulting in isolated total RNA. To analyze non-rRNA and non-tRNA RNAs (e.g. mRNAs), one would preferably deplete rRNA and tRNA from the isolated sample, resulting in rRNA/tRNA-depleted isolated total RNA. One then attaches a tail sequence in vitro to the 3' end of the isolated total RNA or the rRNA/tRNA-depleted isolated total RNA resulting in tailed total RNA. One then selectively reverse transcribes the tailed total RNA using a primer having a sequence that is complementary to at least part of the tag sequence and at least part of the tail sequence, resulting in a single-stranded cDNA complementary to RNA including the 3' tag and the tail. One may synthesize a cDNA strand complementary to the single-stranded cDNA resulting in a double stranded cDNA and amplify the double-stranded cDNA. One would then typically purify the amplified double-stranded cDNA, typically resulting in a more purified cDNA, and sequence the purified cDNA.

Referring to FIG. 1, a schematic view of one aspect of the invention is shown where an RNA-binding protein and poly(U) polymerase (RBP/PUP) fusion protein is expressed in cells, the RBP/PUP fusion protein selectively tags RNAs to which the fusion protein is selectively bound with 3' terminal uridines, and the tagged RNAs are identified by RT-PCR or sequencing.

As described above, the fusion protein includes a protein of interest. The protein of interest can be a protein with either a known or an unknown affinity to certain RNAs and is not limited by any functional or structural definition. The protein of interest can exhibit specific or non-specific binding.

In certain embodiments, the protein of interest can be a member of the PUF protein family. Examples of a protein of interest can include, but are not limited to, S. cerevisiae PUF1, PUF2, PUF3, PUF4, PUF5, PUF6, IMD2, IMD3, IMD4, PIN4, VTS1, BFR1, EAP1, CCR4, LSM proteins, TOR, MS2 coat protein, S. pombe PUF1, PUF2, PUF3, PUF4, and PUF5, H. sapiens PUM1, PUM2, CPEB, AGO1, AGO2, AGO3, AGO4, DCR1, DROSHA, APC, FMRP, and FUS, M. musculus PUM1, PUM2, CPEB, AGO1, AGO2, AGO3, AGO4, DCR1, DROSHA, APC, FMRP, and FUS, C. elegans FBF1, FBF2, PUF3, PUF4, PUF5, PUF6, PUF7, PUF8, PUF9, PUF10, and PUF11, D. melanogaster FBF1, FBF2, PUF3, PUF4, PUF5, PUF6, PUF7, PUF8, PUF9, PUF10, and PUF11, D. pumilio FBF1, FBF2, PUF3, PUF4, PUF5, PUF6, PUF7, PUF8, PUF9, PUF10, and PUF11, X. laevis PUM1 and PUM2, X. tropicalis PUM1 and PUM2, and the like.

As described above, the fusion protein includes a tagging domain. In certain embodiments, the tagging domain can comprise poly(U) polymerases, such as C. elegans poly(U) polymerase (PUP-2), S. pombe CID1, TUT7 homologs, or TUT4 homologs, among others; RNA methyltransferases, such as H. sapiens METTL3, M. musculus METTL3, or S. cerevisiae IME4, among others; RNA-specific adenosine deaminases (ADARs), such as C. elegans ADR-1 or ADR-2, among others; CC-adding enzymes, such as D. radiodurans DR-1, among others; RNA pseudouridylation enzymes, such as C. elegans PUS-1 or H. sapiens PUS7, among others; and the like. The Examples below disclose a suitable enzyme, SPAC1093.04.

The tagging domain can have a specific activity and a non-specific activity. The specific activity can involve adding a 3' tag to RNA to which the fusion protein is bound. The non-specific activity can involve adding a 3' tag to RNA to which the fusion protein is not bound. In certain embodiments, excellent results are achieved when the specific activity is as high as possible and the non-specific activity is as low as possible. However, certain applications may benefit from deployment of a tagging domain having somewhat higher non-specific activity. The specific versus non-specific activity can be quantified by comparing the length of a 3' tag for a tethered versus untethered enzyme.

As an example, referring to Lapointe, et al. 2013, the non-specific activity of XTUT7 is ~10% of the level of its specific activity, because the U-tail added by the untethered enzyme is ~10% of the U-tail added by the tethered enzyme. Using this quantification, a tagging enzyme having ~0% non-specific activity is preferred for an experiment focusing on specific tagging, a tagging enzyme having ~10-50% may be preferred for less specific applications, and a tagging enzyme having >50% non-specific activity may be preferred for subcellular localization experiments. It should be apparent that modifications can be made to individual enzymes to optimize the non-specific activity level. As shown in Lapointe, et al. 2013, an enzyme with non-specific activity can be engineered to lack non-specific activity. Similarly, a completely specific tagging enzyme (e.g., PUP-2) could be engineered to gain non-specific activity, for example, by fusing non-specific RNA-binding domains to the protein.

The tagging domain requires careful selection and it was surprisingly discovered that certain tagging domains exhibited significantly more specific tagging activity and significantly less non-specific tagging activity when compared with others. For example, PUP-2 exhibited significantly more specific tagging activity than Saccharomyces cerevisiae TRM8 or TRM10. For example, PUP-2 exhibited less non-specific tagging activity than Xenopus laevis poly(U) polymerase, XTUT7. A person having ordinary skill in the art should be able to run suitable assays to determine the specific and non-specific tagging activity and make determinations regarding the suitability of the tagging domain as a result.

In certain embodiments, the 3' tag can include unmodified nucleotides. In certain embodiments, the 3' tag can include uridine, polyuridine, adenosine, polyadenosine, guanosine, polyguanosine, cytidine, or polycytidine. In certain embodiments, the 3' tag can include uridine or polyuridine.

In certain embodiments, the 3' tag can include modified nucleotides. Many modified nucleotide analogs exist and have proven useful for many biological and biochemical applications. The descriptions herein focus on uridine analogs, but many of the modifications described herein are available for the other nucleotides.

To increase the likelihood of success of incorporating modified nucleotides, it can be advantageous to first turn off transcription in the cells of interest using techniques known to those having ordinary skill in the art. Then, the modified nucleotides can be introduced to the cells. Because modified nucleotides are readily incorporated into RNA by RNA polymerases, it can be advantageous to inhibit the endogenous polymerases to ensure that the modified nucleotides are only incorporated into RNA by the tagging domain of the fusion protein.

What follows is a non-limiting list of possible uses of modified nucleotides. There are many other types of nucleotide analogs available with many other uses than those described herein.

First, introducing thio-uridine analogs into cells prior to an RNA Tagging experiment would allow more stringent purification of Tagged RNAs. This would be useful for those interested in RNAs that are difficult to highly purify from cells. For example, 4-Thiouridine-5'-Triphosphate could be introduced into cells of interest. The Tagging Enzyme, if the tagging enzyme is a PUP, would then Tag RNAs with the thio-uridine analogs. These analogs are then easily converted in vitro to biotinlyated uridine using standard techniques. After the conversion, the Tagged RNAs would have a biotin group in the Tag sequence, which allows stringent purification of the Tagged RNAs using the streptavidin-biotin interaction.

Second, introducing fluorescently labeled nucleotide analogs would allow easy visualization of where actively Tagged RNAs are located in the cell. For example, 2'-Fluoro-2'-deoxyuridine-5'-Triphosphate could be introduced to cells, and the incorporation of the fluorescent nucleotide by the Tagging enzyme into bound RNAs could be monitored in real-time using standard microscopy techniques.

Third, CLICK-functionalized nucleotide analogs (available commercially from Jena Bioscience, Jena, Germany) could also be used. These are nucleotides that have highly reactive groups attached to them that enable easy attachment of other molecules. For example, the nucleotides enable the easy attachment of biotin or a fluorescent group to the modified nucleotide. This class of analog allows both of the experiments described above.

Fourth, biologically relevant nucleotide analogs could be used. In this experiment, one would be interested in what happens to RNAs when particular modified nucleotides are added to them. For example, pseudouridylation is an emerging form of RNA regulation (Carlile, et al., 2014). Adding pseudouridine-5'-Triphosphate nucleotides to cells, and using a Tagging enzyme that can incorporate this modified nucleotide would provide an easy way to incorporate the modified nucleotide onto particular RNAs. One could then probe the biological outcome of having the modified nucleotide on the RNAs of interest. Other types of modifications to RNA bases are emerging and could be subjected to similar analyses.

The fusion proteins described herein can be prepared by fusing the tagging domain to the C-terminus or the N-terminus of the protein of interest, preferably via recombinant DNA techniques.

For example, in preparing an RBP/PUP-2 fusion protein for X. laevis, PUP2 was cloned downstream of the open reading frame (ORF) for the RNA-binding domain of PUM1. The resulting clone was then in vitro transcribed, and the mRNA encoding the fusion protein was microinjected into X. laevis stage VI oocytes. As another example, in preparing an RBP/PUP-2 fusion protein for S. cerevisiae, a stable yeast strain was engineered. The engineered strain included a DNA sequence for the PUF3/PUP-2 fusion protein replacing the endogenous genomic copy of PUF3. A base plasmid was constructed that could be used to create stable RNA Tagging strains for any protein of interest. The plasmid contains the ORF of C. elegans PUP-2, followed by the in-frame DNA sequence of a 3-hemaglutinin (3HA) epitope tag, followed by the DNA sequence for the URA3 yeast marker.

This base plasmid may be used to create stable strains in at least two ways. First, the PUP-2/3HA/URA3 sequence can be PCR amplified using primers that contain 5' and 3' flanking sequences homologous to the gene of interest. The PCR product can then be transformed and homologously recombined into the yeast genome. Alternatively, larger 5' and 3' flanking regions to the gene of interest can be cloned into the base plasmid, which can then be PCR amplified and transformed into yeast. The latter approach provides more efficient homologous recombination but is slower.

The present invention may include a means for expressing a fusion protein within the cellular environment. This expression means can include methods known to those having ordinary skill in the art. In certain embodiments, the means can include an mRNA that encodes the expression of the fusion protein that is suitable for microinjection into a cell of interest, a plasmid or other vector coding expression of the fusion protein that is suitable for insertion into the DNA of a cell of interest, a purified recombinant protein injected into a cell, clustered regularly interspaced short palindromic repeat (CRISPR) associated (CRISPR-CAS) ready DNA, stable cell-lines or strains containing the plasmid of the fusion protein without requiring genomic integration (i.e., transfections in cell lines), or a combination thereof.

Methods of expressing a fusion protein within the cellular environment can include many methods known to those having ordinary skill in the art. In certain embodiments, the expression can include microinjecting an mRNA encoding the expression of the fusion protein into a cell of interest, inserting a plasmid or other vector encoding expression of the fusion protein into the cell of interest, or a combination thereof. In embodiments where the means of expressing or the expressing step include a plasmid, the plasmid can include a DNA sequence encoding expression of the fusion protein and the plasmid can be adapted for insertion into the DNA of the cell of interest at a position where it replaces the exogenous DNA coding the protein of interest. In certain embodiments, the plasmid can be created using a base plasmid or vector that includes coding for the tagging domain.

In one embodiment of the present invention, multiple, non-identical fusion proteins are expressed. In one embodiment, the non-identical fusion proteins differ in the tagging domain. In another embodiment, the non-identical fusion proteins differ in the protein of interest.

RNA Tagging Sample Preparation Protocol (SPP)

In certain embodiments, the methods disclosed herein can include isolating a total RNA from the cell of interest. For example, see th examples below for a preferred protocol.

In certain embodiments, isolating a total RNA from the cell of interest can include a TRI Reagent™ Solution Protocol or the like. Briefly, the TRI Reagent™ Solution Protocol can include the following steps: "1) Homogenize tissue samples in 10-20 volumes TRI Reagent solution. Homogenize cultured cells in 1 mL TRI Reagent solution per $5-10 \times 10^6$ cells, or per 10 $cm^2$ culture dish area; 2) Incubate the homogenate for 5 min at room temp. 3) (Optional) Centrifuge at 12,000×g for 10 min at 4° C. and transfer the supernatant to a fresh tube; 4) Add 100 µL [chloroform] per 1 mL of TRI Reagent solution, mix well, and incubate at room temp for 5-15 min; 5) Centrifuge at 12,000×g for 10-15 min at 4° C., then transfer the aqueous phase to a fresh tube; 6) Add 500 µl of isopropanol per 1 mL of TRI Reagent solution, vortex for 5-10 sec, and incubate at room temp for 5-10 min; 7) Centrifuge at 12,000×g for 8 min at 4-25° C., and discard the supernatant; 8) Add 1 mL of 75% ethanol per 1 mL of TRI Reagent solution; 9) Centrifuge at 7500×g for 5 min, remove the ethanol, and briefly air dry the RNA pellet; and 10) Dissolve RNA in the buffer of your choice." TRI Reagent™ Solution Protocol Manual 9738M Revision D, Revision Date Aug. 30, 2010. The specific means of isolating the total RNA from the cell of interest is not intended to be limiting to the invention.

In certain embodiments, the methods can include poly(A) selecting the isolated total RNA. In certain embodiments, poly(A) selecting the isolated total RNA can include using Dynabeads™ mRNA Purification Kit (Life Technologies).

In certain embodiments, the methods include depleting rRNA and tRNA from a total RNA sample. In certain embodiments, depleting rRNA and tRNA from the total RNA sample can include using a RiboZeroGold™ kit (Epicentre) and clean-up beads (Agencourt), or the like. The specific means of depleting rRNA and tRNA is not intended to be limiting to the invention.

In certain embodiments, the methods disclosed herein can include in vitro tailing an RNA population.

Suitable means for in vitro tailing an RNA population include using a poly(A) polymerase that can be brought into contact with an RNA sample to add a 3' G/I tail to the RNA sample.

In certain embodiments, the methods disclosed herein can include selectively reverse transcribing the in vitro tailed RNA using a primer having a sequence that is complementary to at least part of the tail sequence. In certain embodiments, the primer has a sequence that is complementary to at least part of the tail sequence and/or the 3' tag. In certain embodiments, the primer can be an oligo-(dT), an oligo-(dA), a $C_9A_n$ primer (such as $C_9A_3$ the $A_3$ U-select oligo), or a $C_n$ G-select oligo. In certain embodiments, the primer can include an adapter primer, such as an Illumine™ primer, on its 5' end for the purpose of selectively binding, PCR enriching, or multiplexing the cDNA produced by the reverse transcription. The reverse transcription can be carried out by methods known to those of skill in the art, such as thermal cycling, and the like.

In certain embodiments, the methods disclosed herein include synthesizing a cDNA strand complementary to the single-stranded cDNA (from the RT) resulting in a dsDNA. This step can be carried out by methods known to those of skill in the art.

In certain embodiments, the methods disclosed herein can include cleaning the dsDNA. Cleaning the dsDNA can include using the RNA Clean XP™ beads (Agencourt). In certain embodiments, the dsDNA can be cleaned more than once, including, but not limited to, twice sequentially, three times sequentially, four times sequentially, or more times sequentially. The ratio between RNA Clean XP™ beads and dsDNA can be optimized according to methods known to those having ordinary skill in the art. In certain embodiments, the RNA Clean XP™ beads can be used at a ratio (beads:sample) of between about 0.4:1 and about 2:1. In certain embodiments, the ratio can be about 0.8:1.

In certain embodiments, the methods disclosed herein can include amplifying the dsDNA. This step can be carried out by methods known to those of skill in the art.

In certain embodiments, the methods disclosed herein include purifying the dsDNA. This step can be carried out by methods known to those of skill in the art, including methods utilizing a GeneJet PCR Purification Kit™ (Thermo Fisher Scientific) or methods utilizing RNA Clean XP™ beads (Agencourt).

In certain embodiments, the methods disclosed herein include sequencing the purified dsDNA. This step can be carried out by methods known to those of skill in the art.

The RNA Tagging Sample Preparation Protocol (SPP) of the present invention can be used to conduct a genome-wide approach to the methods described herein. The goal of the SPP is to create a DNA library of RNAs and their 3' terminal nucleotides that is ready for high-throughput sequencing, for example on the Illumine™ platforms. The SPP is ligation- and digestion-free and is highly adaptable as a result, which makes it an improvement on recently developed protocols. (Chang, et al., 2014 and Subtelney, et al., 2014).

The SPP enables the sequencing and identification of 3' non-templated nucleotides on RNA (FIG. 4B). In the Example depicted in FIG. 4B, rRNAs and tRNAs are depleted using the RiboZeroGold™ kit (Epicentre) and clean-up beads (Agencourt). Second, the remaining RNAs are G/I-tailed by yeast poly(A) polymerase, which both captures the 3' terminal nucleotides on the RNA and serves as the 3' adapter for subsequent steps. Small amounts of inosine are included to prevent the formation of troublesome G-quadruplexes. Third, tagged RNAs are selectively reverse transcribed using the U-select oligo, which contains the standard Illumine™ RT primer followed by $C_9A_n$. Fourth, the enriched cDNA pool is converted into dsDNA using an oligo containing the Illumine™ 5' adapter followed by six random nucleotides and Exo-Klenow DNA polymerase. Fifth, the dsDNA pool is PCR amplified and bar-coded using the now attached 5' and 3' adapters. Sixth, the PCR products are size-selected by gel purification. Finally, the DNA library is paired-end sequenced on an Illumine™ platform.

Features of the RNA Tagging SPP are the selective RT step using the U-select oligo and its applicability to multiple biological questions. In developing the SPP, one of our goals was to selectively sequence tagged RNAs. The U-select oligo facilitates this since it optimally base-pairs only with RNAs that end in uridines (FIG. 4B). Thus, tagged RNAs are more efficiently reverse-transcribed and consequently become enriched in the cDNA pool. Typically, a $C_9A_3$ oligo is used, but the $A_n$ portion of the oligo can be lengthened or shortened to provide stronger or weaker selection, respectively.

Alternatively, the $A_n$ can be changed to a different nucleotide to enrich RNAs that end in a different nucleotide. For example, if a user is interested in detecting RNAs that end in G's, the user would change the $A_n$ portion of the U-select oligo to $C_n$ to create a G-select oligo. While this disclosure describes use of the RNA Tagging SPP in the context of RNA Tagging, it is also readily applicable to detecting endogenous RNAs that end in particular nucleotides. For example, there is emerging evidence that mRNAs in human cells are 3' terminally oligo-uridylated and mono- or di-guanylated (Chang, et al, 2014). The RNA Tagging SPP is an alternate approach to detecting and identifying these RNAs.

Comparison to Prior Techniques

Referring to FIG. 2, the present invention (RNA Tagging) may offer several advantages over the established techniques of RNA immunoprecipitation followed by sequencing (RIP-seq) and crosslinking immunoprecipitation followed by sequencing (CLIP-seq). See, McHugh, et al., 2014. First, certain embodiments of RNA Tagging are remarkably simple and fast, as the technique only requires high-throughput sequencing and bioinformatic analyses of RNA extracted from cells that express the RBP-PUP fusion protein. RIP-seq and CLIP-seq require highly purified RNA-protein complexes isolated from cells prior to any sequencing and bioinformatic analyses. CLIP-seq also requires crosslinking and additional purification steps that improves its reliability and usefulness, but increases the complexity of and time required to do an experiment.

Second, certain embodiments of RNA Tagging are very reliable. RNA Tagging utilizes denaturing conditions when isolating RNA from cells, which ensures that RNAs are only tagged in intact, live cells. RIP-seq is susceptible to detecting artifactual RNA-protein interactions, since cells must be lysed in native conditions. CLIP-seq, due to its in vivo cross-linking and highly stringent purifications, does offer highly reliable results, although the advantage is at the cost of slow and complex experiments.

Third, RNA Tagging may require very little cell input. In yeast, and certain embodiments of RNA Tagging, 25 mL of mid-log-phase cultures provides enough RNA to perform 20 RNA Tagging experiments. As a comparison, RIP-seq and CLIP-seq experiments require liters of mid-log-phase yeast for a single experiment.

Fourth, certain embodiments of RNA Tagging allow the unbiased determination of the binding element for a particular protein. Similar to RNA-seq, the sequences of tagged genes typically contain highly enriched sequence motifs, as identified by unbiased motif searching algorithms, which represent the in vivo binding specificity of the assayed protein. CLIP-seq utilizes an RNase footprinting step to considerably reduce the sequence space that must be analyzed, which greatly facilitates binding element determination.

Fifth, certain embodiments of RNA Tagging provide genome-wide, in vivo binding affinity comparisons for a protein on particular RNA sequences. In PUF3 RNA Tagging, there is a strong positive correlation of the in vitro binding affinity of PUF3 for a particular sequence and the length of the U-tail on the RNA that contains the sequence. To date, RIP-seq and CLIP-seq experiments have failed to yield similar insight.

Sixth, RNA Tagging is typically less expensive than CLIP-seq since it doesn't require costly radioactively labeled nucleotides.

Seventh, RNA Tagging is high-throughput amenable. RNA Tagging experiments can be done for a single protein in hundreds of conditions simultaneously, since single experiments theoretically require as little as 1 mL of yeast culture. Similarly, RNA Tagging experiments can be done with hundreds of proteins simultaneously for the same reason. Thus, RNA Tagging offers several considerable advantages over available techniques.

Applications of RNA Tagging

Figure 3:
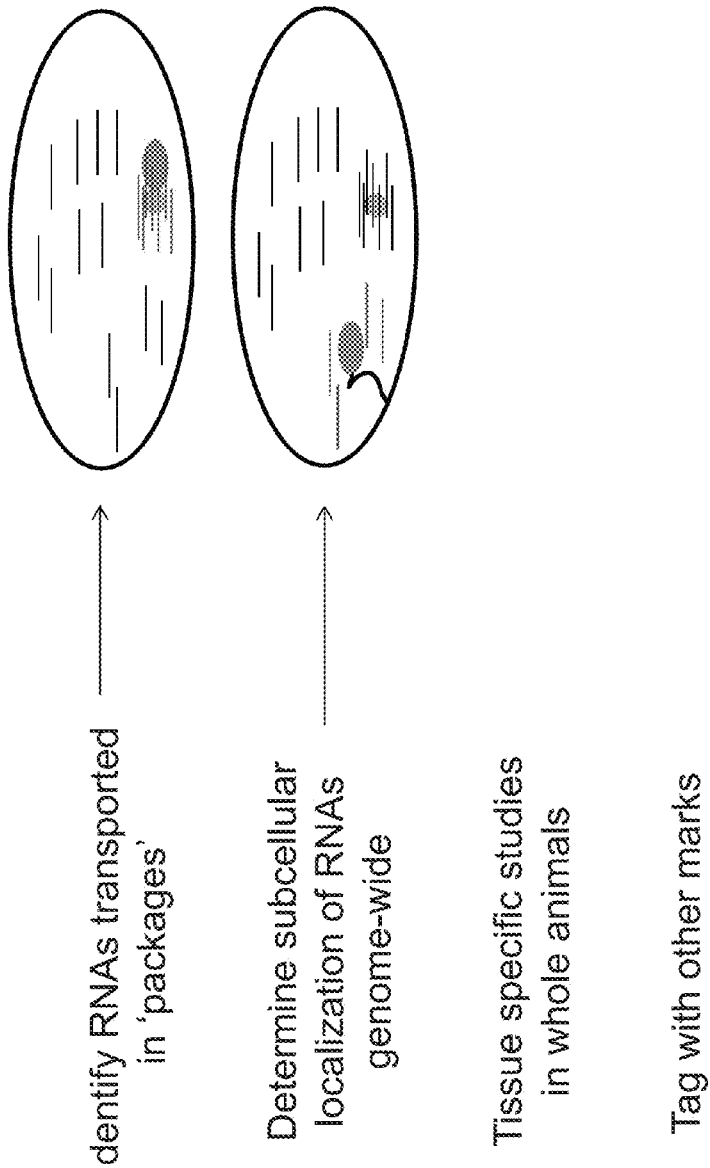
FIG. 3 shows example applications of the methods disclosed herein.

Referring to FIG. 3, the kits, compositions of matter, and methods described herein have many applications to biological problems that are currently difficult or nearly impossible to assay. First, as demonstrated by the genome-wide RNA Tagging experiments described herein, RNA Tagging is easily implemented on a genome-wide scale to identify the RNAs bound by a protein in vivo. For example, due to its rapidity and simplicity, RNA Tagging could be used to interrogate how the RNA targets of a protein change in different conditions or in response to different stresses. In addition, RNA Tagging could be used to quickly identify the targets of many different proteins.

Second, RNA Tagging can be used to identify RNAs that are co-transported or co-localized in a cell, which is an important yet difficult to assay problem. By using a less specific tagging domain, RNAs that are associated with a particular protein, but not directly bound by it, could be identified.

Third, RNA Tagging can be used to determine the genome-wide sub-cellular localization of RNAs. For example, by anchoring a PUP to the mitochondria, all the RNAs that are transported and localized to the mitochondria will be tagged and thus identified.

Fourth, RNA Tagging could be used to perform tissue-specific studies in live animals. For example, a vital biological question is how the RNA targets of a protein change from tissue to tissue in animals. Current techniques that rely on cross-linking are often impossible to perform, since the tissue in the live animal is inaccessible to UV light, or not ideal, since the tissue must be removed from the live animal for cross-linking. By tissue-specifically, expressing an RBP/PUP fusion protein, one can determine the tissue-specific binding profile of a given protein without any of the above problems or limitations.

Fifth, RNA Tagging can be employed using a tagging enzyme that adds a different tag, such as cytidine. With two or more distinct tags, it would be possible to probe how multiple proteins exchange on their RNA targets. For example, yeast PUF4 and PUF5 share RNA targets but it is currently unclear if their binding is exclusive (one but not the other), shared (both at the same time), or ordered (one then the other). RNA Tagging is well-suited to probe this important question.

Kits of the Present Invention

This disclosure provides a kit for identifying, among a total non-ribosomal, non-transfer RNA of a cell of interest, RNAs to which a protein of interest selectively bind in a cellular environment of the cell of interest. The kit can include one or more of the following: (1) a means of expressing a fusion protein within the cellular environment, the fusion protein comprising the protein of interest and a tagging domain fused to the RNA binding protein of interest, the fusion protein selectively 3' tagging the RNA to which the protein of interest selectively bind with a selective tag (2) a means of in vitro tailing an RNA population with a non-selective tag having a non-selective sequence; and (3) a primer having a sequence that is complementary to at least part of the selective sequence.

This disclosure also provides a method of selectively sequencing a sub-selection of a total RNA population. The method can include one or more of the following: selectively 3' tagging the sub-selection with a selective tag having a selective sequence; in vitro tailing the total RNA population with a non-selective tag having a non-selective sequence; selectively reverse transcribing the sub-selection using a primer having a sequence that is complementary to at least part of the selective sequence and at least part of the non-selective sequence to produce cDNA complementary to the sub-selection; and sequencing a double-stranded cDNA containing the cDNA complementary to the sub-selection.

Compositions of Matter of the Present Invention

This disclosure provides a composition of matter that includes a cell comprising a fusion protein as described herein. In certain embodiments, the tagging domain of the fusion protein is PUP-2.

EXAMPLES

Example 1. Protein-RNA Networks Revealed Through Covalent RNA Marks

Protein-RNA networks are ubiquitous and central in biological control. We present an approach, termed "RNA Tagging," that identifies protein-RNA interactions in vivo by analyzing purified cellular RNA, without protein purification or crosslinking. An RNA-binding protein of interest is fused to an enzyme that adds uridines to the end of RNA. RNA targets bound by the chimeric protein in vivo are covalently marked with uridines and subsequently identified from extracted RNA using high-throughput sequencing. We used this approach to identify hundreds of RNAs bound by a *Saccharomyces cerevisiae* PUF protein, Puf3p. The method revealed that while RNA-binding proteins productively bind specific RNAs to control their function, they also "sample" RNAs without exerting a regulatory effect. We exploited the method to uncover hundreds of new and likely regulated targets for a protein without canonical RNA-binding domains, Bfr1p. The RNA Tagging approach is well-suited to detect and analyze protein-RNA networks in vivo.

Introduction.

Proteins bind to and regulate RNAs, governing RNA processing, transport, translation, and decay. A single protein can bind and control hundreds of RNAs, while a single RNA molecule may be bound by many proteins. These protein-RNA networks are essential, and their misregulation can lead to defects in cell function and human disease. Global mapping of protein-RNA interactions across the proteome and transcriptome is thus a central goal.

Over the last decade, powerful RNA immunoprecipitation-based approaches have made it possible to identify RNAs bound by a specific protein (McHugh, et al., 2014). In RNA immunoprecipitation (RIP), RNA-binding proteins are immunopurified from cell lysates, and associated RNAs are identified by microarray or deep sequencing (Tenenbaum, et al., 2000 and Zhao, et al. 2010). UV-crosslinking prior to immunoprecipitation (CLIP) covalently links interacting proteins and RNAs, which facilitates their purification (Ule, et al., 2003; Licatalosi, et al., 2008; Hafner, et al., 2010; Konig, et al., 2010). CLIP also employs a partial RNase digestion of bound RNA to determine global binding sites for particular proteins (Licatalosi, et al., 2008; Hafner, et al., 2010; Konig, et al., 2010).

Despite their utility and strength, RIP and CLIP approaches have limitations. Protein-RNA complexes must be purified from cell lysates using antibodies directed to endogenous or epitope-tagged proteins. RIP, which requires native conditions, is susceptible to non-physiological interactions in vitro (Mill, et al., 2004; Riley, et al., 2012; Riley, et al., 2013). In CLIP, UV-crosslinking is relatively inefficient or requires nucleotide analogs to enhance efficiency (Hafner, et al., 2010; Darnell, 2010; Fecko, et al., 2007). CLIP also requires numerous enzymatic steps. Moreover, since transient interactions are permanently captured by crosslinking, biologically meaningful interactions are difficult to distinguish from those that are not (Riley, et al., 2013).

We sought a method to identify global protein-RNA interactions in vivo, in which interactions were unambiguous and must have occurred inside the cell. The approach we report here, termed "RNA Tagging", does so and is independent of protein purification, crosslinking, or radioactive-labeling steps. We use the approach to identify RNAs bound by two *Saccharomyces cerevisiae* proteins, Puf3p and Bfr1p. Our studies show that Puf3p "samples" certain RNAs unproductively—without exerting regulation—while at the same time binding productively to others, eliciting a biological outcome. Analysis of Bfr1p reveals a role for this non-canonical RNA-binding protein in the regulation of mRNAs translated at the endoplasmic reticulum.

Results.

The RNA Tagging Approach.

To detect and probe protein-RNA interactions in vivo, we developed a new approach, termed "RNA Tagging". The key principle of the method is that binding of a protein to an RNA in vivo leaves a covalent mark on the RNA, which is subsequently detected in vitro. In its simplest application, an RNA-binding protein (RBP) is fused to the *Caenorhabditis elegans* poly(U) polymerase, PUP-2 (FIG. 4A). This enzyme lacks RNA-binding domains and therefore does not uridylate RNA efficiently on its own, unlike other proteins in the family (Lapointe, et al., 2013 and Kim, et al., 2015). As a result, the chimeric protein covalently "tags" only the RNAs to which the RBP binds. Tagged RNAs, bearing varied numbers of uridines (the "U-tag"), are identified from the pool of total RNA using targeted or high-throughput sequencing assays, facilitated by a reverse-transcription step that is selective for uridylated RNAs (FIG. 4B).

Targeted Detection of RNA Tagging.

We first implemented RNA Tagging in *S. cerevisiae* and focused on the PUF protein, Puf3p. This protein recognizes a well-defined sequence in hundreds of mRNA targets important for mitochondrial functions (Gerber, et al., 2004; Zhu, et al., 2009; Olivas, et al., 2000; Saint-Georges, et al., 2008; Gadir, et al., 2011; Chatenay-Lapointe, et al., 2011; Garcia-Rodriguez, et al., 2007). To create the RNA Tagging chimera, termed "PUF3-PUP", we inserted the pup-2 open reading frame downstream of PUF3 at its native locus in the *S. cerevisiae* genome.

We initially examined tagging of two known targets of Puf3p: HSP10 and COX17 mRNA (Gerber, et al., 2004 and Olivas, et al., 2000). We grew strains that expressed wild-type and mutant PUF3-PUP chimeras to mid-log phase and lysed cells under denaturing conditions. We next performed parallel RT-PCR assays on HSP10 and COX17 mRNA (FIG. 10A). PUF3-PUP deposited U-tags on both mRNAs (FIGS. 10B and 10C). A primer selective for uridylated RNAs (U-select primer) yielded prominent PCR products only in cells that expressed the wild-type chimeric protein. As controls, a primer selective for polyadenylated RNAs detected the mRNAs in all samples, and a mutant chimera with a catalytically inactive PUP failed to tag HSP10. The presence of the U-tag on HSP10 mRNA was confirmed by directed sequencing (FIG. 10D). Similarly, a PUF5-PUP2 chimera added U's to endogenous, wild-type PHD1 mRNA, a known target (Wilinski, et al., 2015), but not to the same mRNA with mutant binding elements, which was confirmed by deep sequencing as described below (FIGS. 10E and 10F). Thus, RNA Tagging identified protein-RNA interactions that occurred in the cell.

Transcriptome-Wide RNA Tagging.

To implement RNA Tagging transcriptome-wide, we developed a new method to identify 3' terminal nucleotides on RNA. We grew yeast strains that expressed PUF3-PUP to mid-log phase and isolated RNA (FIG. 4A). We then enriched mRNAs and added 3' terminal G/I nucleotides to serve as a 3' adapter (G/I-tailing) (Kusov, et al., 2001) (FIG. 4B). Inosines were included to reduce the stability of potential G-quadruplexes (Lane, et al., 2008). Next, we reverse-transcribed the G/I-tailed RNA using the U-select primer, synthesized the second strand of DNA, PCR amplified the dsDNA, and size-selected the PCR products using Solid Phase Reversible Immobilization [SPRI] beads. DNA libraries were paired-end sequenced on an Illumina HiSeq 2500 instrument.

Tagged RNAs were identified using a computational approach. We used the first sequencing read (Read 1) to assign reads to particular genes, and we used the second sequencing read (Read 2) to identify the 3' terminal nucleotides (FIGS. 4C and 4D). RNAs with U-tags, termed "Tagged RNAs", were defined as RNAs that ended in at least eight adenosines not encoded in the genome (the poly(A) tail), followed by at least one uridine not encoded in the genome or the U-select primer. To ensure U-tags of various lengths were accurately detected, we sequenced synthetic DNA libraries with known numbers of uridines. The libraries contained the adapter sequences, a poly(A)$_{12}$ tail, and variable length U-tags (FIG. 11). The synthetic U-tags were accurately measured and readily distinguished (FIG. 4E).

RNA Tagging Identified Global Puf3p Targets.

Analysis of the PUF3-PUP tagging strain yielded a set of Tagged RNAs. Of the approximately ten million reads, about 50% aligned to a single location in the yeast genome ("uniquely mapped"). We detected just over one million Tagged RNAs, which corresponded to approximately 175,000 Tagged RNAs Per Million uniquely mapped reads ("TRPM"). Tagged RNAs had U-tags that ranged from one to more than ten nucleotides in length, and U-tags of all lengths were enriched approximately 500- to 1,800-fold in the PUF3-PUP strain relative to a control strain (FIG. 5A).

As assessed by RNA Tagging, Puf3p bound hundreds of RNAs in vivo. Of the RNAs detected with 3' uridines in the PUF3-PUP strain, 476 mRNAs were enriched above background in two biological replicates and were termed "Puf3p targets" (see Methods) (FIG. 5B). The number of TRPM detected for each Puf3p target was highly reproducible ($\rho=0.93$, P=0) (FIG. 5C). TRPM was moderately correlated with the mean U-tag length ($\rho=0.5$, P=0) and not correlated with RNA abundance (FIGS. 12A and 12B). The number of U's in the U-tag was weakly and inversely correlated with RNA abundance ($\rho=-0.37$, P=0) (FIG. 12C). The set of RNA Tagging targets significantly overlapped with those identified by RIP-chip (Gerber, et al., 2004) and PAR-CLIP (Freeberg, et al., 2013) (hypergeometric tests, all P<$2.2\times10^{-16}$) (FIG. 5D). Furthermore, Gene Ontology (GO) analyses revealed that Puf3p targets were greatly enriched for mitochondrial functions, similar to the previously identified targets (FIG. 5E).

Puf3p targets identified by RNA Tagging were highly enriched for Puf3p-binding elements. Using the unbiased algorithm Multiple Em for Motif Elicitation (MEME) (Bailey, 1994), we determined that Puf3p targets identified by RNA Tagging were highly enriched for Puf3-binding elements in their 3' UTRs (FIG. 5F). Importantly, Puf3p tagged approximately 70% (170/246) of mRNAs with the consensus sequence CHUGUAHAUA (SEQ ID NO:1) in their 3' UTRs, which represents the highest-affinity Puf3p-binding elements (Zhu, et al., 2009). The binding element present in targets identified by RNA Tagging was similar to the one identified in the RIP-chip targets, while the PAR-CLIP targets yielded a more degenerate element (FIG. 5F and FIG. 13).

The above data demonstrate that RNA Tagging globally identifies protein-RNA interactions in vivo. The approach reproducibly identified over four hundred mRNAs bound by Puf3p in the cell, and these were highly enriched for the expected mitochondrial functions and Puf3p-binding elements.

RNA Tagging and Binding Affinity.

We hypothesized that RNA Tagging might reveal the relative affinities of Puf3p for its different targets in the cell. For example, high-affinity targets would have relatively long interactions with PUF3-PUP, providing ample time for long U-tags to be added to the RNA. In contrast, low-affinity targets would have relatively brief interactions with PUF3-PUP, resulting in shorter U-tags.

To test this hypothesis, we employed a two-dimensional ranking of Puf3p targets uniquely enabled by the RNA Tagging approach. Targets have two attributes—the number of Tagged RNAs detected and the number of U's added. Based on these two parameters, we hierarchically clustered Puf3p targets by the number of Tagged RNAs detected at increasing U-tag lengths. Clustering results were visualized by a heat map, with the highest ranked target at the top (FIG. 6A). As expected, target rank was strongly correlated to TRPM ($\rho=-0.91$, $P=0$) and U-tag length ($\rho=-0.75$, $P=0$) (FIGS. 14A and 14B). Target rank was largely uncorrelated with RNA abundance (FIG. 14C).

Puf3p targets are a continuum, but to facilitate downstream analyses, we separated them into three distinct groups, referred to as classes. Puf3p target classes were defined using the dendrogram from the clustering analysis and sequential statistical analyses (see Methods). Class A Puf3p targets, which consist of the highest ranked genes, had the most TRPM detected and the longest U-tags (FIG. 6A). They possessed nearly perfect Puf3p-binding elements in their 3' UTRs (FIG. 6A), dramatically exemplified by the cytosine enrichment at the −2 position, which enhances Puf3p binding in vitro and PUF3-dependent regulation in vivo (Zhu, et al., 2009 and Miller, et al., 2014). In contrast, Class C was the lowest ranked group, and these targets had the least TRPM and shortest U-tags. Class C targets contained degenerate binding elements in their 3' UTRs (FIG. 6A) and were expressed more highly than Class A or B targets (FIG. 15A). They also lacked enriched Puf3p-binding elements in their 5' UTRs or open reading frames, which agrees well with the propensity of PUF proteins to bind 3' UTRs (Gerber, et al., 2004; Wilinski, et al., 2015; Wickens, et al., 2002; Hogan, et al., 2008). The average position of the binding elements in the 3' UTRs of targets was nearly identical across classes (FIGS. 15B and 15C). Similarly, the number of Tagged RNAs and the number of U's detected on target RNAs were uncorrelated with the distance from the binding element to the 3' terminus of the transcripts (FIGS. 15D and 15E).

The rank of targets correlated well with their measured binding affinities in vitro. We compared the median RNA Tagging rank of targets with six specific binding elements to the in vitro binding affinities of purified Puf3p for those same sequences (Zhu, et al., 2009) (FIG. 16A). Median target rank correlated well with $K_d$ ($r=0.98$, $P=0.0009$; $\rho=0.94$, $P=0.0048$) (FIG. 6B). Similarly, $K_d$ was correlated with TRPM and U-tag length (FIGS. 16B and 16C). Comparisons of $K_d$ to RNA abundance and the distances from binding elements to 3' termini or stop codons yielded no significant correlations. Randomized data also yielded no significant correlations for any of the above analyses.

These findings support the hypothesis that RNA Tagging reveals high- and low-affinity targets in vivo. This is demonstrated by the co-variation of target rank (and hence classes) with the quality of Puf3p-binding elements and with binding affinity measured in vitro.

RNA Tagging Distinguished Regulation from "Sampling".

We next examined the relationship between affinity and in vivo regulation. Puf3p is required for localization of specific mRNAs to mitochondria (Saint-Georges, et al., 2008 and Gadir, et al., 2011) and regulates mitochondrial function (Chatenay-Lapointe, et al., 2011 and Garcia-Rodriguez, et al., 2007). Puf3p also destabilizes some of its target mRNAs (Zhu, et al., 2009; Olivas, et al., 2000; Miller, et al., 2014; Jackson, et al., 2004; Houshmandi, et al., 2005). We hypothesized that Class A Puf3p targets, which were the best detected RNA Tagging targets and bound with the highest affinities, would exhibit the greatest enrichment for mitochondrial association as well as PUF3-dependent stability, while Class C targets would exhibit the least.

Puf3p target classes correlated with localized translation at mitochondria. We mined published data that identified mRNAs (Saint-Georges, et al., 2008) and proteins (Huh, et al., 2003) localized to mitochondria. Class A Puf3p targets were significantly enriched for mRNAs and proteins localized to mitochondria (hypergeometric tests, all $P<2.2\times10^{-16}$) (FIG. 6C). Enrichments steadily decreased from Class A to Class C targets. We also mined recently published data that identified mRNAs translated by ribosomes localized to the outer mitochondrial surface, captured through proximity-specific ribosome profiling (Williams, et al., 2014). Puf3p targets were significantly enriched for mRNAs translated at mitochondria (Kolmogorov-Smirnov tests, all $P<2.2\times10^{-16}$) (FIG. 6D). Notably, Classes A and B were highly enriched while Class C was weakly enriched. Trends were similar without the translation inhibitor cycloheximide, which confirmed that Puf3p targets are actively translated at mitochondria (FIG. 17).

Puf3p target classes correlated with sensitivity to deletion of PUF3. We next mined published microarray experiments that measured global changes in mRNA abundance and decay rate in wild-type and puf3Δ strains (Sun, et al., 2013). Puf3p targets identified by RNA Tagging were significantly more abundant and more stable in the puf3Δ strain relative to all mRNAs (Kolmogorov-Smirnov tests, all $P<2.2\times10^{-16}$) (FIGS. 6E and 6F). Enrichments for both abundance and stability progressively decreased across Puf3p target classes, with Class A targets exhibiting the greatest effects. Importantly, Class C targets were hardly enriched for the effects of PUF3 on either their abundance or stability. All specific mRNAs previously shown to be stabilized in a puf3Δ strain were Class A or B targets, which independently corroborated our meta-analysis of the global experiments (Miller, et al., 2014) (FIG. 18).

The correlation between Puf3p target classes and known Puf3p biological functions, as well as with binding affinity, suggests that the highest ranked Puf3p RNA Tagging targets are those that are bound and regulated in vivo. In contrast, the lowest ranked targets are bound very weakly. The fact that these RNAs (Class C) were tagged indicates they were bound; yet, they were largely unregulated. We refer to this behavior as "sampling." We define the term "sampling" to mean that the protein bound to RNA sufficiently long to tag it, but insufficiently long to exert its regulatory effect—likely too brief to recruit effector proteins or allow them to act.

RNA Tagging Identified Global Bfr1p Targets.

We next implemented RNA Tagging to analyze Bfr1p, which lacks canonical RNA-binding domains. Bfr1p is implicated in the secretory pathway (Jackson, et al., 1994 and Trautwein, et al., 2004) and is localized to the endoplasmic reticulum (ER) under normal conditions (Lang, et al., 2001 and Weidner, et al., 2014) and P-bodies after stress (Simpson, et al., 2014). Bfr1p was also found associated with over a thousand mRNAs by RIP-chip (Hogan, et al., 2008). Intriguingly, its reported mRNA targets were not enriched for those with a role in the secretory pathway.

RNA Tagging with BFR1-PUP identified more than a thousand functionally enriched Tagged RNAs. As with Puf3p, Tagged RNAs were highly enriched over many U-tag lengths (FIG. 7A). In the BFR1-PUP strain, 1,296 mRNAs and two snoRNAs (snR11 and snR31) were detected above background in three biological replicates and were termed "Bfr1p targets" (FIG. 7B). TRPMs were reproducibly detected across replicates (all pair-wise $\rho \geq 0.84$) (FIG. 7C). TRPM, U-tag length, and RNA abundance were all largely uncorrelated (FIG. 19). Approximately 30% of the targets were previously identified by RIP-chip (Hogan, et al., 2008), which represents a significant overlap (hypergeometric test, $P<2.2\times10^{-16}$) (FIG. 7D). Unlike Puf3p, Bfr1p targets identified by RNA Tagging lacked a defined binding element.

As determined by GO analyses, RNA Tagging targets were much more functionally enriched than those identified by RIP-chip. RNA Tagging targets were greatly enriched for cytoplasmic translation and membrane-associated functions while RIP-chip targets were at most weakly enriched (FIG. 7E). Deeper dissection revealed that targets uniquely identified by RNA Tagging, as well as those identified by both RNA Tagging and RIP-chip, were similarly enriched for membrane-associated functions and the term "cytoplasmic translation", which predominately encompasses ribosomal proteins (FIG. 20). In contrast, mRNAs uniquely identified by RIP-chip were enriched for ribosome biogenesis and the processing of ncRNAs.

Bfr1p Binds mRNAs Translated at the ER.

To more closely examine Bfr1p targets, we performed a two-dimensional analysis with Bfr1p targets as we had with Puf3p. Bfr1p targets were grouped into four classes, Classes A to D, with Class A again containing the highest ranked targets (FIG. 8A). Target rank was strongly correlated with TRPM ($\rho=-0.87$, $P=0$), while target rank was weakly correlated with the average number of U's in the U-tag and RNA abundance (FIG. 21). The weak correlation between target rank and the number of U's in the U-tag indicated that in this case, unlike that of Puf3p, target rank was driven by TRPM.

The highest ranked Bfr1p targets were the most enriched for membrane-related functions. By mining published data, we found that Class A targets were significantly enriched for proteins that are secreted (Ast, et al., 2013), predicted to have a transmembrane domain, and localized to the ER (Huh, et al., 2003) (hypergeometric tests, all $P<2.2\times10^{-16}$) (FIGS. 8B, 8C and 8D). Enrichments progressively decreased from Class A to Class D targets. Furthermore, Class A Bfr1p targets were the least enriched for mRNAs that encode proteins localized to the nucleus, nucleolus, and mitochondria (Huh, et al., 2003) (FIG. 22). These enrichments progressively increased across classes to levels near those expected by random chance. Bfr1p targets were also highly enriched for mRNAs found in P-bodies (Mitchell, et al., 2013) (hypergeometric test, $P<2.2\times10^{-16}$) (FIG. 8E). The enrichment progressively decreased from Class A to Class C targets, but then slightly increased for Class D targets.

The localization of Bfr1p to the ER (Lang, et al., 2001 and Weidner, et al., 2014), its presence on polysomes (Lang, et al., 2001), and the enrichment of its best targets for membrane-related proteins suggested that many of its targets would be translated at the ER. To test this, we mined recently published data that identified ribosome-occupied mRNAs specifically, localized at the ER, captured by a proximity-specific ribosome profiling experiment (Jan, et al., 2014).

Bfr1p targets were highly enriched for abundant, ER-translated mRNAs. In comparison to all mRNAs, Bfr1p targets were significantly enriched for ER-localized translation, in contrast to Bfr1p targets identified by RIP-chip (Kolmogorov-Smirnov tests, all $P<2.2\times10^{-16}$) (FIG. 8F). The enrichment of ER-localized translation progressively decreased from Class A to Class D targets. Bfr1p targets were similarly enriched for both SEC complex-dependent and SEC complex-independent translocation events (Kolmogorov-Smirnov tests, all $P<2.2\times10^{-16}$) (FIGS. 8G and 8H). Class A Bfr1p targets were also most enriched for abundant mRNAs, and the enrichment progressively decreased across classes (FIG. 23). Bfr1p bound about 60% of the approximately 700 mRNAs enriched for ER-localized translation, and the Bfr1p-bound mRNAs were significantly more abundant than those not bound by Bfr1p (Fisher-Pitman permutation test, $P<10^{-6}$) (FIG. 24).

Our findings illustrate that Bfr1p preferentially binds mRNAs that encode ribosomal and membrane-associated proteins, many of which are translated at the ER. These data clarify seemingly contradictory reports of Bfr1p function in vivo (see Discussion).

Discussion.

RNA Tagging identifies targets of RNA-binding proteins in vivo, relying solely on the covalent marks left on the RNA. The approach is facile, reproducible, sensitive, and well-suited to analyze RNA-regulatory networks in vivo. The method only requires the generation and expression of relevant chimeric proteins, which is straightforward in most model systems, especially given recent advances in genome engineering. In organisms with endogenous enzymes that add and remove uridines, endogenous uridylated mRNAs are sufficiently stable to be detected (Munoz-Tello, et al., 2015; Norbury, 2013; Chang, et al., 2014; Newman, et al., 2011) and can be accounted for computationally using the same approach as described here. RNA Tagging is adaptable to specific cell types and tissues of living animals, as it requires minimal starting material and only purified RNA.

RNA Tagging distinguishes between productive and nonproductive binding events in vivo. This asset arises because the poly(U) polymerase adds nucleotides one at a time and the number added can be quantified accurately. The number of uridines added likely is a direct reflection of the time the protein is bound to the RNA (FIG. 9A). A two-dimensional analysis, which simultaneously examined the number of Tagged RNAs and the number of U's they possessed, revealed a strong correlation between in vitro binding affinity and in vivo regulation. The highest ranked Puf3p targets (e.g. Class A) had the best binding elements, were most likely to be localized to mitochondria, and exhibited the largest PUF3-dependent changes in RNA abundance and stability. Thus they are bound and regulated by Puf3p in vivo (FIG. 9B). On the other hand, the lowest ranked Puf3p targets (e.g. Class C) exhibited the weakest enrichments. Thus we collectively define these targets, which have degenerate or less accessible binding elements, as "sampled" RNAs (FIG. 9C). They interact with Puf3p long enough to yield one or two uridines, but the interaction is insufficient for several well-characterized mechanisms of Puf3p-mediated regulation, which in all PUF systems examined, requires recruitment of other effector proteins (Houshmandi, et al., 2005; Lee, et al., 2010; Goldstrohm, et al., 2006; Goldstrohm, et al., 2007; Cho, et al., 2006; Kadyrova, et al., 2007; Suh, et al. 2009; Friend, et al., 2012). On average, the RNAs that are sampled are more abundant, which may help drive their interaction in vivo.

RNA Tagging provides valuable insight into the biological roles of RNA-binding proteins. Bfr1p predominately tagged mRNAs that encode ribosomal and membrane-associated proteins, enrichments missed in earlier RIP-chip studies. Our data are consistent with findings that implicate Bfr1p in the secretory pathway (Jackson, et al., 1994 and Trautwein, et al., 2004) and with its observed subcellular localization (Lang, et al., 2001 and Weidner, et al., 2014). Bfr1p targets lacked a clearly defined binding element and their rank was highly related to their abundance, findings that likely account for the large discrepancy between RNA Tagging and RIP-chip. Additionally, Bfr1p is part of a large protein complex (Lang, et al., 2001) and is required for the localization of mRNAs to P-bodies (Simpson, et al., 2014) and the bud tip (Trautwein, et al., 2004). Thus our findings and previous studies suggest that Bfr1p is an integral component of a trafficking complex that localizes mRNAs to specific locations in the cell, particularly the ER.

RNA Tagging should provide access to areas of RNA biology that until now were very difficult to examine. For example, it may be possible to detect RNAs both directly and indirectly associated with a protein of interest, aided by using a poly(U) polymerase with its own intrinsic but weak RNA-binding activity (Lapointe, et al., 2013). Large protein complexes often contain critical factors that only indirectly associate with RNA, such as several eukaryotic translation initiation factors or components of the CCR4-NOT complex (Jackson, et al., 2010 and Miller et al., 2012). The dynamics of RNA-protein interactions may be analyzed through rapid induction of the tagging protein, providing snapshots of the interactions at a given time. The development of new tagging enzymes that deposit different marks would enable multiple proteins of interest to be probed simultaneously, providing valuable insight into the exchanges of proteins on RNAs, how RNA-binding proteins collaborate to regulate RNA, and the encounters of single RNA molecules in the cell. It remains to be seen whether PUP fusions bound to elements in the 5'UTR will tag efficiently; flexible protein linkers or PUPs that possess higher rates of catalysis may be useful in this regard. Regardless, the versatility of RNA Tagging should enable approaches to unexplored problems in RNA biology in living cells.

We have developed an effective RNA Tagging strategy that covalently marks RNAs bound to a protein of interest in vivo. The approach is simple and generalizable. It yields new insights into how proteins bind and regulate RNA in vivo, particularly as it distinguishes productive and nonproductive binding events. Further adaptations of the method should be able to discern collaborative, competitive, and neutral interactions between multiple proteins and their targets. The ability to unambiguously tag RNAs that bound a protein in vivo provides a definitive mark of that RNA's encounters with proteins, and its history, in the cell.

Accession Codes.

NCBI Sequence Read Archive accession: SRP063022.

Methods

Yeast Strains

All *Saccharomyces cerevisiae* strains were constructed in BY4742 yeast (MATα; his3Δ1; leu2Δ0; lys2Δ0; ura3Δ0). To construct RNA Tagging chimeras, the DNA sequence for the open reading frame (ORF) of *Caenorhabditis elegans* pup-2 followed by a stop codon and the URA3 marker, including its native promoter and terminator sequences, was inserted in-frame at the 3' end of PUF3 and BFR1 using standard yeast transformation techniques. The BFR1-PUP2 strains also contained a 3-HA epitope tag on the C-terminus of the fusion protein. Catalytically inactive PUP2 strains (PUP2mut strains) had Asp185Ala and Asp187Ala substitutions in the PUP-2 protein. For wild-type and mutant PHD1 strains, the endogenous 3' UTR of PHD1 was replaced with URA3 using standard yeast transformation techniques. Next, single colonies were transformed with DNA that encoded an RGSH$_6$ epitope tag fused to the C-terminus of Phd1p, and either the wild-type or mutant PHD1 3' UTRs, which had substitutions that disrupted known Puf5p-binding elements (UGUAGUUA to ACAAGUUA, and UGUAACAUUA (SEQ ID NO:2) to ACAAACAUUA (SEQ ID NO:3)). Cells were selected on 5-FOA containing plates. Integration of the epitope tag and 3' UTRs at the endogenous PHD1 locus was confirmed by sequencing. The pup-2 ORF and a 3-HA epitope tag were then inserted in-frame at the 3' end of PUF5 as above in both the wild-type and mutant PHD1 strains.

Yeast Growth and Total RNA Isolation

All strains were grown by inoculating 5 mL YPAD cultures with the indicated frozen yeast strains or freshly streaked colonies, and incubating at 30° C. and 180 rpm. After ~24 hours, 25 mL YPAD cultures were seeded at $A_{660}$~0.0002 and grown at 30° C. and 180 rpm until $A_{660}$ 0.5-0.8. Yeast were harvested by centrifugation for 10 minutes at 3,000 rpm at 4° C., and the pellets were washed once with 40 mL of ice-cold water. Cells were resuspended in 500 µL RNA ISO Buffer (0.2M Tris-HCl pH 7.5, 0.5M NaCl, 0.01M EDTA, 1% SDS). Then, ~200 µL of acid washed beads and 500 µL of Phenol:Chloroform:Isoamyl alcohol (25:24:1) (PCA) were added. Cells were lysed by vortexing for 20 sec followed by 20 sec on ice ten times. Samples were then separated from the beads, split evenly into two tubes, and 375 µL of RNA ISO Buffer and 375 µL of PCA were added to each tube. Samples were mixed by gently shaking and were separated by centrifugation for 15 minutes at 15,000 rpm at 4° C. The aqueous layer was removed (~500 µL) and further extracted by two additional extractions (PCA followed by chloroform). Following the extractions, the aqueous layer was removed and ~1 mL of 100% ethanol was added to the samples, which were gently mixed and incubated at ~50° C. for >1 hour. Total RNA was pelleted by centrifugation for 30 minutes at 15,000 rpm at 4° C. Pellets were washed 1× with ~70% ethanol, and resuspended in 43 µL of water. Separate tubes for each sample were then recombined, and treated with 8 Units of TURBO DNase (Life Technologies) for 1 hour at 37° C. Total RNA was purified using the GeneJet RNA Purification kit (Thermo Fisher Scientific) and eluted in 30 μL of water. RNA samples were stored at ~80° C.

Targeted RNA Tagging RT-PCR Assays

Terminator treatment: To deplete rRNA, 2 μg of total RNA were treated with 2 Units of Terminator enzyme (Epicentre) for 60 minutes at 30° C. The reactions were subsequently purified using 1.8 volumes of room temperature RNA Clean XP beads (Agencourt) and the standard protocol. rRNA-depleted RNA was eluted in 12 μL of water.

G/I-tailing: Terminator-treated samples were G/I-tailed by using 1,200 Units of yeast poly(A) polymerase (PAP) (Affymetrix), 0.5 mM GTP, 0.15 mM ITP, and incubated at 37° C. for 90 minutes. Samples were diluted to 100 μL with water and G/I-tailed RNA was extracted with two sequential organic extractions (PCA followed by chloroform). The final aqueous layer was removed, and 10 μL of 3 M sodium acetate, 1 μL of GlycoBlue (Life Technologies), and 600 μL of 100% ethanol were added to the samples. Samples were incubated at −50° C. for >1 hour. Samples were pelleted by centrifugation for 30 minutes at 15,000 rpm at 4° C. Pellets were washed once in ~70% ethanol, and resuspended in 10 μL of water.

Selective reverse transcription: G/I-tailed samples were selectively reverse transcribed using SuperScript III reverse transcriptase (Invitrogen) under nearly standard conditions. The G/I-tailed samples were split equally (typically 3 μL) across all RT reactions. 3 μL of samples were added to 1 μL of 1 μM U-select primer (GCCTTGGCACCCGAGAATTC-CACCCCCCCCCAAA SEQ ID NO:4), 1 μL of 10 mM dNTP mix, and 8 μL of water (13 μL total). Oligo-(dT) and -RT reactions used 1 μL of 1 μM oligo-(dT)$_{42}$ (TTTTTTTTTTTTTTTTTTTTTTTTTTTTTTTTTTTTTTTTTT SEQ ID NO:5) in place of the U-select primer. A master mix of 4 μL of 5× reaction buffer, 1 μL of 100 mM DTT and 1 μL of 40 U per μL RNase Inhibitor per reaction was prepared separately. The primer-RNA mixes and the master mix were incubated at 65° C. for 5 minutes followed by 5 minutes at 50° C. in a thermocycler. With the primer-RNA mixes and the master mix still in the 50° C. thermocycler, RT enzyme was added to the master mix (except for -RT samples), mixed thoroughly, and 7 μL of the resulting master mix was added to the primer-RNA mix. Samples were then incubated at 50° C. for 60 minutes followed by 5 minutes at 85° C.

Polymerase chain reactions: 1 μL of cDNA straight from the RT reactions was PCR amplified using GoTaq Polymerase (Promega). The HSP10 specific forward primer was: GACAGCATCCGGGTTGTATT (SEQ ID NO:6). The HSP10 specific reverse primer was: TTTTCCTGTCATA-CATAATGGCC (SEQ ID NO:7). HSP10 primers and the U-select primer were used at final concentrations of ~1 μM and ~40 nM, respectively. The COX17 specific forward primer was ATGACTGAAACTGACAAGAAAC (SEQ ID NO:8) when used with the U-select primer. The internal COX17 primers were: ACAAGAACAAGAAAACCACGC (SEQ ID NO:9) and AAGATGCATGTATCCCGCTC (SEQ ID NO:10). All COX17 reactions were performed with final primer concentrations of ~40 nM. PCR parameters and steps were as follows: 1) 95° C. for 3 min, 2) 95° C. for 30 sec, 3) 50° C. for 30 sec, 4) 72° C. for 90 sec, 5) repeat steps 2-4 24 times (HSP10) or 36 times (COX17), 6) 72° C. for 5 min, and 7) hold at 4° C.

Cloning and Sanger sequencing: HSP10 PCR products were cloned using the TOPO-TA Cloning kit (Life Technologies), standard reaction conditions, and blue-white colony screening. Individual white colonies were grown in 5 mL of lysogeny broth (LB)-ampicillin media. Plasmids were isolated from saturated cultures using the GeneJET Plasmid Miniprep kit (Thermo Scientific (Fermentas)) and subsequently Sanger sequenced using standard reaction conditions.

Transcriptome-Wide RNA Tagging Library Preparations

Poly(A) selection and rRNA depletion: Approximately 75 μg of high-quality total RNA were poly(A) selected using the Dynabeads mRNA Purification kit (Life Technologies) and the standard protocol. Samples were eluted in 28 μL of water. The poly(A)-selected RNA was then depleted of rRNA using the RihoZeroGold (yeast) kit (Epicentre) and the standard protocol. Samples were eluted in 12 μL of water.

G/I-tailing: Samples were G/I-tailed as above, except for the following step. After the initial 90 minute G/I-tailing reaction, an additional 1,200 Units of yeast PAP was added to the reactions and incubated for an additional 30 minutes at 37° C. G/I-tailed RNA was purified as above using PCA.

Selective reverse transcription and RNase H digestion: G/I-tailed samples were selectively reverse transcribed as above. cDNAs were digested with 1 μL of RNaseH (invitrogen) for 20 minutes at 37° C. cDNAs were purified using the GeneJet PCR Purification kit (Thermo Fisher Scientific). cDNAs were eluted twice in 32 μL of water giving a total of ~60 μL cDNA.

Second strand synthesis: 60 μL of cDNA was added to 10 μL of 10× Klenow Buffer (500 mM Tris-HCl pH 7.5, 100 mM MgCL$_2$, 10 mM DTT, 0.5 mg per mL BSA), 12 μL of water, 5 μL of 10 mM dNTPs, 10 μL of 10 μM 2$^{nd}$ strand synthesis primer (GTTCAGAGTTCTACAGTCCGAC-GATCNNNNNN SEQ ID NO:11), and 3 μL of 5 U per μL Exo-Klenow DNA Polymerase (Life Technologies). Reactions were incubated at 37° C. for 30 minutes, and then purified twice using RNA Clean XP beads (Agencourt) at a 1:1 (bead:reaction) ratio. dsDNA was eluted in 50 μL of water.

Polymerase chain reactions: Samples were PCR amplified using GoTaq polymerase (Promega). 5 μL of cDNA was added to 8.33 μL of 2× GoTaqGreen master mix, 2 μL of water, 0.67 μL of 10 μM RP1 primer (AATGATACGGC-GACCACCGAGATCTACACGTTCAGAGTTCTACA-GTCCGA SEQ ID NO:12), and 0.67 μL of 10 μM barcoded primer (CAAGCAGAAGACGGCATACGA-GATXXXXXXGTGACTGGAGTTCCTTGGCACCCGA-GAATTCC A SEQ. ID NO:13). Standard Illumina barcodes were inserted at the XXXXXX position in the primer. The PCR cycle was: 1) 94° C. for 2 min, 2) 94° C. for 10 sec, 3) 40° C. for 2 min, 4) 72° C. for 1 min, 5) Repeat 2-4 once, 6) 94° C. for 10 sec, 7) 55° C. for 30 sec 8) 72° C. for 1 min, 9) Repeat 6-8 7×, 10) 94° C. for 15 sec, 11) 55° C. for 30 sec, 12) 72° C. for 1 min, 13) Repeat 10-12 14 times, 14) 72° C. for 5 min, 15) Hold at 4° C. To scale up, ~9 individual reactions were completed for each sample and were pooled prior to cleanup. PCR samples were size-selected twice using the RNA Clean XP beads at a 0.8:1 (bead:reaction) ratio. Samples were eluted in ~20 μL of water.

Synthetic U-Tag Libraries

Preparation: Synthesized oligos were purchased (Integrated DNA Technologies) and their sequences were: CCT-TGGCACCCGAGAATTCCACCCCCCCCAAA(A) TTTTTTTTTTTGATCGTCGGACTGTAG AACTCTGAAC (SEQ ID NO:14). At the (A) 0, 2, 4, 6, 8, 10, and 12 adenosines were inserted to create various length U-tag standards. Synthetic libraries were amplified using GoTaq polymerase, 0.8 μL RP1 oligo, 0.8 μM barcoded primer, and 2 nM of oligo as template. Otherwise, the PCR conditions were the same as for the transcriptome-wide library preparations. Completed reactions were run on a 6% acrylamide TBE-Urea gel, and the bands corresponding to the libraries were excised from the gel (~180 bps). The gel slices were crushed in 200 µL of water, flash frozen, incubated at 37° C. and 1,000 rpm for 1 hour, flash frozen again, incubated at 37° C. and 1,000 rpm for 1 hour, and separated using a filter column. The libraries were ethanol precipitated with GlycoBlue as the co-precipitant. Pellets were washed once in 70% ethanol and resuspended in 10-20 µL of water.

Analysis: Raw FASTQ files of the sequenced libraries were analyzed two different ways. First, the number of uridines in the U-tag of every read in each of the libraries was determined. Using this data, the mean U-tag length (in nucleotides) and associated standard deviation was calculated for each of the synthetic libraries. Second, the base composition at each position for every read in the libraries was determined. These calculations were then used to determine how often a single uridine residue was detected in the A0 library (no U-tag encoded in the synthesized oligo), which served as the background rate referenced below.

High-Throughput Sequencing

Samples were sequenced on an Illumina HiSeq 2500 instrument to obtain 50 base pair paired-end read data sets. Throughout, the first: sequencing read, which covers the 5' end of the sequenced DNA fragment, is termed "Read 1", and the second sequencing read, which covers the 3' end of the sequenced DNA fragment, is termed "Read 2". Raw data was deposited at the NCBI Sequence Read Archive (accession: SRP063022).

FASTQ File Manipulations and Alignments

Read 1: All FASTQ processing (FASTX-toolkit, http://hannonlab.cshl.edu/fastx_toolkit/) and alignments to the yeast genome were done using local installations of the given software. The U-select primer sequence (TTTGGGGGGGGGTGGAATTCTCGGGTGCCAAGG SEQ ID NO:15) and the poly(A) tail sequence (AAAAAAAAAA SEQ ID NO:16) were removed from Read 1's using FASTA/Q Clipper [fastx_clipper -a sequence -l 15 -n -I -v input -o output -Q 34]. Any Read 1's that were shorter than 15 nucleotides after removal of either sequence were discarded. Reads 1's were then aligned to the *S. cerevisiae* genome (version R64-1-1) using bowtie (Langmead, et al., 2009) with the following parameters: a seed length (-l) of 25 nucleotides, no more than 2 mismatches (-n), and only a single reportable alignment (-m) in the genome [bowtie -t genome input output -l 25 -m 1 -S --sam -p 3 -n 2]. Reads that aligned to more than one location were discarded, Read 2: The 5' adapter sequence (GATCGTCGGACTG-TAGAACTCTGAAC SEQ ID NO:17) was removed from Read 2's using FASTA/Q Clipper and the same parameters as above. The last six nucleotides of the resulting Read 2's, which represent the random hexamer sequence from the $2^{nd}$ strand synthesis step, were then removed using FASTA/Q Trimmer [fastx_trimmer -t 6 -i input -o output -Q 34]. The resulting Read 2's were reverse complemented using FASTA/Q Reverse Complement [fastx_reverse_complement -i input -o output -Q 34] and any sequence corresponding to the U-select primer sequence was removed as above. Sequences with at least 3 adenosines followed any number of uridines at their 3' end (A-U tail sequences) were identified using regular expression searches in Perl. Read 2's were aligned twice to the yeast genome: first without any A-U tail sequence and then with any A-U tail sequence. This alignment process identified Read 2's with A-U tail sequences that were not encoded in the genome. Bowtie alignments were conducted essentially as above, except that the seed length was 20 nucleotides and the -v alignment mode was used to exclude reads with 3 or more mismatches.

Definition of Tagged RNAs

A Tagged RNA was defined as a DNA fragment with sequence that aligned uniquely to the yeast genome and contained at least 8 adenosines followed by at least 1 uridine at their 3' end that were not encoded by any adapter sequence or the genome. Typically, Read 1 identified the genomic location of a Tagged RNA while Read 2 identified its A-U tail sequence. Read 2 also frequently determined the 3' terminus of an RNA. The number of Tagged RNAs per gene was calculated and normalized across samples (TRPM, Tagged RNAs per million uniquely mapped reads).

Reproducible RNA Tagging Targets

In order to be identified as a target, genes with Tagged RNAs had to pass three criteria. First, the number of TRPMs detected for a particular gene must be at least 10-fold greater than the number of TRPMs detected for that gene in the non-tagging control sample. Second, the number of TRPMs detected for a particular gene must be greater than the error rate for falsely detecting Tagged RNAs. A uridine was erroneously detected 3% of the time on a synthetic polyadenylated library without a U-tag (FIG. 11B) (see above for synthetic libraries). Thus, the error rate was defined as the number of TRPM detected by error per gene [0.03*(total # of TRPM)/(total # of genes with TRPM)]. Third, a gene must have passed both of the above criteria in all of the biological replicates.

Hierarchical Clustering

Tagged RNAs per million uniquely mapped reads (TRPM) for each target were calculated across U-tag lengths of 1-10 uridines for each sample. TRPMs for biological replicates were then averaged (mean). Each U-tag length encompassed all TRPMs with at least the indicated number of uridines. Prior to clustering, the data was sorted from most to least TRPMs detected with at least 1 U in the U-tag. The data sets were $\log_2$-transformed and hierarchically clustered using the Gene Cluster 3.0 software. Heat maps were generated in Matlab (version R2014a).

Definition of Target Classes

To begin, classes were loosely defined to encompass groups of targets with similar TRPM and U-tag length profiles. Boundaries between putative target classes were defined by the dendrogram from the clustering analysis. Statistical analyses (as outlined below) were conducted on each putative class, sequentially from the highest ranked class to the lowest ranked class, to determine if it was distinct from directly adjacent putative classes. As an example, the enrichment of putative Class A targets for a given observation (e.g. RNAs with increased abundance in ⓐ PUF3) was compared to the enrichment in putative Class B targets. If the enrichments of putative Class A and B targets were statistically indistinguishable, they were combined and the analysis was repeated with the next adjacent putative class (Class C). If the enrichments of putative Class A and B targets were statistically different, putative Class A targets were defined as actual Class A targets, and the process was repeated with the remaining putative classes until only distinct classes remained.

Statistical Analyses

All statistical analyses were done using RStudio (R version 3.1.2). Linear regression analyses were used to obtain $R^2$ values and the associated P-values [summary(lm(y~x))]. Shapiro-Wilk tests [shapiro.test(x)] were used to test normality as needed. Spearman's (ρ and Pearson's (r) correlation coefficients and their associated P-values were determined using the rcorr function from the hmisc package

[rcorr(x, y, type="spearman") and rcorr(x, y, type="pearson"), respectively]. Hypergeometric distribution tests [phyper( )] were used to determine if the observed overlap between two datasets was significant. The total population size was defined as 6,607 genes, except for the following analyses: mRNA localization to mitochondria (6,256 genes), proteins with predicted transmembrane domains (TMHMM analyses, 6,713 genes), and yeast GFP protein localization (4,156 genes). Cumulative fraction plots were generated using the empirical cumulative distribution function (ecdt) [plot(ecdf(x), do.points=F, verticals=T, lty=1, lwd=3, . . . )]. Two-sided Kolmogorov-Smirnov tests were performed using the ks.test function [ks.test(x,y)]. For FIGS. 15B and 15C and 24B, Fisher-Pitman permutation tests and permutations of the Wilcoxon-Mann-Whitney test were conducted using the coin package [pvalue(oneway_test (DV~IV, distribution=approximate(B=1000000))) and pvalue(wilcox_test(DV~IV, distribution=approximate (B=1000000))), respectively]. Both tests behaved similarly for all comparisons. Where indicated, data was randomized 100,000 times using the sample function.

Venn Diagrams

Proportional Venn diagrams were generated using Biovenn (Hulsen, et al., 2008) (and then redrawn for publication).

MEME and Directed Motif Searches

To be as inclusive as possible, 3' UTRs were defined as the longest isoform for a particular gene previously observed (Xu, et al., 2009) or, if not previously defined, as 200 bases. MEME (Bailey, 1994) analyses were done on a local server using the following command [meme.bin input.txt -oc outputdirectory -dna -mod zoops -nmotifs 5 -minw 6 -maxw 15]. The 'maxsize' parameter was adjusted as needed. Enriched sequence motifs were identified in the 3' UTRs of Puf3p targets and indicated subsets using MEME as described above. To determine the binding motif present in each class of Puf3p targets, the binding elements present in each class, as determined using all of the Puf3p targets, were combined to generate the indicated motifs in FIG. 6A. Unbiased MEME analyses were conducted as above on each of the classes to identify enriched motifs in the 5' UTRs, open-reading frames, and 3' UTRs, which confirmed the findings reported in FIG. 6A. The RIP-chip motif was identified in the 3' UTRs of the previously identified targets using MEME as above. The PAR-CLIP motif was previously identified (Freeberg, et al., 2013) but shortened here for consistency. In all cases, motifs were prepared for publication using WebLogo 3 (Crooks, et al., 2004). The total number of genes with the C[AUC]UGUA[AUC]AUA (SEQ ID NO:18) consensus sequence in their 3' UTR was determined using a Perl regular expression search on all 3' UTR sequences. Genes with at least one occurrence of the motif were counted as positives.

PBE Location in 3' UTRs

Many 3' termini of mRNAs were detected in our data, especially when all RNAs that were detected with a poly(A) tail of at least 8 adenosines (with or without a U-tag) were included. Using this information, the most detected isoform for particular mRNAs, the lengths of the 3' UTRs, and the position of the PBE relative to the stop codon and 3' termini were determined. Genes with undetected 3' termini, and genes with negative or very large (>1,000 nucleotides) distances to 3' termini were excluded from the analyses. For FIGS. 15D and 15E, the mean number of Tagged RNAs, number of U's added, and distance from the PBE to the 3' terminus for isoforms of 64 Puf3p targets (144 distinct mRNAs) detected by at least 31 reads (24,417 reads total) were calculated and compared. In these analyses, Tagged RNAs with U-tags of more than 6 U's were not analyzed since our deep sequencing did not yield 3' termini for those mRNAs.

GO Analyses

All GO analyses were completed using Yeast Mine from the *Saccharomyces* Genome Database (yeastmine.yeastgenome.org). All parameters were set to default (Holm-Bonferroni corrected).

TMHMM Prediction

To identify proteins with a predicted transmembrane domain (TMD), the sequences of all proteins (6,713 proteins, including dubious proteins) were downloaded from the *Saccharomyces* Genome Database. The sequences were then analyzed using the TMHMM 2.0 server (Krogh, et al., 2001). Proteins with at least 1 predicted TMD were counted as positives.

RNA-Seq

RNA isolation: Total RNA was isolated from *S. cerevisiae* (BY4742) cells using standard methods. 50 ml of cells with $A_{660}$ 0.5-0.8 were collected by centrifugation at 3,200 rpm at 4° C., washed once with cold water, and snap frozen in liquid $N_2$. The tubes were vortexed for 30 seconds then incubated on ice for 30 seconds, which was repeated six times. The supernatant was removed, extracted with 1 mL of PCA, and ethanol precipitated. RNA pellets were resuspended in 50 µL water.

Library preparations: 2 µg of RNA were used as input. Samples were depleted of rRNA using the Ribo-Zero Magnetic Gold Kit (Yeast) kit (Epicentre) and the standard protocol. Libraries were prepared using the TruSeq Stranded Total RNA kit (Illumina) and the standard protocol with 12 rounds of PCR. PCR samples were purified twice using RNA Clean XP beads and were eluted in 30 µL water. Libraries were sequenced on an Illumina HiSeq 2000 to get 50 base pair reads.

Data analysis: Mapped reads were assigned to genomic features by HTseq-count [htseq-count -s](version 0.5.4p3). The mean number of fragments per kilobase of exon per million reads mapped (FPKM) of four biological replicates was calculated for each genomic feature Example: Poly(C) Polymerase Activity of *Schizosaccharomyces pombe* SPAC1093.04

The yeast *S. cerevisiae* was used to detect the activity of *Schizosaccharomyces pombe* SPAC1093.04 by tethering the enzyme to a reporter tRNA containing an MS2 stem loop and then sequencing added tails. BY4741 yeast strains expressing both the reporter tRNA and SPAC1093.04 fused to MS2 coat protein (MS2) were grown log phase (OD=0.8-1.0) in synthetic media lacking uracil and leucine to select for the presence of the desired plasmids. When the MS2-SPAC1093.04 fusion protein binds to the MS2 stem loop, it adds a tail to the 3' end of the reporter tRNA.

Total RNA, including the tailed reporter tRNA, was isolated by lysis of yeast with acid-washed beads followed by phenol-chloroform extraction and ethanol precipitation. The RNA was treated with TURBO™ DNase (available from Ambion/ThermoFisher Scientific, Waltham, Mass.) to remove contaminating DNA, and the RNA was purified by using an RNA extraction kit (available from ThermoFisher Scientific, Waltham, Mass.). Total RNA was ligated with a 5' adenylated adapter containing a 5'-terminal random heptamer and a 3' dideoxycytidine (5' AppNNNNNNN TGGAATTCTCGGGTGCCAAGG ddC SEQ ID NO:19 3') to prevent ligation of multiple adapters onto the same RNA molecule by using T4 RNA ligase 2, truncated KQ (available from New England Biolabs, Ipswich, Mass.). The adapter-modified reporter RNA was reverse transcribed with the ImProm-II™ reverse transcription system (available from Promega, Madison, Wis.) using a primer complementary to the adapter sequence (5' GCCTTGGCACCCGAGAAT-TCCA SEQ ID NO:20 3'). The resulting cDNA was PCR amplified using a 5' primer containing a sequence specific for the tRNA reporter (5' GAGGATCACCCATGTCGCAG SEQ ID NO:21 3') and a 3' primer containing sequence complementary to the adapter sequence.

Samples underwent high-throughput sequencing to identify the sequences of tails added to the reporter RNA. To generate PCR products compatible with Illumina® sequencing platforms, appropriate sequences to allow for binding of DNA fragments to the sequencing flow cell were added to the 5' and 3' PCR primers described above (5' primer: 5' AATGATACGGCGACCACCGAGATCTACACGTTCA-GAGTTCTACAGTCCGACGATCGAGGATC ACCCAT-GTCGCAG 3' SEQ ID NO:22 and 3' primer: 5' CAAAGCA-GAAGACGGCATACGAGAT (SEQ ID NO:23) –6 nt sample index—GTGACTGGAGTTCCTTGGCACCCGA-GAATTCCA (SEQ ID NO:24) 3'). Paired-end sequence reads were generated by sequencing the samples in the 5' and 3' directions on an Illumina® HiSeq® 2500 instrument. The resulting sequencing reads were processed using a custom Python script to identify the nucleotide tails added, to remove PCR duplicate sequences (using the random heptamer sequence on the 3' adapter), and to quantify length, abundance, and nucleotide composition of each tail sequence.

The results for SPAC1093.04 are shown in FIG. 25B,C. Referring to FIG. 25B, the percent nucleotide composition of the population and the number of unique tails (calculated as tails per million unique random heptamers) as a function of tail length are plotted. The tails are dominated by the presence of C and A. Referring to FIG. 25C, some of the most abundant tail sequences are shown with their respective relative abundance. Strikingly, in most cases, the tail sequence is a poly(C) sequence. Thus, SPAC1093.04 has poly(C) polymerase activity. In some cases, the poly(C) sequence is followed by a poly(A) sequence, which may indicate that endogenous poly(A) polymerases in yeast add A's to the C-tailed reporter. Alternatively, SPAC1093.04 adds a stretch of C's followed by a stretch of A's. In either case, a poly(C) sequence is added, which is a unique sequence that can be easily identified in the transcriptome by high-throughput sequencing.

The present invention has been described in terms of one or more preferred embodiments, and it should be appreciated that many equivalents, alternatives, variations, and modifications, aside from those expressly stated, are possible and within the scope of the invention.

REFERENCES

Chang, H., Lim, J., Ha, M., and Kim, V. N. (2014). TAIL-seq: genome-wide determination of poly(A) tail length and 3' end modifications. Mol Cell 53, 1044-1052.

Gerber, A. P., Herschlag, D., and Brown, P. O. (2004). Extensive association of functionally and cytotopically related mRNAs with Puf family RNA-binding proteins in yeast. PLoS biology 2, E79.

Kwak, J. E., and Wickens, M. (2007). A family of poly(U) polymerases. RNA 13, 860-867.

Lapointe, C. P., and Wickens, M. 2013. The nucleic acid-binding domain and translational repression activity of a *Xenopus* terminal uridylyl transferase. J Biol Chem 288, 20723-20733.

McHugh, C. A., Russell, P., and Guttman, M. (2014). Methods for comprehensive experimental identification of RNA-protein interactions. Genome biology 15, 203.

Ota, R., Kotani, T., and Yamashita, M. (2011). Biochemical characterization of Pumilio1 and Pumilio2 in *Xenopus* oocytes. J Biol Chem 286, 2853-2863.

Subtelny, A. O., Eichhorn, S. W., Chen, G. R., Sive, H., and Bartel, D. P. (2014). Poly(A)-tail profiling reveals an embryonic switch in translational control. Nature 508, 66-71.

Wickens, M., Bernstein, D. S., Kimble, J., and Parker, R. (2002). A PUF family portrait: 3'UTR regulation as a way of life. Trends Genet 18, 150-157.

Zhu, D., Stumpf, C. R., Krahn, J. M., Wickens, M., and Hall, T. M. (2009). A 5' cytosine binding pocket in Puf3p specifies regulation of mitochondrial mRNAs. Proc Natl Acad Sci USA 106, 20192-20197.

Carlile, T. M., Rojas-Duran, M. F., Zinshteyn, B., Shin, H., Bartoli, K. M., and Gilbert, W. V. (2014). Pseudouridine profiling reveals regulated mRNA pseudouridylation in yeast and human cells. Nature doi:10.1038/nature13802.

Geisberg, J. V., Mogtaderi, Z., Fan, X., Ozsolak, F., and Struhl, K., (2014). Global analysis of mRNA isoform half-lives reveals stabilizing and destabilizing elements in yeast. Cell 156(4), 812-824.

McHugh, C. A., Russell, P. & Guttman, M. Methods for comprehensive experimental identification of RNA-protein interactions. *Genome biology* 15, 203, doi:10.1186/gb4152 (2014).

Tenenbaum, S. A., Carson, C. C., Lager, P. J. & Keene, J. D. Identifying mRNA subsets in messenger ribonucleoprotein complexes by using cDNA arrays. *Proc Natl Acad Sci USA* 97, 14085-14090, doi:10.1073/pnas.97.26.14085 (2000).

Zhao, J. et al. Genome-wide identification of polycomb-associated RNAs by RIP-seq. *Mol Cell* 40, 939-953, doi:10.1016/j.molcel.2010.12.011 (2010).

Ule, J. et al. CLIP identifies Nova-regulated RNA networks in the brain. *Science* 302, 1212-1215, doi:10.1126/science.1090095 (2003).

Licatalosi, D. D. et al. HITS-CLIP yields genome-wide insights into brain alternative RNA processing. *Nature* 456, 464-469, doi:10.1038/nature07488 (2008).

Hafner, M. et al. Transcriptome-wide identification of RNA-binding protein and microRNA target sites by PAR-CLIP. *Cell* 141, 129-141, doi:10.1016/j.cell.2010.03.009 (2010).

Konig, J. et al. iCLIP reveals the function of hnRNP particles in splicing at individual nucleotide resolution. *Nat Struct Mol Biol* 17, 909-915, doi:10.1038/nsmb.1838 (2010).

Mili, S. & Steitz, J. A. Evidence for reassociation of RNA-binding proteins after cell lysis: implications for the interpretation of immunoprecipitation analyses. *RNA* 10, 1692-1694, doi:10.1261/rna.7151404 (2004).

Riley, K. J., Yario, T. A. & Steitz, J. A. Association of Argonaute proteins and microRNAs can occur after cell lysis. *RNA* 18, 1581-1585, doi:10.1261/rna.034934.112 (2012).

Riley, K. J. & Steitz, J. A. The "Observer Effect" in genome-wide surveys of protein-RNA interactions. *Mol Cell* 49, 601-604, doi:10.1016/j.molcel.2013.01.030 (2013).

Darnell, R. B. HITS-CLIP: panoramic views of protein-RNA regulation in living cells. *Wiley Interdiscip Rev RNA* 1, 266-286, doi:10.1002/wrna.31 (2010).

Fecko, C. J. et al. Comparison of femtosecond laser and continuous wave UV sources for protein-nucleic acid crosslinking. *Photochem Photobiol* 83, 1394-1404, doi:10.1111/j.1751-1097.2007.00179.x (2007).

Lapointe, C. P. & Wickens, M. The nucleic acid-binding domain and translational repression activity of a *Xenopus* terminal uridylyl transferase. *J Biol Chem* 288, 20723-20733, doi:10.1074/jbc.M113.455451 (2013).

Kim, B. et al. TUT7 controls the fate of precursor microRNAs by using three different uridylation mechanisms. *EMBO J* 34, 1801-1815, doi:10.15252/embj.201590931 (2015).

Gerber, A. P., Herschlag, D. & Brown, P. O. Extensive association of functionally and cytotopically related mRNAs with Puf family RNA-binding proteins in yeast. *PLoS biology* 2, E79, doi:10.1371/journal.pbio.0020079 (2004).

Zhu, D., Stumpf, C. R., Krahn, J. M., Wickens, M. & Hall, T. M. A 5' cytosine binding pocket in Puf3p specifies regulation of mitochondrial mRNAs. *Proc Natl Acad Sci USA* 106, 20192-20197, doi:10.1073/pnas.0812079106 (2009).

Olivas, W. & Parker, R. The Puf3 protein is a transcript-specific regulator of mRNA degradation in yeast. *EMBO J* 19, 6602-6611, doi:10.1093/emboj/19.23.6602 (2000).

Saint-Georges, Y. et al. Yeast mitochondrial biogenesis: a role for the PUF RNA-binding protein Puf3p in mRNA localization. *PLoS One* 3, e2293, doi:10.1371/journal.pone.0002293 (2008).

Gadir, N., Haim-Vilmovsky, L., Kraut-Cohen, J. & Gerst, J. E. Localization of mRNAs coding for mitochondrial proteins in the yeast *Saccharomyces cerevisiae*. *RNA* 17, 1551-1565, doi:10.1261/rna.2621111 (2011).

Chatenay-Lapointe, M. & Shadel, G. S. Repression of mitochondrial translation, respiration and a metabolic cycle-regulated gene, SLF1, by the yeast Pumilio-family protein Puf3p. *PLoS One* 6, e20441, doi:10.1371/journal.pone.0020441 (2011).

Garcia-Rodriguez, L. J., Gay, A. C. & Pon, L. A. Puf3p, a Pumilio family RNA binding protein, localizes to mitochondria and regulates mitochondrial biogenesis and motility in budding yeast. *J Cell Biol* 176, 197-207, doi:10.1083/jcb.200606054 (2007).

Wilinski, D. et al. RNA regulatory networks diversified through curvature of the PUF protein scaffold. *Nat Commun* 6, doi:10.1038/ncomms9213 (2015).

Kusov, Y. Y., Shatirishvili, G., Dzagurov, G. & Gauss-Muller, V. A new G-tailing method for the determination of the poly(A) tail length applied to hepatitis A virus RNA. *Nucleic Acids Res* 29, E57-57 (2001).

Lane, A. N., Chaires, J. B., Gray, R. D. & Trent, J. O. Stability and kinetics of G-quadruplex structures. *Nucleic Acids Res* 36, 5482-5515, doi:10.1093/nar/gkn517 (2008).

Freeberg, M. A. et al. Pervasive and dynamic protein binding sites of the mRNA transcriptome in *Saccharomyces cerevisiae*. *Genome biology* 14, R13, doi:10.1186/gb-2013-14-2-r13 (2013).

Bailey, T. E., C. Fitting a mixture model by expectation maximization to discover motifs in biopolymers. *Proceedings of the Second International Conference on Intelligent Systems for Molecular Biology* Aug. 28-36 (1994).

Miller, M. A., Russo, J., Fischer, A. D., Lopez Leban, F. A. & Olivas, W. M. Carbon source-dependent alteration of Puf3p activity mediates rapid changes in the stabilities of mRNAs involved in mitochondrial function. *Nucleic Acids Res* 42, 3954-3970, doi:10.1093/nar/gkt1346 (2014).

Wickens, M., Bernstein, D. S., Kimble, J. & Parker, R. A PUF family portrait: 3'UTR regulation as a way of life. *Trends Genet* 18, 150-157, doi:S0168952501026166 [pii] (2002).

Hogan, D. J., Riordan, D. P., Gerber, A. P., Herschlag, D. & Brown, P. O. Diverse RNA-binding proteins interact with functionally related sets of RNAs, suggesting an extensive regulatory system. *PLoS biology* 6, e255, doi:10.1371/journal.pbio.0060255 (2008).

Jackson, J. S., Jr., Houshmandi, S. S., Lopez Leban, F. & Olivas, W. M. Recruitment of the Puf3 protein to its mRNA target for regulation of mRNA decay in yeast. *RNA* 10, 1625-1636, doi:10.1261/rna.7270204 (2004).

Houshmandi, S. S. & Olivas, W. M. Yeast Puf3 mutants reveal the complexity of Puf-RNA binding and identify a loop required for regulation of mRNA decay. *RNA* 11, 1655-1666, doi:10.1261/rna.2168505 (2005).

Huh, W. K. et al. Global analysis of protein localization in budding yeast. *Nature* 425, 686-691, doi:10.1038/nature02026 (2003).

Williams, C. C., Jan, C. H. & Weissman, J. S. Targeting and plasticity of mitochondrial proteins revealed by proximity-specific ribosome profiling. *Science* 346, 748-751, doi:10.1126/science.1257522 (2014).

Sun, M. et al. Global analysis of eukaryotic mRNA degradation reveals Xrn1-dependent buffering of transcript levels. *Mol Cell* 52, 52-62, doi:10.1016/j.molcel.2013.09.010 (2013).

Jackson, C. L. & Kepes, F. BFR1, a multicopy suppressor of brefeldin A-induced lethality, is implicated in secretion and nuclear segregation in *Saccharomyces cerevisiae*. *Genetics* 137, 423-437 (1994).

Trautwein, M., Dengjel, J., Schirle, M. & Spang, A. Arf1p provides an unexpected link between COPI vesicles and mRNA in *Saccharomyces cerevisiae*. *Mol Biol Cell* 15, 5021-5037, doi:10.1091/mbc.E04-05-0411 (2004).

Lang, B. D., Li, A., Black-Brewster, H. D. & Fridovich-Keil, J. L. The brefeldin A resistance protein Bfr1p is a component of polyribosome-associated mRNP complexes in yeast. *Nucleic Acids Res* 29, 2567-2574 (2001).

Weidner, J., Wang, C., Prescianotto-Baschong, C., Estrada, A. F. & Spang, A. The polysome-associated proteins Scp160 and Bfr1 prevent P body formation under normal growth conditions. *J Cell Sci* 127, 1992-2004, doi:10.1242/jcs.142083 (2014).

Simpson, C. E., Lui, J., Kershaw, C. J., Sims, P. F. & Ashe, M. P. mRNA localization to P-bodies in yeast is bi-phasic with many mRNAs captured in a late Bfr1p-dependent wave. *J Cell Sci* 127, 1254-1262, doi:10.1242/jcs.139055 (2014).

Ast, T., Cohen, G. & Schuldiner, M. A network of cytosolic factors targets SRP-independent proteins to the endoplasmic reticulum. *Cell* 152, 1134-1145, doi:10.1016/j.cell.2013.02.003 (2013).

Mitchell, S. F., Jain, S., She, M. & Parker, R. Global analysis of yeast mRNPs. *Nat Struct Mol Biol* 20, 127-133, doi:10.1038/nsmb.2468 (2013).

Jan, C. H., Williams, C. C. & Weissman, J. S. Principles of ER cotranslational translocation revealed by proximity-specific ribosome profiling. *Science* 346, 1257521, doi:10.1126/science.1257521 (2014).

Munoz-Tello, P., Rajappa, L., Coquille, S. & Thore, S. Polyuridylation in Eukaryotes: A 3'-End Modification Regulating RNA Life. *Biomed Res Int* 2015, 968127, doi:10.1155/2015/968127 (2015).

Norbury, C. J. Cytoplasmic RNA: a case of the tail wagging the dog. *Nat Rev Mol Cell Biol* 14, 643-653, doi:10.1038/nrm3645 (2013).

Chang, H., Lim, J., Ha, M. & Kim, V. N. TAIL-seq: genome-wide determination of poly(A) tail length and 3' end modifications. *Mol Cell* 53, 1044-1052, doi:10.1016/j.molcel.2014.02.007 (2014).

Newman, M. A., Mani, V. & Hammond, S. M. Deep sequencing of microRNA precursors reveals extensive 3' end modification. *RNA* 17, 1795-1803, doi:10.1261/rna.2713611 (2011).

Lee, D. et al. PUF3 acceleration of deadenylation in vivo can operate independently of CCR4 activity, possibly involving effects on the PAB1-mRNP structure. *J Mol Biol* 399, 562-575, doi:10.1016/j.jmb.2010.04.034 (2010).

Goldstrohm, A. C., Hook, B. A., Seay, D. J. & Wickens, M. PUF proteins bind Pop2p to regulate messenger RNAs. *Nat Struct Mol Biol* 13, 533-539, doi:10.1038/nsmb1100 (2006).

Goldstrohm, A. C., Seay, D. J., Hook, B. A. & Wickens, M. PUF protein-mediated deadenylation is catalyzed by Ccr4p. *J Biol Chem* 282, 109-114, doi:10.1074/jbc.M609413200 (2007).

Cho, P. F. et al. Cap-dependent translational inhibition establishes two opposing morphogen gradients in *Drosophila* embryos. *Curr Biol* 16, 2035-2041, doi:10.1016/j.cub.2006.08.093 (2006).

Kadyrova, L. Y., Habara, Y., Lee, T. H. & Wharton, R. P. Translational control of maternal Cyclin B mRNA by Nanos in the *Drosophila* germline. *Development* 134, 1519-1527, doi:10.1242/dev.002212 (2007).

Suh, N. et al. FBF and its dual control of gld-1 expression in the *Caenorhabditis elegans* germline. *Genetics* 181, 1249-1260, doi:10.1534/genetics.108.099440 (2009).

Friend, K. et al. A conserved PUF-Ago-eEF1A complex attenuates translation elongation. *Nat Struct Mol Biol* 19, 176-183, doi:10.1038/nsmb.2214 (2012).

Jackson, R. J., Hellen, C. U. & Pestova, T. V. The mechanism of eukaryotic translation initiation and principles of its regulation. *Nat Rev Mol Cell Biol* 11, 113-127, doi: 10.1038/nrm2838 (2010).

Miller, J. E. & Reese, J. C. Ccr4-Not complex: the control freak of eukaryotic cells. *Crit Rev Biochem Mol Biol* 47, 315-333, doi:10.3109/10409238.2012.667214 (2012).

Langmead, B., Trapnell, C., Pop, M. & Salzberg, S. L. Ultrafast and memory-efficient alignment of short DNA sequences to the human genome. *Genome biology* 10, R25, doi:10.1186/gb-2009-10-3-r25 (2009).

Hulsen, T., de Vlieg, J. & Alkema, W. BioVenn—a web application for the comparison and visualization of biological lists using area-proportional Venn diagrams. *BMC Genomics* 9, 488, doi:10.1186/1471-2164-9-488 (2008).

Xu, Z. et al. Bidirectional promoters generate pervasive transcription in yeast. *Nature* 457, 1033-1037, doi: 10.1038/nature07728 (2009).

Crooks, G. E., Hon, G., Chandonia, J. M. & Brenner, S. E. WebLogo: a sequence logo generator. *Genome Res* 14, 1188-1190, doi:10.1101/gr.849004 (2004)

Krogh, A., Larsson, B., von Heijne, G. & Sonnhammer, E. L. Predicting transmembrane protein topology with a hidden Markov model: application to complete genomes. *J Mol Biol* 305, 567-580, doi:10.1006/jmbi.2000.4315 (2001).

We claim:

1. A method for identifying, among a total RNA population, an RNA to which a protein of interest selectively binds in a cellular environment of a cell of interest, the method comprising:

(a) expressing a fusion protein within the cellular environment, the fusion protein comprising at least part of the protein of interest and a tagging domain, the tagging domain introducing a selective tag to an RNA to which the fusion protein selectively binds, the selective tag comprising a selective tag sequence or a selective covalent modification;

(b) allowing the tagging domain to tag the RNA to which the protein of interest selectively binds by waiting for about 1 minute to about 28 days; and (c) identifying the tagged RNA.

2. The method of claim 1 wherein step (c) includes:

(d) isolating the total RNA population of the cell of interest from other cellular material resulting in isolated total RNA;

(e) reverse transcribing the isolated total RNA using a primer having a sequence that is complementary to at least part of the selective tag sequence or the selective covalent modification resulting in a single-stranded cDNA complementary to RNA including the selective tag;

(f) synthesizing a cDNA strand complementary to the single-stranded cDNA resulting in a dsDNA;
(g) amplifying the dsDNA;
(h) purifying the amplified dsDNA resulting in purified dsDNA; and
(i) sequencing the purified dsDNA.

3. The method of claim 1, wherein the total RNA population is a total RNA population of a subcellular structure, a total RNA population of a secreted component, a total RNA population of a virus, a total RNA population of cellular origin, or a combination thereof.

4. The method in claim 1, wherein expressing the fusion protein includes exposing the cell of interest to an extracellular structure containing the fusion protein.

5. The method of claim 4, wherein the extracellular structure is viral.

6. A method for identifying, among a total RNA population of a cell of interest, any RNA to which any protein of interest selectively binds in a cellular environment of the cell of interest, the method comprising:
(a) expressing a fusion protein within the cellular environment, the fusion protein comprising the protein of interest and a tagging domain, the tagging domain introducing a selective tag to RNA to which the fusion protein selectively binds, the selective tag comprising a selective tag sequence or a selective covalent modification;
(b) isolating RNA from the cell resulting in isolated total RNA;
(c) attaching an in vitro added tail to the 3' end of the isolated total RNA resulting in tailed total RNA, the in vitro added tail comprising a tail sequence;
(d) selectively reverse transcribing the tailed total RNA using a primer having a sequence that is complementary to at least part of the selective tag sequence or the selective covalent modification and at least part of the tail sequence resulting in a single-stranded cDNA complementary to RNA including the selective tag and the in vitro added tail;
(e) synthesizing a cDNA strand complementary to the single-stranded cDNA resulting in a dsDNA;
(f) amplifying the dsDNA;
(g) purifying the amplified dsDNA resulting in purified dsDNA; and
(h) sequencing the purified dsDNA.

7. The method of claim 6, the method further comprising:
(i) depleting rRNA and tRNA from the isolated total RNA resulting in rRNA/tRNA-depleted isolated total RNA, wherein step (c) utilizes the rRNA/tRNA-depleted isolated total RNA in place of the isolated total RNA.

8. The method of claim 7, the method further comprising:
(j) poly(A) selecting the isolated total RNA resulting in poly(A)-selected isolated total RNA, wherein step (i) utilizes the poly(A)-selected isolated total RNA in place of the isolated total RNA.

9. The method of claim 6, the method further comprising:
(k) cleaning the dsDNA.

10. The method of claim 6, the method further comprising:
(l) analyzing biological function relative to sequences that are shared among the RNA to which the protein of interest selectively bind.

11. A method of selectively sequencing a sub-selection of a total RNA population, the method comprising:
(a) selectively tagging the sub-selection with a selective tag having a selective sequence or a selective covalent modification;
(b) in vitro tailing the total RNA population;
(c) selectively reverse transcribing the sub-selection using a primer having a sequence that is complementary to at least part of the selective tag sequence or the selective covalent modification and at least part of the in vitro-added tail sequence to produce cDNA complementary to the sub-selection;
(d) synthesizing a cDNA strand complementary to the single-stranded cDNA resulting in a dsDNA;
(e) amplifying the dsDNA;
(f) purifying the amplified dsDNA resulting in purified dsDNA; and
(g) sequencing the purified dsDNA.

12. The method of claim 11, the method further comprising:
(h) analyzing biological function relative to sequences that are shared among the sub-selection.

13. The method of claim 1, wherein multiple, non-identical fusion proteins are expressed in step (a).

14. The method of claim 13 wherein the non-identical fusion proteins differ in the tagging domain.

15. The method of claim 13 wherein the non-identical fusion proteins differ in the protein of interest.

* * * * *

UNITED STATES PATENT AND TRADEMARK OFFICE
CERTIFICATE OF CORRECTION

PATENT NO. : 10,160,968 B2
APPLICATION NO. : 14/946020
DATED : December 25, 2018
INVENTOR(S) : Marvin P. Wickens et al.

It is certified that error appears in the above-identified patent and that said Letters Patent is hereby corrected as shown below:

In the Specification

Column 16, Line 64, "Illumine™" should be -- Illumina™ --.

Column 17, Line 37, "Illumine™" should be -- Illumina™ --.

Column 17, Line 52, "Illumine™" should be -- Illumina™ --.

Column 17, Line 54, "Illumine™" should be -- Illumina™ --.

Column 17, Line 59, "Illumine™" should be -- Illumina™ --.

Column 21, Line 4, "Mill" should be -- Mili --.

Column 33, Line 11, "(ecdt)" should be -- (ecdf) --.

Signed and Sealed this
Nineteenth Day of February, 2019

Andrei Iancu
*Director of the United States Patent and Trademark Office*

SEQUENCE LISTING

<160> NUMBER OF SEQ ID NOS: 60

<210> SEQ ID NO 1
<211> LENGTH: 10
<212> TYPE: RNA
<213> ORGANISM: Artificial Sequence
<220> FEATURE:
<223> OTHER INFORMATION: synthetic sequence

<400> SEQUENCE: 1 chuguahaua                                                          10

<210> SEQ ID NO 2
<211> LENGTH: 10
<212> TYPE: RNA
<213> ORGANISM: Artificial Sequence
<220> FEATURE:
<223> OTHER INFORMATION: synthetic sequence

<400> SEQUENCE: 2
uguaacauua                                                          10

<210> SEQ ID NO 3
<211> LENGTH: 10
<212> TYPE: RNA
<213> ORGANISM: Artificial Sequence
<220> FEATURE:
<223> OTHER INFORMATION: synthetic sequence

<400> SEQUENCE: 3
acaaacauua                                                          10

<210> SEQ ID NO 4
<211> LENGTH: 34
<212> TYPE: DNA
<213> ORGANISM: Artificial Sequence
<220> FEATURE:
<223> OTHER INFORMATION: synthetic sequence

<400> SEQUENCE: 4
gccttggcac ccgagaattc caccccccccc caaa                                34

<210> SEQ ID NO 5
<211> LENGTH: 42
<212> TYPE: DNA
<213> ORGANISM: Artificial Sequence
<220> FEATURE:
<223> OTHER INFORMATION: synthetic sequence

<400> SEQUENCE: 5
tttttttttt tttttttttt tttttttttt tttttttttt tt                        42

<210> SEQ ID NO 6
<211> LENGTH: 20
<212> TYPE: DNA
<213> ORGANISM: Artificial Sequence
<220> FEATURE:
<223> OTHER INFORMATION: synthetic sequence

<400> SEQUENCE: 6
gacagcatcc gggttgtatt                                                 20

<210> SEQ ID NO 7
<211> LENGTH: 23
<212> TYPE: DNA
<213> ORGANISM: Artificial Sequence
<220> FEATURE:
<223> OTHER INFORMATION: synthetic sequence

<400> SEQUENCE: 7
ttttcctgtc atacataatg gcc                                             23

<210> SEQ ID NO 8
<211> LENGTH: 22
<212> TYPE: DNA
<213> ORGANISM: Artificial Sequence
<220> FEATURE:
<223> OTHER INFORMATION: synthetic sequence

<400> SEQUENCE: 8
atgactgaaa ctgacaagaa ac                                              22

<210> SEQ ID NO 9
<211> LENGTH: 21
<212> TYPE: DNA
<213> ORGANISM: Artificial Sequence
<220> FEATURE:
<223> OTHER INFORMATION: synthetic sequence

<400> SEQUENCE: 9
acaagaacaa gaaaaccacg c                                               21

<210> SEQ ID NO 10
<211> LENGTH: 20
<212> TYPE: DNA
<213> ORGANISM: Artificial Sequence
<220> FEATURE:

<223> OTHER INFORMATION: synthetic sequence

<400> SEQUENCE: 10
aagatgcatg tatcccgctc                                               20

<210> SEQ ID NO 11
<211> LENGTH: 32
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (27)..(32)
<223> OTHER INFORMATION: n is a, c, g, or t

<400> SEQUENCE: 11
gttcagagtt ctacagtccg acgatcnnnn nn                                 32

<210> SEQ ID NO 12
<211> LENGTH: 50
<212> TYPE: DNA
<213> ORGANISM: Artificial Sequence
<220> FEATURE:
<223> OTHER INFORMATION: synthetic sequence

<400> SEQUENCE: 12
aatgatacgg cgaccaccga gatctacacg ttcagagttc tacagtccga              50

<210> SEQ ID NO 13
<211> LENGTH: 63
<212> TYPE: DNA
<213> ORGANISM: Artificial Sequence
<220> FEATURE:
<223> OTHER INFORMATION: synthetic sequence
<220> FEATURE:
<221> NAME/KEY: misc_signal
<222> LOCATION: (25)..(30)
<223> OTHER INFORMATION: n is standard Illumina barcodes

<400> SEQUENCE: 13
caagcagaag acggcatacg agatnnnnnn gtgactggag ttccttggca cccgagaatt   60
cca                                                                 63

<210> SEQ ID NO 14
<211> LENGTH: 72
<212> TYPE: DNA
<213> ORGANISM: Artificial Sequence
<220> FEATURE:
<223> OTHER INFORMATION: synthetic sequence

<400> SEQUENCE: 14
ccttggcacc cgagaattcc acccccccccc aaaattttttt tttttttgatc gtcggactgt   60 agaactctga ac                                                       72

<210> SEQ ID NO 15
<211> LENGTH: 33
<212> TYPE: DNA
<213> ORGANISM: Artificial Sequence
<220> FEATURE:
<223> OTHER INFORMATION: synthetic sequence

<400> SEQUENCE: 15 tttgggggggg ggtggaattc tcgggtgcca agg                               33

```
<210> SEQ ID NO 16
<211> LENGTH: 10
<212> TYPE: DNA
<213> ORGANISM: Artificial Sequence
<220> FEATURE:
<223> OTHER INFORMATION: synthetic sequence

<400> SEQUENCE: 16
aaaaaaaaaa                                                                 10

<210> SEQ ID NO 17
<211> LENGTH: 26
<212> TYPE: DNA
<213> ORGANISM: Artificial Sequence
<220> FEATURE:
<223> OTHER INFORMATION: synthetic sequence

<400> SEQUENCE: 17
gatcgtcgga ctgtagaact ctgaac                                               26

<210> SEQ ID NO 18
<211> LENGTH: 14
<212> TYPE: RNA
<213> ORGANISM: Artificial Sequence
<220> FEATURE:
<223> OTHER INFORMATION: synthetic sequence

<400> SEQUENCE: 18
caucuguaau caua                                                            14

<210> SEQ ID NO 19
<211> LENGTH: 28
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(7)
<223> OTHER INFORMATION: n is a, c, g, t or u

<400> SEQUENCE: 19
nnnnnnntgg aattctcggg tgccaagg                                             28

<210> SEQ ID NO 20
<211> LENGTH: 22
<212> TYPE: DNA
<213> ORGANISM: Artificial Sequence
<220> FEATURE:
<223> OTHER INFORMATION: synthetic sequence

<400> SEQUENCE: 20
gccttggcac ccgagaattc ca                                                   22

<210> SEQ ID NO 21
<211> LENGTH: 20
<212> TYPE: DNA
<213> ORGANISM: Artificial Sequence
<220> FEATURE:
<223> OTHER INFORMATION: synthetic sequence

<400> SEQUENCE: 21
gaggatcacc catgtcgcag                                                      20

<210> SEQ ID NO 22
<211> LENGTH: 75
<212> TYPE: DNA
```

```
<213> ORGANISM: Artificial Sequence
<220> FEATURE:
<223> OTHER INFORMATION: synthetic sequence

<400> SEQUENCE: 22
aatgatacgg cgaccaccga gatctacacg ttcagagttc tacagtccga cgatcgagga    60
tcacccatgt cgcag                                                    75

<210> SEQ ID NO 23
<211> LENGTH: 25
<212> TYPE: DNA
<213> ORGANISM: Artificial Sequence
<220> FEATURE:
<223> OTHER INFORMATION: synthetic sequence

<400> SEQUENCE: 23
caaagcagaa gacggcatac gagat                                         25

<210> SEQ ID NO 24
<211> LENGTH: 33
<212> TYPE: DNA
<213> ORGANISM: Artificial Sequence
<220> FEATURE:
<223> OTHER INFORMATION: synthetic sequence

<400> SEQUENCE: 24
gtgactggag ttccttggca cccgagaatt cca                                33

<210> SEQ ID NO 25
<211> LENGTH: 20
<212> TYPE: RNA
<213> ORGANISM: Artificial Sequence
<220> FEATURE:
<223> OTHER INFORMATION: synthetic sequence
<220> FEATURE:
<221> NAME/KEY: modified_base
<222> LOCATION: (9)..(9)
<223> OTHER INFORMATION: I
<220> FEATURE:
<221> NAME/KEY: misc_feature
<222> LOCATION: (9)..(9)
<223> OTHER INFORMATION: n is I inosine
<220> FEATURE:
<221> NAME/KEY: modified_base
<222> LOCATION: (12)..(12)
<223> OTHER INFORMATION: I
<220> FEATURE:
<221> NAME/KEY: misc_feature
<222> LOCATION: (12)..(12)
<223> OTHER INFORMATION: n is I inosine
<220> FEATURE:
<221> NAME/KEY: modified_base
<222> LOCATION: (16)..(16)
<223> OTHER INFORMATION: I
<220> FEATURE:
<221> NAME/KEY: misc_feature
<222> LOCATION: (16)..(16)
<223> OTHER INFORMATION: n is I inosine
<220> FEATURE:
<221> NAME/KEY: modified_base
<222> LOCATION: (18)..(18)
<223> OTHER INFORMATION: I
<220> FEATURE:
<221> NAME/KEY: misc_feature
<222> LOCATION: (18)..(18)
<223> OTHER INFORMATION: n is I inosine

<400> SEQUENCE: 25
uuuuugggng ngggngngg                                                20
```

```
<210> SEQ ID NO 26
<211> LENGTH: 12
<212> TYPE: RNA
<213> ORGANISM: Artificial Sequence
<220> FEATURE:
<223> OTHER INFORMATION: synthetic sequence

<400> SEQUENCE: 26 aaacccccc cc                                                              12

<210> SEQ ID NO 27
<211> LENGTH: 14
<212> TYPE: DNA
<213> ORGANISM: Artificial Sequence
<220> FEATURE:
<223> OTHER INFORMATION: synthetic sequence

<400> SEQUENCE: 27
aaaaaccccc cccc                                                           14

<210> SEQ ID NO 28
<211> LENGTH: 14
<212> TYPE: DNA
<213> ORGANISM: Artificial Sequence
<220> FEATURE:
<223> OTHER INFORMATION: synthetic sequence

<400> SEQUENCE: 28
tttttggggg gggg                                                           14

<210> SEQ ID NO 29
<211> LENGTH: 18
<212> TYPE: DNA
<213> ORGANISM: Artificial Sequence
<220> FEATURE:
<223> OTHER INFORMATION: synthetic sequence

<400> SEQUENCE: 29
tttttttttt tttttttt                                                       18

<210> SEQ ID NO 30
<211> LENGTH: 26
<212> TYPE: RNA
<213> ORGANISM: Artificial Sequence
<220> FEATURE:
<223> OTHER INFORMATION: synthetic sequence
<220> FEATURE:
<221> NAME/KEY: modified_base
<222> LOCATION: (18)..(18)
<223> OTHER INFORMATION: I
<220> FEATURE:
<221> NAME/KEY: misc_feature
<222> LOCATION: (18)..(18)
<223> OTHER INFORMATION: n is I inosine
<220> FEATURE:
<221> NAME/KEY: modified_base
<222> LOCATION: (22)..(22)
<223> OTHER INFORMATION: I
<220> FEATURE:
<221> NAME/KEY: misc_feature
<222> LOCATION: (22)..(22)
<223> OTHER INFORMATION: n is I inosine
<220> FEATURE:
<221> NAME/KEY: modified_base
<222> LOCATION: (25)..(25)
<223> OTHER INFORMATION: I
<220> FEATURE:
<221> NAME/KEY: misc_feature
<222> LOCATION: (25)..(25)
<223> OTHER INFORMATION: n is I inosine
```

```
<400> SEQUENCE: 30
aaaaaaaaaa auuuuugngg gnggng                                          26

<210> SEQ ID NO 31
<211> LENGTH: 38
<212> TYPE: DNA
<213> ORGANISM: Artificial Sequence
<220> FEATURE:
<223> OTHER INFORMATION: synthetic sequence

<400> SEQUENCE: 31
aattgaaaaa aaaaaaaaaa aaaaaaattt tttttttt                             38

<210> SEQ ID NO 32
<211> LENGTH: 55
<212> TYPE: DNA
<213> ORGANISM: Artificial Sequence
<220> FEATURE:
<223> OTHER INFORMATION: synthetic sequence

<400> SEQUENCE: 32
aattgaactc aaaaaaaaaa aaaaaaaaaa aaaaaaaaaa attttttttt ttttt          55

<210> SEQ ID NO 33
<211> LENGTH: 39
<212> TYPE: DNA
<213> ORGANISM: Artificial Sequence
<220> FEATURE:
<223> OTHER INFORMATION: synthetic sequence

<400> SEQUENCE: 33
aattgaactc aaaaaaaaaa aaaaaaaaaa aaattttttt                           39

<210> SEQ ID NO 34
<211> LENGTH: 37
<212> TYPE: DNA
<213> ORGANISM: Artificial Sequence
<220> FEATURE:
<223> OTHER INFORMATION: synthetic sequence

<400> SEQUENCE: 34
aattgaactc aaatttcttc aaaaaaaaaa aaatttt                              37

<210> SEQ ID NO 35
<211> LENGTH: 71
<212> TYPE: DNA
<213> ORGANISM: Artificial Sequence
<220> FEATURE:
<223> OTHER INFORMATION: synthetic sequence

<400> SEQUENCE: 35
gttcagagtt ctacagtccg acgatcaaaa aaaaaaaatt tggggggggg tggaattctc     60
gggtgccaag g                                                          71

<210> SEQ ID NO 36
<211> LENGTH: 73
<212> TYPE: DNA
<213> ORGANISM: Artificial Sequence
<220> FEATURE:
<223> OTHER INFORMATION: synthetic sequence

<400> SEQUENCE: 36
gttcagagtt ctacagtccg acgatcaaaa aaaaaaaatt tttggggggg ggtggaattc     60
tcgggtgcca agg                                                        73
```

<210> SEQ ID NO 37
<211> LENGTH: 75
<212> TYPE: DNA
<213> ORGANISM: Artificial Sequence
<220> FEATURE:
<223> OTHER INFORMATION: synthetic sequence

<400> SEQUENCE: 37
gttcagagtt ctacagtccg acgatcaaaa aaaaaaaatt tttttggggg gggtggaat     60 tctcgggtgc caagg                                                    75

<210> SEQ ID NO 38
<211> LENGTH: 77
<212> TYPE: DNA
<213> ORGANISM: Artificial Sequence
<220> FEATURE:
<223> OTHER INFORMATION: synthetic sequence

<400> SEQUENCE: 38
gttcagagtt ctacagtccg acgatcaaaa aaaaaaaatt ttttttggg ggggggtgga    60 attctcgggt gccaagg                                                  77

<210> SEQ ID NO 39
<211> LENGTH: 79
<212> TYPE: DNA
<213> ORGANISM: Artificial Sequence
<220> FEATURE:
<223> OTHER INFORMATION: synthetic sequence

<400> SEQUENCE: 39
gttcagagtt ctacagtccg acgatcaaaa aaaaaaaatt tttttttttg gggggggtg    60 gaattctcgg gtgccaagg                                                79

<210> SEQ ID NO 40
<211> LENGTH: 81
<212> TYPE: DNA
<213> ORGANISM: Artificial Sequence
<220> FEATURE:
<223> OTHER INFORMATION: synthetic sequence

<400> SEQUENCE: 40
gttcagagtt ctacagtccg acgatcaaaa aaaaaaaatt tttttttttt tgggggggg    60 tggaattctc gggtgccaag g                                             81

<210> SEQ ID NO 41
<211> LENGTH: 83
<212> TYPE: DNA
<213> ORGANISM: Artificial Sequence
<220> FEATURE:
<223> OTHER INFORMATION: synthetic sequence

<400> SEQUENCE: 41
gttcagagtt ctacagtccg acgatcaaaa aaaaaaaatt tttttttttt tttggggggg    60
ggtggaattc tcggtgcca agg                                             83

<210> SEQ ID NO 42
<211> LENGTH: 26
<212> TYPE: DNA
<213> ORGANISM: Artificial Sequence
<220> FEATURE:
<223> OTHER INFORMATION: synthetic sequence -continued

```
<400> SEQUENCE: 42
gttcagagtt ctacagtccg acgatc                                          26

<210> SEQ ID NO 43
<211> LENGTH: 12
<212> TYPE: DNA
<213> ORGANISM: Artificial Sequence
<220> FEATURE:
<223> OTHER INFORMATION: synthetic sequence

<400> SEQUENCE: 43
aaaaaaaaaa aa                                                         12

<210> SEQ ID NO 44
<211> LENGTH: 12
<212> TYPE: DNA
<213> ORGANISM: Artificial Sequence
<220> FEATURE:
<223> OTHER INFORMATION: synthetic sequence

<400> SEQUENCE: 44
tttttttttt tt                                                         12

<210> SEQ ID NO 45
<211> LENGTH: 10
<212> TYPE: RNA
<213> ORGANISM: Artificial Sequence
<220> FEATURE:
<223> OTHER INFORMATION: synthetic sequence

<400> SEQUENCE: 45
ccuguaaaua                                                            10

<210> SEQ ID NO 46
<211> LENGTH: 10
<212> TYPE: RNA
<213> ORGANISM: Artificial Sequence
<220> FEATURE:
<223> OTHER INFORMATION: synthetic sequence

<400> SEQUENCE: 46
ccuguauaua                                                            10

<210> SEQ ID NO 47
<211> LENGTH: 10
<212> TYPE: RNA
<213> ORGANISM: Artificial Sequence
<220> FEATURE:
<223> OTHER INFORMATION: synthetic sequence

<400> SEQUENCE: 47
cuuguauaua                                                            10

<210> SEQ ID NO 48
<211> LENGTH: 10
<212> TYPE: RNA
<213> ORGANISM: Artificial Sequence
<220> FEATURE:
<223> OTHER INFORMATION: synthetic sequence

<400> SEQUENCE: 48
acuguaaaua                                                            10

<210> SEQ ID NO 49
<211> LENGTH: 10
```

```
<212> TYPE: RNA
<213> ORGANISM: Artificial Sequence
<220> FEATURE:
<223> OTHER INFORMATION: synthetic sequence

<400> SEQUENCE: 49
uuuguauaua                                                              10

<210> SEQ ID NO 50
<211> LENGTH: 10
<212> TYPE: RNA
<213> ORGANISM: Artificial Sequence
<220> FEATURE:
<223> OTHER INFORMATION: synthetic sequence

<400> SEQUENCE: 50
auuguauaua                                                              10

<210> SEQ ID NO 51
<211> LENGTH: 10
<212> TYPE: RNA
<213> ORGANISM: Artificial Sequence
<220> FEATURE:
<223> OTHER INFORMATION: synthetic sequence

<400> SEQUENCE: 51
cauguaaaua                                                              10

<210> SEQ ID NO 52
<211> LENGTH: 10
<212> TYPE: RNA
<213> ORGANISM: Artificial Sequence
<220> FEATURE:
<223> OTHER INFORMATION: synthetic sequence

<400> SEQUENCE: 52
cguguaaaua                                                              10

<210> SEQ ID NO 53
<211> LENGTH: 10
<212> TYPE: RNA
<213> ORGANISM: Artificial Sequence
<220> FEATURE:
<223> OTHER INFORMATION: synthetic sequence

<400> SEQUENCE: 53
ucuguaaaua                                                              10

<210> SEQ ID NO 54
<211> LENGTH: 10
<212> TYPE: RNA
<213> ORGANISM: Artificial Sequence
<220> FEATURE:
<223> OTHER INFORMATION: synthetic sequence

<400> SEQUENCE: 54
cuuguaaaua                                                              10

<210> SEQ ID NO 55
<211> LENGTH: 10
<212> TYPE: RNA
<213> ORGANISM: Artificial Sequence
<220> FEATURE:
<223> OTHER INFORMATION: synthetic sequence

<400> SEQUENCE: 55
```

```
cauguauaua                                                          10

<210> SEQ ID NO 56
<211> LENGTH: 10
<212> TYPE: RNA
<213> ORGANISM: Artificial Sequence
<220> FEATURE:
<223> OTHER INFORMATION: synthetic sequence

<400> SEQUENCE: 56
uuuguaaaua                                                          10

<210> SEQ ID NO 57
<211> LENGTH: 10
<212> TYPE: RNA
<213> ORGANISM: Artificial Sequence
<220> FEATURE:
<223> OTHER INFORMATION: synthetic sequence

<400> SEQUENCE: 57
cccccccccc                                                          10

<210> SEQ ID NO 58
<211> LENGTH: 11
<212> TYPE: RNA
<213> ORGANISM: Artificial Sequence
<220> FEATURE:
<223> OTHER INFORMATION: synthetic sequence

<400> SEQUENCE: 58
ccccccccaa a                                                        11

<210> SEQ ID NO 59
<211> LENGTH: 12
<212> TYPE: RNA
<213> ORGANISM: Artificial Sequence
<220> FEATURE:
<223> OTHER INFORMATION: synthetic sequence

<400> SEQUENCE: 59
ccccccccaa aa                                                       12

<210> SEQ ID NO 60
<211> LENGTH: 10
<212> TYPE: RNA
<213> ORGANISM: Artificial Sequence
<220> FEATURE:
<223> OTHER INFORMATION: synthetic sequence

<400> SEQUENCE: 60
ccccccccaa                                                          10
```